(12) United States Patent
Sarikaya et al.

(10) Patent No.: US 9,809,633 B2
(45) Date of Patent: Nov. 7, 2017

(54) REAGENTS AND METHODS FOR TREATING DENTAL DISEASE

(71) Applicant: University of Washington through its Center for Commercialization, Seattle, WA (US)

(72) Inventors: Mehmet Sarikaya, Seattle, WA (US); Martha Somerman, Bethesda, MD (US); Candan Tamerler-Behar, Seattle, WA (US); Hanson Fong, Seattle, WA (US); Hai Zhang, Seattle, WA (US); Mustafa Gungormus, Seattle, WA (US)

(73) Assignee: University of Washington Through its Center for Commercialization, Seattle, WA (US)

(*) Notice: Subject to any disclaimer, the term of this patent is extended or adjusted under 35 U.S.C. 154(b) by 0 days.

(21) Appl. No.: 15/015,360

(22) Filed: Feb. 4, 2016

(65) Prior Publication Data
US 2016/0152672 A1    Jun. 2, 2016

Related U.S. Application Data

(62) Division of application No. 14/117,595, filed as application No. PCT/US2012/039650 on May 25, 2012, now Pat. No. 9,290,555.

(60) Provisional application No. 61/509,986, filed on Jul. 20, 2011, provisional application No. 61/490,757, filed on May 27, 2011.

(51) Int. Cl.
| | | |
|---|---|---|
| *A61K 38/00* | (2006.01) | |
| *A61K 8/64* | (2006.01) | |
| *A61K 8/65* | (2006.01) | |
| *A61Q 11/00* | (2006.01) | |
| *C07K 14/47* | (2006.01) | |
| *C07K 14/78* | (2006.01) | |
| *C07K 14/00* | (2006.01) | |

(52) U.S. Cl.
CPC .............. *C07K 14/47* (2013.01); *A61K 8/64* (2013.01); *A61K 8/65* (2013.01); *A61Q 11/00* (2013.01); *C07K 14/4705* (2013.01); *C07K 14/78* (2013.01); *A61K 38/00* (2013.01); *C07K 2319/40* (2013.01); *C07K 2319/43* (2013.01)

(58) Field of Classification Search
CPC . A61K 38/00; A61K 8/64; A61K 8/65; A61Q 11/00; C07K 14/47; C07K 14/4705; C07K 14/48; C07K 14/00; C07K 2319/40; C07K 2319/43

USPC ...... 514/21.3, 21.4, 21.5; 530/325, 327, 350
See application file for complete search history.

(56) References Cited

U.S. PATENT DOCUMENTS

| | | | |
|---|---|---|---|
| 6,677,306 B1* | 1/2004 | Veis .................. | C07K 14/78 |
| | | | 424/422 |
| 7,078,021 B2 | 7/2006 | Yoneda et al. | |
| 7,294,352 B2 | 11/2007 | Gestrelius et al. | |
| 2003/0170378 A1 | 9/2003 | Wen et al. | |
| 2010/0070200 A1 | 3/2010 | Sarikaya et al. | |
| 2014/0186273 A1* | 7/2014 | Moradian-Oldak ... | A61K 8/736 |
| | | | 424/50 |

FOREIGN PATENT DOCUMENTS

| | | |
|---|---|---|
| JP | 2013-177368 | 9/2013 |
| WO | 00/06734 | 2/2000 |
| WO | 2008/021290 | 2/2008 |
| WO | 2009/157869 A1 | 12/2009 |
| WO | 2011/077086 | 6/2011 |
| WO | 2011/073447 | 3/2012 |
| WO | 2012166626 | 12/2012 |
| WO | 2016/115283 A2 | 7/2016 |

OTHER PUBLICATIONS

B2BY38 from UniProt, pp. 1-4. Integrated into UniProtKB/TrEMBL May 20, 2008.*
Einhauer et al., "The FLAGTM peptide, a versatile fusion tag for the purificaiton of recombinant proteins," J. Biochem. Biophys. Methods, 2001, 49: 455-465.*
English translation of Office Action in JP 2014-512155, dated Apr. 5, 2016.
Achilles et al. (1995) "In Vitro Fromation of 'Urinary Stones' Generation of Spherulites of Calcium Phosphate in Gel and Overgrowth With Calcium Oxalate Using a New Flow Model of Crystallization," Scanning Microscopy, 9(2):577-586.
Altschul et al. (1997) "Gapped BLAST and PSI-BLAST: a new generation of protein database search programs," Nucleic Acids Research, 25(17):3389-3402.
Aoba et al. (1989) "Possible Roles of Partial Sequences at N- and C-termini of Amelogenin in Protein-Enamel Mineral Interaction," Journal of Dental Research, 68(9):1331-1336.
Arys et al. (1989) "Brushite in the pulp of primary molars," Journal of Oral Pathology and Medicine, 18(7):371-376.

(Continued)

*Primary Examiner* — Julie Ha
(74) *Attorney, Agent, or Firm* — McDonnell Boehnen Hulbert & Berghoff LLP

(57) ABSTRACT

Peptide-based reagents, compositions and oral care products containing the peptide-based reagents, and methods for using the peptide-based reagents, compositions, or oral care products to treat dental diseases such as periodontitis, tooth erosion, hypersensitivity, bacterial plaque, dental fluorosis, tooth decay, carries, tooth resorption, and gingival recession, are described.

21 Claims, 10 Drawing Sheets

(56) References Cited

OTHER PUBLICATIONS

Bartlett et al. (2006) "Protein-Protein Interactions of the Developing Enamel Matrix," Current Topics in Developmental Biology, 74:57-115.

Beniash et al. (2005) "The effect of recombinant mouse amelogenins on the formation and organization of hydroxyapatite crystals in vitro," Journal of Structural Biology, 149(2):182-190.

Berman et al. (2000) "Dynamical stability and quantum chaos of ions in a linear trap," Physical Review A, 61(2):023403-1-023403-16.

Boskey et al. (2000) "Dentin Sialoprotein (DSP) Has Limited Effects on In Vitro Apatite Formation and Growth," Calcified Tissue International, 67(6): 472-478.

Capriotti et al. (2007) "Hydroxyapatite Surface-Induced Peptide Folding," Journal of the American Chemical Society, 129(16):5281-5287.

Chelliah et al. (2004) "Distinguishing Structural and Functional Restraints in Evolution in Order to Identify Interaction Sites," Journal of Molecular Biology, 342(5):1487-1504.

Cheng et al. (2005) "Improvement in protein functional site prediction by distinguishing structural and functional constraints on protein family evolution using computational design," Nucleic Acids Research, 33(18):5861-5867.

Du et al. (2005) "Supramolecular assembly of Amelogenin Nanospheres into Birefringent Microribbons," Science, 307 (5714)1450-1454.

Dunglas et al. (2001) "Ultrastructure of forming enamel in mouse bearing a transgene that disrupt amelogenin assembly domains," Journal of Dental Research (Abstracts of Papers), 80(4):1278-1278.

Eanes and J.L. Meyer (1977) "The Maturation of Crystalline Calcium Phosphates in Aqueous Suspensions at Physiologic pH," Calcified Tissue Research, 23(3):259-269.

Eddy (1998) "Hidden Markov Models and Genome Sequence Analysis," FASEB Journal (Abstracts), 12(8):A1327-A1327.

Elangovan et al. (2007) "Conformational Changes in Salivary Proline-Rich Protein 1 upon Adsorption to Calcium Phosphate Crystals," Langmuir, 23(22):11200-11205.

Fan et al. (2004) "Regulation of myocardial function by histidine-rich, calcium-binding protein," American Journal of Physiology—Heart and Circulatory Physiology, 287(4):H1705-H1711.

Fan et al. (2009) "Controlled remineralization of enamel in the presence of amelogenin and fluoride," Biomaterials, 30(4):478-483.

Fan et al. (2011) "The Cooperation of Enamelin and Amelogenin in Controlling Octacalcium Phosphate Crystal Morphology," Cells Tissues Organs, 194(2-4):194-198.

Fong et al. (2001) "Microarchitectural Study of Rodent Enamel by X-ray Microtomography," Argonne National Laboratory, available online at: http://www.aps.anl.gov/apsar2001/HFONG1.PDF.

Fong et al. (2003) "Enamel Biomineralization Controlled by Amelogenin Self-Assembly [Abstract]," in Proceedings of the 32nd Annual Meeting and Exhibition of the International Association for Dental Research (AADR), San Antonio, TX, Mar. 12-15, 2003, 1 page, available online at: http://iadr.confex.com/iadr/2003SanAnton/techprogram/abstract_26279.htm.

Gajjeraman et al. (2007) "Matrix Molecules in Hard Tissues Control the Nucleation and Hierarchical Assembly of Hydroxyapatite," Journal of Biological Chemistry, 282(2):1193-1204.

Gay et al. (2007) "Isolation and characterization of multipotent human periodontal ligament stem cells," Orthodontics and Craniofacial Research, 10(3):149-160.

Ginalski et al. (2005) "3D-Jury: a simple approach to improve protein structure predictions," Bioinformatics, 19(8)1015-1018.

Goldberg et al. (2001) "Binding of Bone Sialoprotein, Osteopontin and Synthetic Polypeptides to Hydroxyapatite," Connective Tissue Research, 42(1):25-37.

Gregory et al. (2006) "Histidine-rich Ca binding protein: a regulator of sarcoplasmic reticulum calcium sequestration and cardiac function," Journal of Molecular and Cellular Cardiology, 40(5):653-665.

Gu et al. (2011) "Immobilization of a phosphonated analog of matrix phosphoproteins within cross-linked collagen as a templating mechanism for biomimetic mineralization," Acta Biomaterialia, 7(1):268-277.

Gungormus et al. (2010) "Self assembled bi-functional peptide hydrogels with biomineralization-directing peptides," Biomaterials, 31(28):7266-7274.

He et al. (2003) "Dentin Matrix Protein 1 Initiates Hydroxyapatite Formation In Vitro," Connective Tissue Research, 44 :Suppl. 1):240-245.

Ho et al. (2009) "Structure, chemical composition and mechanical properties of human and rat cementum and its interface with root dentin," Acta Biomaterialia, 5(2):707-718.

Horst et al. (2008) "Mineral-binding region predicted and demonstrated within exon 6ABC of Amelogenin [Abstract]," in Proceedings of the 37th Annual Meeting and Exhibition of the International Association for Dental Research (AADR), Dallas, TX, Mar. 31-Apr. 5, 2008, 1 page, available online at: https://iadr.confex.com/iadr/2008Dallas/techprogramforcd/A101575.htm.

Hung et al. (2005) "PROTINFO: new algorithms for enhanced protein structure predictions," Nucleic Acids Research, 33:W77-W80.

Ijima and J. Moradian-Oldak (2004) "Interactions of Amelogenins with Octacalcium Phosphate Crystal Faces are Dose Dependent," Calcified Tissue International, 74:522-531.

Ivanovski et al. (2006) "Stem cells in the periodontal ligament," Oral Diseases, 12(4):358-363.

Jiang et al. (2009) "Biomimetically Triggered Inorganic Crystal Transformation by Biomolecules: A New Understanding of Biomineralization," Journal of Physical Chemistry B, 113(31):10838-10844.

Kim et al. (2010) "Functional biomimetic analogs help remineralize apatite-depleted demineralized resin-infiltrated dentin via a bottom-up approach," Acta Biomaterialia, 6(7):2740-2750.

Kodaka et al. (1998) "Spherulitic brushite stones in the dental pulp of a cow," Journal of Electron Microscopy, 47(1):57-65.

Laksminarayanan et al. (2010) "Perturbed Amelogenin Secondary Structure Leads to Uncontrolled Aggregation in Amelogenesis Imperfecta Mutant Proteins," Journal of Biological Chemistry, 285(52):40593-40603.

LeNorcy et al. (2011) "Potential Role of the Amelogenin N-Terminus in the Regulation of Calcium Phosphate Formation in vitro," Cells Tissues Organs, 194(2-4):188-193.

Liu et al. (2008) "Improving the accuracy of template-based predictions by mixing and matching between initial models," BMC Structural Biology, 8(24):1-10.

Lowenstam (1981) "Minerals Formed by Organisms," Science, 211(4487):1126-1131.

Zhang et al. (2007) "'Magic bullets' for bone disease: progress in rational design of bone-seeking medicinal agents," Chemical Society Reviews, 36(3):507-531.

Margolis et al. (2006) "Role of Macromolecular Assembly of Enamel Matrix Proteins in Enamel Formation," Journal of Dental Research, 85(9):775-793.

Masica and J.J. Gray (2009) "Solution- and Adsorbed-State Structural Ensembles Predicted for the Statherin-Hydroxyapatite System," Biophysical Journal, 96(8):3082-3091.

Meyer and C.C. Weatherall (1982) "Amorphous to Crystalline Calcium Phosphate Phase Transformation at Elevated pH," Journal of Colloid and Interface Science, 89(1):257-267.

Moradian-Oldak et al. (2000) "Carboxy- and Amino-Terminal Domains of Amelogenin are Involved in the Supramolecular Self-assembly," Journal of Dental Research (Abstracts of Papers), 79:513-513.

Moradian-Oldak et al. (2000) "Self-Assembly Properties of Recombinant Engineered Amelogenin Proteins Analyzed by Dynamic Light Scattering and Atomic Force Microscopy," Journal of Structural Biology, 131(1):27-37.

Nagatomo et al. (2006) "Stem cell properties of human periodontal ligament cells," Journal of Periodontal Research, 41(4):303-310.

Paine et al. (2000) "Enamel Biomineralization Defects Result from Alterations to Amelogenin Self-Assembly," Journal of Structural Biology, 132(3):191-200.

(56) References Cited

OTHER PUBLICATIONS

Paine et al. (2001) "Regulated gene expression dictates enamel structure and tooth function," Matrix Biology, 20 (5-6)273-292.
Friddle, et al., "Single Molecule Determination of the Face-Specific adsorption of amelogenin's C-Terminus on Hydroxyapatite," Angewandte Chemie. International Edition, 2011, vol. 50,pp. 7541-7545, Published online: Jun. 27, 2011.
Le, et al., "Comparative calcium binding of leucine-rich amelogenin peptide and full-length amelogenin," European Journal of Oral Sciences, 2006, vol. 114, Supplement 1, pp. 320-326.
Borger, et al., "Influence of Remineralizing Gels on Bleached Enamel Microhardness in Different Time Intervals, " Operative Dentistry, 35-2: 180-186, 2010.
Brunton, et al., "treatment of early caries lesions using biomimetic self-assembling peptides—A clinical safety trail," British Dental Journal, 215:E6, 2013.
Li, "tooth Color Measurement Using Chroma Meter: Techniques, Advantages, and Disadvantages," J Esthet Restor Dent, 15:S33-S41, 2003.
Lin, et al., "Evalutation of the Effect of Laser Tooth Whitening," Int J Prosthodont, 21(5):415-418, 2008.
International Search Report and Written Opinion PCT/US2016/13301, dated Jul. 8, 2016.
Addy (Oct. 2002) "Dentine hypersensitivity: new perspectives on an old problem," International Dental Journal, 52(S5P2):367-375.
Al-Hiyasat et al. (Jul.-Aug. 1998) "Investigation of human enamel wear against four dental ceramics and gold," Journal of Dentistry, 26(5-6):487-495.
Al-Qunaian (Mar.-Apr. 2005) "The effect of whitening agents on caries susceptibility of human enamel," Operative Dentistry, 30(2):265-270.
Arslan et al. (May 2008) "Mechanical properties and biocompatibility of plasma-nitrided laser-cut 316L cardiovascular stents," Journal of Materials Science—Materials in Medicine, 19(5):2079-2086.
Attin et al. (Sep. 2007) "Potential of fluoridated carbamide peroxide gels to support post-bleaching enamel re-hardening." Journal of Dentistry, 35(9):755-759.
Baldwin et al. (Jun. 2008) "Activation time and material stiffness of sequential removable orthodontic appliances. Part.3: Premolar extraction patients," American Journal of Orthodontics and Dentofacial Orthopedics, 133(6):837-845.
Bardow et al. (May 2001) "Relationships between medication intake, complaints of dry mouth, salivary flow rate and composition, and the rate of tooth demineralization in situ," Archives of Oral Biology, 46(5) 413-423.
Bartlett et al. (Aug. 1996) "A study of the association between gastro-oesophageal reflux and palatal dental erosion," British Dental Journal, 181(4):125-131.
Boersma et al. (Jan.-Feb. 2005) "Caries prevalence measured with QLF after treatment with fixed orthodontic appliances: Influencing factors," Caries Research, 39(1):41-47.
Bollen et al. (Apr. 2008) "The effects of orthodontic therapy on periodontal health: a systematic review of controlled evidence," Journal of the American Dental Association, 139(4):413-422.
Bollen et al. (Nov. 2003) Sequential removable orthodontic appliances, activation time and material stiffness—Part I: Ability to complete treatment, American Journal of Orthodontics and Dentofacial Orthopedics, 124(5):496-501.
Borjian et al. (2010; retrieved Oct. 2015) "Pop-Cola Acids and Tooth Erosion: An In Vitro, In Vivo, Electron-Microscopic, and Clinical Report," International Journal of Dentistry, 2010(Article ID 957842):1-12.
Boyaci et al. (Feb. 2007) "Statistical modelling of beta-galactosidase inhibition during lactose hydrolysis," Food Microbiology, 20(1):79-91.
Braun et al. (2002) "Genetically engineered gold-binding polypeptides: structure prediction and molecular dynamics," Journal of Biomaterials Science Polymer Edition, 13(7):747-757.

Brown et al. (Jun. 2000) "A genetic analysis of crystal growth," Journal of Molecular Biology, 299(3):725-735.
Burbridge et al. (Nov. 2006) "A randomized controlled trial of the effectiveness of a one-step conditioning agent in sealant placement: 6-month results," International Journal of Paediatric Dentistry, 16(6):424-430.
Cetinel et al. (Feb. 2013) "Addressable self-immobilization of lactate dehydrogenase across multiple length scales," Biotechnology Journal, 8(2):262-272.
Chen et al. (Jun. 2010) "Systematic review of self-ligating brackets," American Journal of Orthodontics and Dentofacial Orthopedics, 137(6): 26.e1-726.e18; discussion 726-727.
Chu et al. (Jul. 2010) "Ablation of systemic phosphate-regulating gene fibroblast growth factor 23 (Fgf23) compromises the dentoalveolar complex," The Anatomical Record, 293(7):1214-1226.
Clements et al. (Nov. 2003) "Activation Time and Material Stiffness of Sequential Removable Orthodontic Appliances. Part II: Dental Improvements," American Journal of Orthodontics and Dentofacial Orthopedics, 124(5):502-508.
Connolly et al. (May 2002) "A custom mandibular distraction device for the rat," Journal of Craniofacial Surgery, 13(3):445-452.
Cunha-Cruz et al. (Sep. 2010) "Treating dentin hypersensitivity: therapeutic choices made by dentists of the Northwest PRECEDENT network," Journal of the American Dental Association, 141(9):1097-1105.
Dababneh et al. (Dec. 1999) "Dentine hypersensitivity—an enigma? A review of terminology, epidemiology, mechanisms, aetiology and management," British Dental Journal, 187(11):606-611.
Dai et al. (Nov. 2005) "Nonequilibrium Synthesis and Assembly of Hybrid Inorganic-Protein Nanostructures using an Engineered DNA Binding Protein," Journal of the American Chemical Society, 127(44):15637-15643.
Demir et al. (Apr. 2011) "Spatially Selective Assembly of Quantum Dot Light Emitters in an LED Using Engineered Peptides," ACS Nano, 5(4):2735-2741.
Donatan et al. (Jan. 2009) "Physical elution in phage display selection of inorganic-binding peptides," Materials Science and Engineering: C, 29(1):14-19.
Erdag et al. (Nov.-Dec. 2011) "Identification of novel neutralizing single-chain antibodies against vascular endothelial growth factor receptor 2," Biotechnology and Applied Biochemistry, 58(6):412-422.
Evans et al. (May 2008) "Molecular Design of Inorganic-Binding Polypeptides," MRS Bulletin, 33(5):514-518.
Featherstone (Jul. 2000) "The science and practice of caries prevention," Journal of the American Dental Association, 131(7): 887-899.
Flaitz and MJ Hicks (Jul.-Aug. 1996) "Effects of carbamide peroxide whitening agents on enamel surfaces and caries-like lesion formation: An SEM and polarized light microscopic in vitro study," ASDC Journal of Dentistry for Children, 63(4):249-256.
Fong et al. (Aug. 2009) "Aberrant Cementum Phenotype Associated with the Hypophosphatemic Hyp Mouse," Journal of Periodontology, 80(8):1348-1354.
Fong et al. (Dec. 1999) "Nano-mechanical properties profiles across dentin-enamel junction of human incisor teeth," Materials Science and Engineering: C, 7(2):119-128.
Fong et al. (Jun. 2009) "Structure and Mechanical Properties of Ank/Ank Mutant Mouse Dental Tissues—an Animal Model for Studying Periodontal Regeneration," Archives of Oral Biology, 54(6):570-576.
Fong et al. (May 2005) "The Crowning Achievement: Gelling to the Root of the Problem," Journal of Dental Education . 69(5):555-570.
Foster et al. (2011) "The Progressive Ankylosis Protein Regulates Cementum Apposition and Extracellular Matrix Composition," Cells Tissues Organs, 194(5):382-405.
Greenlee et al. (Feb. 20110 "Stability of treatment for anterior open-bite malocclusion: a meta-analysis," American Journal of Orthodontics and Dentofacial Orthopedics, 139(2):154-169.
Gunduz et al. (Feb. 2012) "Bioinspired bubble design for particle generation," Journal of the Royal Society: Interface, 9(67):389-395.

(56) References Cited

OTHER PUBLICATIONS

Hnilova et al. (Feb. 2012) "Peptide-Directed Co-Assembly of Nanoprobes on Multimaterial Patterned Solid Surfaces," Soft Matter, 8(16):4327-4334.
Hnilova et al. (Jan. 2012) "Single-Step Fabrication of Patterned Gold Film Array by an Engineered Multi-Functional Peptide," Journal of Colloid and Interface Science, 365(1):97-102.
Hnilova et al. (May 2012) "Fabrication of Hierarchical Hybrid Structures using Bio-enabled Layer-by-Layer Self-Assembly," Biotechnology and Bioengineering, 109(5)1120-1130.
Hnilova et al. (Nov. 2008) "Effect of Molecular Conformations on the Adsorption Behavior of Gold-Binding Peptides," Langmuir, 24(21)12440-12445.
Hobson et al. (Spring 2008) "Patterns of dental care utilization among patients with temporomandibular disorders," Journal of Orofacial Pain, 22(2):108-114.
Honda et al. (Dec. 2008) Tooth-forming potential in embryonic and postnatal tooth bud cells, Medical Molecular Morphology, 41(4):183-192.
Huang (Sep. 2002) "Long-term stability of anterior open-bite therapy: a review," Seminars in Orthodontics. 8(3)162-172.
Huang (Sep. 2005) "Functional appliances and long-term effects on mandibular growth," American Journal of Orthodontics and Dentofacial Orthopedics, 128(3):271-272.
Huang and K-J Soderholm (Feb. 1989) "In vitro investigation of shear bond strength of a phosphate based dentinal bonding agent," Scandinavian Journal of Dental Research, 97(1):84-92.
Huang and Ma del Aguila (Oct. 2003) "The distribution of orthodontic services and fees in an insured population in Washington," American Journal of Orthodontics and Dentofacial Orthopedics, 124(4):366-372.
Huang and TC Rue (Nov. 2006) "Third-molar extraction as a risk factor for temporomandibular disorder," Journal of the American Dental Association, 137(11):1547-1554.
Huang et al. (Apr. 2002) "Risk factors for diagnostic subgroups of painful temporonnandibular disorders (TMD)," Journal of Dental Research, 81(4):284-288.
Huang et al. (Jan. 2013) "Effectiveness of MI Paste Plus and PreviDent fluoride varnish for treatment of white spot lesions: a randomized controlled trial," American Journal of Orthodontics and Dentofacial Orthopedics, 143:31-41.
Arends, J., et al., Remineralization of Human Dentin in vitro. Caries Research, 1990. 24(6): p. 432-435.
Balbus, J.M. and M.E. Lang, Is the water safe for my baby? Pediatric Clinics of North America, 2001. 48(5): p. 1129.
Brown, W.E, et al., Crystallographic and Chemical Relations between Octacalcium Phosphate and Hydroxyapatite. Nature, 1962. 196(4859): p. 1050.
Cargill, J.S. and M. Upton, The effect of *Staphylococcus epidermidis* culture supernatants on the biofilm density of other 5-epidermidis strains. International Journal of Antimicrobial Agents, 2007. 29: p. 5144-5145.
Fawell, J., et al., Fluoride in Drinking-water, 2006, London: World Health Organization.
Gungormus, M., et al., Regulation of in vitro calcium phosphate mineralization by combinatorially selected hydroxyapatite-binding peptides. Biomacromolecules, 2008. 9(3): p. 966-973.
Ingram, A.E., J. Robinson, and R.J. Rohrich, The antibacterial effect of porous hydroxyapatite granules. Plastic and Reconstructive Surgery, 1996. 98(6): p. 1119-1119.
Jenkinson, H.F. and D.R. Demuth, Structure, function and immunogenicity of streptococcal antigen 1/11 polypeptides. Molecular Microbiology, 1997. 23(2): p. 183-190.
Kawasaki, K., et al., Relationship between mineral distributions in dentine lesions and subsequent remineralization in vitro. Caries Research, 2000. 34(5): p. 395-403.
Klem, M.T., et al., Bio-inspired synthesis of protein-encapsulated CoPt nanoparticles. Advanced Functional Materials, 2005. 15(9): p. 1489-1494.
Liu, T. and R.J. Gibbons, Binding of *Streptococci* of the Mutans Group to Type-1 Collagen Associated With Apatitic Surfaces. Oral Microbiology and Immunology, 1990. 5(3): p. 131-136.
Michelich, V.J., G.S. Schuster, and D.H. Pashley, Bacterial Penetration of Human-Dentin Invitro. Journal of Dental Research, 1980. 59(8): p. 1398-1403.
Miller, W.O., The Microorganisms of the Human Mouth. The American Journal of the Medical Sciences, 1891. 101 (2): p. 159.
Oren, E.E., et al., "A novel knowledge-based approach to design inorganic-binding peptides" Bioinformatics, 2007. 23(21): p. 2816-2822.
Owadally, I.D., et al., Biological properties of IRM with the addition of hydroxyapatite as a retrograde root filling material. Endodontics & Dental Traumatology, 1994. 10(5): p. 228-232.
Patel, J.D., et al., 5-epidermidis biofilm formation: Effects of biomaterial surface chemistry and serum proteins. Journal of Biomedical Materials Research Part A, 2007. 80A(3): p. 742-751.
Sarikaya, M., et al., Molecular biomimetics: nanotechnology through biology. Nature Materials, 2003.2(9): p. 577-585.
Gungormus, et al. (2012) "Cementomimetics—constructing a cementum-like biomineralized microlayer via amelogenin-derived peptides," International Journal of Oral Science, 4(2): 69-77.
Tin-Oo, M.M., et al., Antibacterial property of locally produced hydroxyapatite Archives of Orofacial Sciences, 2007. 2: p. 41-44.
Tamerler, C., et al., Molecular biomimetics: GEPI-based biological routes to technology. Biopolymers, 2010. 94(1): p. 78-94.
Tamerler, C. and M. Sarikaya, Genetically Designed Peptide-Based Molecular Materials. Acs Nano, 2009. 3(7): p. 1606-1615.
Torabinejad, M., et al., Physical and Chemical-Properties of a New Root-End Filling Material. Journal of Endodontics, 1995.21(7): p. 349-353.
Vallet-Regi, M., C.V. Ragel, and A.J. Salinas, Glasses with medical applications. European Journal of Inorganic Chemistry, 2003(6): p. 1029-1042.
Vojinovi.O, H. Nyborg, and Brannstr.M, Acid Treatment of Cavities Under Resin Fillings—Bacterial Growth in Dentinal Tubules and Pulpal Reactions. Journal of Dental Research, 1973. 52(6): p. 1189-1193.
Wilson, A.D. and B.E. Kent, Glass-Ionomer Cement, a New Translucent Dental Filling Material. Journal of Applied Chemistry and Biotechnology, 1971. 21(11): p. 313.
International Search Report for PCT/US2012/039650, dated Sep. 11, 2012.
Friddle, et al., (2011) "Single-Molecule Determination of the Face-specific Adsorption of Amelogenin's C-terminus on Hydroxyapatite," Angewandte Chemie International Edition, 50(33): 7541-7545.
Fong, et al. (2003) "ENamle Structure Properties Controlled by Engineered Proteins in Transgenic Mice," Jounral of Bone and Mineral Research, 18(11): 2052-2059.
Zhang, et al. (2010) "Full length amelogenin binds to cell surface LAMP-1 on tooth root/periodontium associated cells," Archives of Oral Biology, 55(6): 417-425.
Delgado, et al. (2008) "Amelogenin, the major protein of tooth enamel: A new phylogenetic marker for ordinal mammal relationships," Molecular Phylogenetics and Evolution, 47(2): 865-869.
Sebastiano Collino, (May 2008) "Inorganic Crystal Formation Directed by Biomineral Proteins: Characterization and Biophysical Strudies of Mollusk-Nacre and Tooth-Enamel Polypeptide Sequences" A dissertation submitted in partial fulfillment of the requirements for the degree of Doctor of philosophy Department of Chemistry New York University, UMI No. 3320769, 303 pages.
Ram Samudrala, Associate professor at the University of Washington, (Apr. 21, 2007), "Computational Engineering of Bionanostructures" 22 pages.
Gungormus, (Jun. 2012) International Journal of Oral Science, "Cementomimetics—constructing a cementum-like biomineralized microlayer via amelogenin-derived peptides" vol. 4 (2) pp. 12 pages.
Water is natural product, from http://www.biology-online.org/dictionary/Water, pp. 1-3. Accessed Apr. 24, 2014.

(56) References Cited

OTHER PUBLICATIONS

Valinoti et al. (Mar. 2011) "In vitro alterations in dental enamel exposed to acidic medicines," International Journal of Paediatric Dentistry, 21(2):141-150.
Wacker et al. (Dec. 2004) "Hsp70 and Hsp40 attenuate formation of spherical and annular polyglutamine oligomers by partitioning monomer," Nature Structural and Molecular Biology, 11(12)1215-1222.
Watari (Jun. 2005) "In situ quantitative analysis of etching process of human teeth by atomic force microscopy," Journal of Electron Microscopy, 54(3):299-308.
Watts and M. Addy (Mar. 2001) "Tooth discolouration and staining: a review of the literature," British Dental Journal, 190(6):309-316.
Wei et al. (Mar. 2009) "Nanopatterning bi-Functional Peptides for Templated Assembly," Small, 5(6):689-693.
Wright (Oct. 1969) "The abrasive wear resistance of human dental tissues," Wear, 14(4):263-284.
Yazici et al. (Feb. 2013) "Biological Response on a Titanium Implant-Grade Surface Functionalized with modular peptides," Acta Biomaterialia, 9(2):5341-5352.
Yousefzadeh et al. (Feb. 2010) "Cephalometric and Electromyographic Study of Patients of East-African Ethnicity With and Without Anterior Open Bite," American Journal of Orthodontics and Dentofacial Orthopedics, 137(2):236-246.
Yuca et al' (May 2011)In vitro labeling of hydroxyapatite minerals by an engineered protein, Biotechnology & Bioengineering, 108(5)1021-1030.
Zhang et al. (2007; retrieved Oct. 2015) "Chapter 72: Periodontal-Tissue Engineering," in Principles of Tissues Engineering, 3rd Edition, Lanza et al. (Eds.), Elsevier London, UK, pp. 1095-1109.
Zin et al. (2007; Oct. 2015) "Peptide-mediated surface-immobilized quantum dot hybrid nanoassemblies with controlled photoluminescence," Journal of Materials Chemistry, 17(9):866-872.
Zuroff et al. (Mar. 2010) "Orthodontic Treatment of Anterior Open-bite Malocclusion: Stability 10 years Postretention," American Journal of Orthodontics and Dentofacial Orthopedics, 137(3):302.e1-8; discussion 302-3.
Paine et al. (2003) "Functional Domains for Amelogenin Revealed by Compound Genetic Defects," Journal of Bone and Mineral Research, 18(3):466-472.
Pampena et al. (2004) "Inhibition of hydroxyapatite formation by osteopontin phosphopeptides," Biochemical Journal, 378:1083-1087.
Pathak et al. (1992) Histidine-rich calcium binding protein, a sarcoplasmic reticulum protein of striated muscle, is also abundant in arteriolar smooth muscle cells, Journal of Muscle Research and Cell Motility, 13(3):366-376.
Pugach et al. (2010) "The Amelogenin C-Terminus is Required for Enamel Development," Journal of Dental Research, 89(2):165-169.
Qiu et al. (2004) "Molecular modulation of calcium oxalate crystallization by osteopontin and citrate," Proceedings of the National Academy of Sciences USA, 101(7):1811-1815.
Samudrala and J. Moult (1998) "An All-atom Distance-dependent Conditional Probability Discriminatory Function for Protein Structure Prediction," Journal of Molecular Biology, 275(5):895-916.
Samudrala et al. (1999) "Ab Initio Protein Structure Prediction Using a Combined Hierarchical Approach," PROTEINS: Structure, Function, and Genetics, Suppl. 3:194-198.
Sarikaya et al. (1995) "Nacre: Properties, Crystallography, Morphology, and Formation," in Biomimetics: design and processing of materials, M. Sarikaya and I.A. Aksay (Eds.), AIP Press: Woodbury, NY, pp. 35-90.
Seo et al. (2004) "Investigation of multipotent postnatal stem cells from human periodontal ligament," Lancet, 364 (9429)149-155.
Seo et al. (2005) "Recovery of Stem Cells from Cryopreserved Periodontal Ligament," Journal of Dental Research, 84 (10):907-912.

Shaw et al. (2004) "The COOH Terminus of the Amelogenin, LRAP, Is Oriented Next to the Hydroxyapatite Surface," Journal of Biological Chemistry, 279(39):40263-40266.
Snead (2003) "Amelogenin Protein Exhibits a Modular Design: Implications for Form and Function," Connective Tissue Research, 44(Suppl. 1):47-51.
Snead (2006) "Protein self-assembly creates a nanoscale device for biomineralization," Materials Science and Engineering C—Biomimetic and Supramolecular Systems, 26(8):1296-1300.
So et al. (2009) "Adsorption, Diffusion, and Self-Assembly of an Engineered Gold-Binding Peptide on Au(111) Investigated by Atomic Force Microscopy," Angewandte Chemie—International Edition, 48(28):5174-5177.
Taller et al. (2007) "Specific Adsorption of Osteopontin and Synthetic Polypeptides to Calcium Oxalate Monohydrate Crystals," Biophysical Journal, 93(5)1768-1777.
Tamerler and M. Sarikaya (2006) "Engineered Inorganic-Binding Polypeptides for Bionanotechnology," in BioMEMS and Biomedical Nanotechnology, vol. I: Biological and Biomedical Nanotechnology, eds. M. Ferrari et al., Springer, pp. 307-326.
Tamerler and M. Sarikaya (2006) "Molecular Biomimetics: Building Materials Nature's Way, One Molecule at a Time," in Nanofabrication Towards Biomedical Applications: Techniques, Tools, Applications, and Impact, eds. C.S.S.R. Kumar et al., John Wiley & Sons, pp. 119-134.
Tamerler and M. Sarikaya (2008) "Molecular Biomimetics: Genetic Synthesis, Assembly, and Formation of Materials Using Peptides," MRS Bulletin, 33(5):504-512.
Tamerler and M. Sarikaya (2009) "Molecular biomimetics: nanotechnology and bionanotechnology using genetically engineered peptides," Philosophical Transactions of the Royal Society A, 367(1894):1705-1726.
Taubman et al. (2005) "Immune Response: The Key to Bone Resorption in Periodontal Disease," Journal of Periodontology, 76(11 (Suppl.)):2033-2041.
Tye et al. (2003) "Delineation of the Hydroxyapatite-nucleating Domains of Bone Sialoprotein," Journal of Biological Chemistry, 278(10):7949-7955.
Alang and R. Samudrala (2005) "FSSA: a novel method for identifying functional signatures from structural alignments," Bioinformatics, 21(13):2969-2977.
Wang and R. Samudrala (2006) "Incorporating background frequency improves entropy-based residue conservation measures," BMC Bioinformatics, 7(385):1-8.
Wang et al. (2008) "Protein Meta-Functional Signatures from Combining Sequence, Structure, Evolution, and Amino Acid Property Information," PLoS Computational Biology, 4(9):e1000181-1-e1000181-13.
Wazen et al. (2007) "In Vivo Functional Analysis of Polyglutamic Acid Domains in Recombinant Bone Sialoprotein," Journal of Histochemistry & Cytochemistry, 55(1):35-42.
Zhang (2007) "Template-based modeling and free modeling by I-TASSER in CASP7," PROTEINS: Structure, Function, and Bioinformatics, 69:108-117.
Seker et al. (Jul. 2007) "Adsorption behavior of linear and cyclic genetically engineered platinum binding peptides," Langmuir, 23(15):7895-7900.
Seker et al. (Mar. 2011) "Assembly Kinetics of Nanocrystals via Peptide Hybridization," Langmuir, 27(8):4867-4872.
Sills et al. (2005; retrieved Oct. 2015) "Thermal transition measurements of polymer thin films by modulated nanoindentation," Journal of Applied Physics, 98(1):014302.
So et al. (Feb. 2012) "Controlling Self Assembly of Engineered Peptides on Graphite by Rational Mutation," ACS Nano. 6(2):1648-1656.
So et al. (Jun. 2009) "Molecular Recognition and Supramolecular Self-Assembly of a Genetically Engineered Gold Binding Peptide on Au{111}," ACS Nano, 3(6):1525-1531.
St. John (Jul. 2007) "Biocompatibility of dental materials," Dental Clinics of North America, 51(3):747-760.
Struble and GJ Huang (Jan. 2010) "Comparison of Prospectively and Retrospectively Selected American Board of Orthodontics

(56) References Cited

OTHER PUBLICATIONS

Cases," American Journal of Orthodontics and Dentofacial Orthopedics, 137(1):6.e1-8; discussion 6-8.
Sulieman et al. (Aug. 2003) "Development and evaluation of a method in vitro to study the effectiveness of tooth bleaching," Journal of Dentistry, 31(6):415-422.
Sun et al. (May 2009) "Ask us. Topical fluoride treatment," American Journal of Orthodontics and Dentofacial Orthopedics, 135(5):561-563.
Suzuki et al. (Feb. 2007) "Adsorption of Genetically Engineered Proteins Studied by Time-of-Flight Secondary Ion Mass Spectrometry (TOF-SIMS). Part A: Data Acquisition and Principal Component Analysis (PCA)", Surface and Interface Analysis, 39(5):419-426.
Oren, et al., Probing the Molecular Mechanisms of Quarts-binding Pepetides, Langmuir 2010, 26(13), 11003-11009.
Tabchoury et al. (Dec. 1998) "The effects of fluoride concentration and the level of cariogenic challenge on caries development in desalivated rats," Archives of Oral Biology, 43(12):917-924.
Tamerler and M. Sarikaya (2006) "Molecular Biomimetics: Linking peptides with inorganic structures" in Microbial Bionanotechnology: Biological self-assembly systems and biopolymer-based nanostructures (Editor: Bernd Rehm), Chapter 8, pp: 191-221 (Horizon, London).
Tamerler and M. Sarikaya (May 2007) "Molecular Biomimetics: Utilizing Nature's Molecular Ways in Practical Engineering," Acta Biomaterialia, 3(3):289-299.
Tamerler et al. (Apr. 2007) "Genetically engineered polypeptides for inorganics: A utility in biological materials science and engineering," Materials Science and Engineering C, 27(3):558-564.
Tamerler et al. (Aug. 2006) "Adsorption kinetics of a gold binding peptide by SPR spectroscopy and a quartz crystal microbalance," Langmuir, 22(18):7712-7718.
Tamerler et al. (Nov. 2006) "Specificity & Directed Assembly of Gold-Binding Peptide," Small, 2(11):1372-1378.
Tamerler et al. (Sep. 2003) "Biomimetic multifunctional molecular coatings using engineered proteins," Progress in Organic Coatings, 47(3-4):267-274.
Tanzer et al. (1997; retrieved Oct. 2015) "Remineralization by a novel dentrifice," Journal of Dental Research, 76:134, abstract No. 965.
Taylor et al. (Sep. 2009) "Effects of Malocclusion and Its Treatment on the Quality of Life of Adolescents," American Journal of Orthodontics and Dentofacial Orthopedics, 136(3):382-392.
Theis et al. (Dec. 2005) "Eligibility for publicly funded orthodontic treatment determined by the handicapping labiolingual deviation index," American Journal of Orthodontics and Dentofacial Orthopedics, 128(6):708-715.
Thompson et al. (1999; retrieved Oct. 2015) "Model for assessment of carious lesion remineralization, and remineralization by a novel toothpaste," Journal of Clinical Dentistry, 10(1 Spec No):34-39.
Travess et al. (Jan. 2004) "Orthodontics. Part 6: Risks in orthodontic treatment," British Dental Journal, 196(2):71-77.
U.S. Public Health Service, Department of Health and Human Services (2000; retrieved Oct. 2015) "Oral Health in America: A Report of the Surgeon General," 332 pages.
Huang et al. (Jun. 2004) "Orthodontic care in an insured population in Washington: demographic factors," American Journal of Orthodontics and Dentofacial Orthopedics, 125(6):741-746.
Huang et al. (Mar. 2008) "Age and third molar extraction as risk factors for temporomandibular," Journal of Dental Research, 87(3):283-287.
Huang et al. (Sep. 2012) "Stability of Deep-bite Correction: a systematic review," Journal of the World Federation of Orthodonists, 1(3):e89-e96.
Huang et al. (Spring 1990) "Stability of anterior openbite treated with crib therapy," Angle Orthodontist, 60(1):17-24; discussion 25-26.
Hyde et al. (Aug. 2010) "Survey of orthodontists' attitudes and experiences regarding miniscrew implants," Journal of Clinical Orthodontics, 44(8):481-486.
Jolley et al. (Mar. 2010) "Dental effects of interceptive orthodontic treatment in a Medicaid population: interim results from a randomized clinical trial," American Journal of Orthodontics and Dentofacial Orthopedics, 137(3):324-333.
Kacar et al. (Jan. 2009) "Quartz Binding Peptides as Molecular Linkers towards Fabricating Multifunctional Micropetterned Substrates," Advanced Materials, 21(3):295-299.
Kacar et al. (Jul. 2009) "Directed Self-Immobilization of Alkaline Phosphatase on Micro-patterned Substrates via Genetically Fused Metal-Binding Peptide," Biotechnology and Bioengineering, 103(4):696-705.
Kepenek et al. (2004) "Photoc,atalytic Bactericidal Effect of $TiO_2$ Thin Film Produced by Cathodic Arc Deposition Method," Key Engineering Materials, 254-256:463-466.
Keyes and KL Shourie (Apr. 1949) "Dental Caries in the Syrian Hamster: V. The Effect of Three Different Fluoride Compounds on Caries Activity," Journal of Dental Research, 28(2):138-143.
Khan et al. (Apr. 1998) "Dental erosion and bruxism: A tooth wear analysis from South East Queensland," Australian Dental Journal, 43(2):117-127.
Khatayevich et al. (Dec. 2010) "Biofunctionalization of Materials for Implants Using Engineered Peptides," Acta Biomaterialia, 6(12):4634-4641.
Khatayevich et al. (Jun. 2012) "Controlling the Surface Chemistry of Graphite by Engineered Self-Assembled Peptides," Langmuir, 28(23):8589-8593.
Kim et al. (Feb. 2008) "A comparison of miniplates and teeth for orthodontic anchorage," American Journal of Orthodontics and Dentofacial Orthopedics, 133(2):189.e1-9.
King et al. (Apr. 2003) "Effect of distraction rate and consolidation period on bone density following mandibular osteodistraction in rats," Archives of Oral Biology, 48(4):299-308.
King et al. (Jul. 2012) Randomized clinical trial of interceptive and comprehensive orthodontics, Journal of Dental Research, 91(7 Suppl):59S-64S.
King et al. (Spring 2012) "Medicaid and privately financed orthodontic patients have similar occlusal and psychosocial outcomes," Journal of Public Health Dentistry, 72(2):94-103.
Koray Yesiladali et al. (Oct. 2006) "Bioremediation of textile azo dyes by Trichophyton rubrum LSK-27," World Journal of Microbiology and Biotechnology, 22(10)1027-1031.
Kortelainen and M. Larmas (Feb. 1993) "Effect of fluoride on caries progression and dentin apposition in rats fed on a cariogenic or non-cariogenic diet," Scandinavian Journal of Dental Research, 101(1):16-20.
Kulp III et al. (Apr. 2004) Molecular Characterization of a prokaryotic polypeptide sequence that catalyzes Au crystal formation, Journal of Materials Chemistry, 14(14):2325-2332.
Larson et al. (1976: retrieved Oct. 2015) "Collaborative evaluation of a rat caries model in six laboratories." Journal of Dental Research, 55:8224, abstract No. 650.
Lee et al. (Jan. 2012) "Direct Interaction of Ligand-Receptor Pairs Specifying Stomatal Patterning," Genes & Development, 26(2):126-136.
LeResche et al. (Jun. 2007) "Predictors of onset of facial pain and temporomandibular disorders in early adolescence," Pain, 129(3)269-278.
Lovrov (Sep. 2007) "Enamel Demineralization during Fixed Orthodontic Treatment—Incidence and Correlation to Various Oral-hygiene Parameters," Journal of Orofacial Orthopedics, 68(5):353-363.
Lowenstam and S. Weiner (1989; retrieved Oct. 2015) On Biomineralization, Oxford University Press: New York, pp. 29-30, 147-148, 175-188.
Lynch and A. Baysan (2001; retrieved Oct. 2015) "Reversal of primary root caries using a dentifrice with a high fluoride content," Caries Research, 35(Suppl 1):60-64.
Marshall et al. (Aug. 2010) Ask Us: Self-ligating bracket claims, American Journal of Orthodontics and Dentofacial Orthopedics, 138(2):128-131.

(56) References Cited

OTHER PUBLICATIONS

Marshall et al. (Jun. 2008) "Ask us. Long-term stability of maxillary expansion," American Journal of Orthodontics and Dentofacial Orthopedics, 133(6):780-781.
Mirabelli et al. (May 2005) "Effectiveness of phase I orthodontic treatment in a Medicaid population," American Journal of Orthodontics and Dentofacial Orthopedics, 127(5):592-598.
Murrell et al. (Apr. 1979) "A Rat Ganes Model for the Evaluation of Topically Applies Fluorides." Journal of Dental Research, 58:1228, abstract No. 32.
Navia and H. Lopez (Mar. 1977) "Sources of variability in rat caries studies: weaning age and diet fed during tooth eruption," Journal of Dental Research, 56(3):222-227.
Nett and GJ Huang (Apr. 2005) "Long-term posttreatment changes measured by the American Board of Orthodontics objective grading system," American Journal of Orthodontics and Dentofacial Orthopedics, 127(4):444-450.
Noxon et al. (Nov. 2001) "Osteoclast clearance from periodontal tissues during orthodontic tooth movement," American Journal of Orthodontics and Dentofacial Orthopedics, 120(5):466-476.
Oren et al. (Mar. 2005) "Metal Recognition of Septapeptides via Polypod Molecular Architecture," Nano Letters, 5(3):415-419.
Ormiston et al. (Nov. 2005) "Retrospective analysis of long-term stable and unstable orthodontic treatment outcomes," American Journal of Orthodontics and Dentofacial Orthopedics, 128(5):568-574.
Orsini et al. (Sep. 2006) "Methods to evaluate profile preferences for the anteroposterior position of the mandible," American Journal of Orthodontics and Dentofacial Orthopedics, 130(3):283-291.
O'Sullivan and ME Curzon (May-Jun. 2000) "A comparison of acidic dietary factors in children with and without dental erosion," ASDC Journal of Dentistry for Children, 67(3):186-192.
Pang et al. (Aug. 2002) "Outcomes of planned home births in Washington State: 1989-1996," Obstetrics and Gynecology, 100(2):253-259.
Patel et al. (May 2008) "An in vitro comparison of tooth whitening techniques on natural tooth colour," British Dental Journal, 204(9):E15; discussion 516-517.
Pithon et al. (May 2012) "Effect of 10% papain gel on enamel deproteinization before bonding procedure," Angle Orthodontist, 82(3):541-545.
Pojaritskaia (1998; retrieved Oct. 2015) "Xerostomia and caries," Journal of Dental Research, 77:981, Abstract No. 2797.
Reynolds et al. (Apr. 2008) "Fluoride and casein phosphopeptide-amorphous calcium phosphate," Journal of Dental Research, 87(4):344-348.
Rosen and JS Bright (1978; retrieved Oct. 2015) "Development of an Animal Caries Model Using Adolescent Rats." Journal of Dental Research, 57:232, abstract No. 632.
Sarikaya (Dec. 1999) "Biomimetics: Materials fabrication through Biology," Proceedings of the National Academy of Sciences USA, 96(25)14183-14185.
Sarikaya et al. (2001; epub Jan. 2011) "Biomimetic model of a sponge-spicular optical fiber—mechanical properties and structure," Journal of Materials Research, 16(5):1420-1428.
Sarikaya et al. (Aug. 2004) "Materials Assembly and Formation Using Engineered Polypeptides," Annual Review of Materials Research, 34:373-408.
Schroeder et al. (Jun. 1995) "Dental erosion and acid reflux disease," Annals of Internal Medicine, 122(11):809-815.
Sedlak et al. (Jan. 2012) An engineered *Escherichia coil* silver-binding periplasmic protein promotes silver tolerance, Applied and Environmental Microbiology, 78(7):2289-2296.
Sedlak et al. (Oct. 2010) "An engineered DNA-binding protein self-assembles metallic nanostructures," ChemBioChem, 11(15):2108-2112.
Seker et al. (Dec. 2008) "Quantitative Affinity of Repeating Polypeptides to Inorganic Surfaces," Biomacromolecules, 10(2):250-257.

ten Cate, et al., "Remineralization of artificial enamel lesions in vitro. II. Determination of activation energy and reaction order," Caries Research, vol. 12, No. 4, pp. 213-222, 1978.
Twetman, et al., "Caries-preventive effect of fluoride toothpaste: a systematic review," Acta Odontologica Scandinavica, vol. 61, No. 6, pp. 347-355, 2003.
Vanichvatana, et al, "Efficacy of two calcium phosphate pastes on the remineralization of artificial caries: a randomized controlled double-blind in situ study," International Journal of Oral Science, vol. 5, No. 4, pp. 224-228, 2013.
Wefel, et al., "Development of an intra-oral single-section remineralization model," Journal of Dental Research, vol. 66, No. 9, pp. 1485-1489, 1987.
Wefel, et al., "The use of saturated DCPD in remineralization of artificial caries lesions in vitro," Journal of Dental Research, vol. 66, No. 11, pp. 1640-1643, 1987.
Wong, et al., "Cochrane reviews on the benefits/risks of fluoride toothpastes," Journal of Dental Research, vol. 90, No. 5, pp. 573-579, 2011.
Wu, et al., "Hydroxyapatite-anchored dendrimer for in situ remineralization of human tooth enamel," Biomaterials, vol. 34, No. 21, pp. 5036-5047, 2013.
Yamagishi et al., "Materials chemistry: a synthetic enamel for rapid tooth repair," Nature, vol. 433, No. 7028, 819, 2005.
Al-Mullahi, et al., "Effect of slow-release fluoride devices and casein phosphopeptide/amorphous calcium phosphate nanocomplexes on enamel remineralization in vitro," Journal of the American Dental Association, vol. 44 No. 4, pp. 364-371, 2010.
American Dental Association Council on Scientific Affairs, "Professionally applied topical fluoride: Evidence-based clinical recommendations," Journal of the American Dental Association, vol. 137, No. 8, pp. 1151-1159, 2006.
Ammari, et al., "Systematic review of studies comparing the anticaries efficacy of children's toothpaste containing 600 ppm of fluoride or less with high fluoride toothpastes of 1,000 ppm or above," Caries Research, vol. 37, No. 2, pp. 85-92, 2003.
Aponte-Merced, et al., "Uptake of 45Ca from a topically-applied monofluorophosphate sodium fluoride calcium hydroxide dentifrice by rat enamel," Archives of Oral Biology, vol. 32, No. 1, pp. 17-20, 1987.
Balakrishnan, et al., Dental caries is a preventable infectious disease, Australian Dental Journal, vol. 45, No. 4, pp. 235-245, 2000.
Bleek, et al., "New developments in polymer-controlled, bioinspired calcium phosphate mineralization from aqueous solution," Acta Biomaterialia, vol. 9, No. 5, pp. 6283-6321, 2013.
Chen, et al., "Novel Technologies for the Prevention and Treatment of Dental Caries: a Patent Survey," Expert Opinion on Therapeutic Patents, vol. 20, No. 5, pp. 681-694, 2010.
Chen, et al., "Regeneration of Biomimetic Hydroxyapatite on Etched Human Enamel by Anionic PAMAM Template in vitro," Archives of Oral Biology, vol. 58, No. 8, pp. 975-980, 2013.
Fan, et al., "Amelogenin-Assisted Ex Vivo Remineralization of Human Enamel: Effects of Supersaturation Degree and Fluoride Concentration," Acta Biomaterialia, vol. 7, No. 5, pp. 2293-2302, 2011.
Featherstone, "The caries balance: the basis for caries management by risk assessment," Oral Health & Preventative Dentistry, vol. 2, No. 3, Suppl 1, pp. 259-264, 2004.
Fowler, et al., "Influence of surfactant assembly on the formation of calcium phosphate materials—A model for dental enamel formation," Journal of Materials Chemistry, vol. 15, No. 32, pp. 3317-3325, epub 2005.
Fullerton, et al., "Guidelines for measurement of skin colour and erythema. A report from the Standardization Group of the European Society of Contact Dermatitis," Contact Dermatitis, vol. 35, No. 1, pp. 1-10, 1996.
Gaffar, et al., "In vivo studies with a dicalcium phosphate dihydrate/MFP system for caries prevention," International Dental Journal, vol. 43, No Suppl 1, pp. 81-88, 1993.
Gallagher, et al., "Coupled Nanomechanical and Raman Microspectroscopic Investigation of Human Third Molar DEJ," Journal of Dental Biomechanics, seven pages, 2010.

(56) References Cited

OTHER PUBLICATIONS

Gorelick, et al., "Incidence of white spot formation after bonding and banding," American Journal of Orthodontics, vol. 81, No. 2, pp. 93-98, 1982.
Hoppenbrouwers, et al., "The effect of lactic and acetic acid on the formation of artificial caries lesions," Journal of Dental Research, vol. 67, No. 12, pp. 1466-1467, 1988.
Huang, et al., "Biological synthesis of tooth enamel instructed by an artificial matrix," Biomaterials, vol. 31, No. 35, pp. 9202-9211, 2010.
Huang, et al., "Combined effects of nano-hydroxyapatite and Galla chinensis on remineralisation of initial enamel lesion in vitro," Journal of Dentistry, vol. 38, No. 10, pp. 811-819, 2010.
Huang, et al., "Effect of nano-hydroxyapatite concentration on remineralization of initial enamel lesion in vitro," Biomedical Materials, vol. 4, No. 3, seven pages, 2009.
Huang, et al., "Remineralization potential of nano-hydroxyapatite on initial enamel lesions: an in vitro study," Caries Research, vol. 45, No. 5, pp. 460-468, 2011.
Ieong, et al., "Possibilities and Potential Roles of the Functional Peptides Based on Enamel Matrix Proteins in Promoting the Remineralization of Initial Enamel Caries," Medical Hypotheses, vol. 76, No. 3, pp. 391-394, 2011.
Iijima, et al., "Acid resistance of enamel subsurface lesions remineralized by a sugar-free chewing gum containing casein phosphopeptide-amorphous calcium phosphate," Caries Research, vol. 38, No. 6, pp. 551-556, 2004.
Iijima, et al., "In vitro remineralization of in vivo and in vitro formed enamel lesions," Caries Research, vol. 33, No. 3, pp. 206-213, 1999.
Ingram, et al., "A chemical and histological study of artificial caries in human dental enamel in vitro," Caries Research, vol. 15, No. 5, pp. 393-398, 1981.
Kirkham, et al., "Self-assembling peptide scaffolds promote enamel remineralization," Journal of Dental Research, vol. 86, No. 5, pp. 426-430, 2007.
Koulourides, et al., "Rehardening of softened enamel surfaces of human teeth by solutions of calcium phosphates," Nature, vol. 189, pp. 226-227, 1961.
Krithikadatta, et al., "Remineralisation of occlusal white spot lesion with a combination of 10% CPP-ACP and 0.2% sodium fluoride evaluated using Diagnodent: a pilot study," Oral Health & Preventative Dentistry, vol. 11, No. 2, pp. 191-196, 2013.
Li, "Tooth Color Measurement Using Chroma Meter: Techniques, Advantages, and Disadvantages," Journal of Esthetic and Restorative Dentistry, vol. 15, No. S1, pp. S33-S41, 2003.
Li, et al., "A novel self-assembled oligopeptide amphiphile for biomimetic mineralization of enamel," BMC Biotechnology, vol. 14, No. 32, 2014.
Lynch, et al., "The Effect of Lesion Characteristics at Baseline on Subsequent De- and Remineralisation Behaviour," Caries Research, vol. 40, No. 6, pp. 530-535, 2006.
Meyer-Lueckel et al. (Feb. 2015) "Remineralizing efficacy of a CPP-ACP cream on enamel caries lesions in situ," Caries Research, vol. 49, No. 1, pp. 56-62, 2015.
Nakashima, et al., "Effect of a test dentifrice containing nano-sized calcium carbonate on remineralization of enamel lesions in vitro," Journal of Oral Science, vol. 51, No. 1, pp. 69-77, 2009.
Naumova, et al., "Effects of different amine fluoride concentrations on enamel remineralization," Journal of Dentistry, vol. 40, No. 9, pp. 750-755, 2012.
Oliver, et al., "An improved technique for determining hardness and elastic modulus using load and displacement sensing indentation experiments," Journal of Materials Research, vol. 7, No. 6, pp. 1564-1583, 1992.
Petersson, et al., "Professional fluoride varnish treatment for caries control: a systematic review of clinical trials," Acta Odontologica Scandinavica, vol. 62, No. 3, pp. 170-176, 2004.
Roberts, "Role of models in assessing new agents for caries prevention—non-fluoride systems," Advances in Dental Research, vol. 9, No. 3, pp. 304-311, discussion 312-314, 1995.
Rølla, et al., "Critical Evaluation of the Composition and Use of Topical Fluorides, with Emphasis on the Role of Calcium Fluoride in Caries Inhibition," Journal of Dental Research, vol. 69, 2 Suppl, Spec No. 780-785, discussion vol. 820-823, 1990.
Ruan, et al., "An amelogenin-chitosan matrix promotes assembly of an enamel-like layer with a dense interface," Acta Biomaterialia, vol. 9, No. 7, pp. 7289-7297, 2013.
Selwitz, et al., "Dental caries," Lancet, vol. 369, No. 9555, pp. 51-59, 2007.
Shafiei, et al., "Leucine-rich amelogenin peptide (LRAP) as a surface primer for biomimetic remineralization of superficial enamel defects: An in vitro study," Scanning, vol. 37, No. 3, pp. 179-185, 2015.
Shen, et al., "Remineralization of enamel subsurface lesions by sugar-free chewing gum containing casein phosphopeptide-amorphous calcium phosphate," Journal of Dental Research, vol. 80, No. 12, pp. 2066-2070, 2001.
Silverstone, et al., "Remineralization of natural and artificial lesions in human dental enamel in vitro. Effect of calcium concentration of the calcifying fluid," Caries Research, vol. 15, No. 2, pp. 138-157, 1981.
Sitthisettapong, et al., "Effect of CPP-ACP paste on dental caries in primary teeth: a randomized trial," Journal of Dental Research, vol. 91, No. 9, pp. 847-852, 2012.
Snead, et al., "DNA sequence for cloned cDNA for murine amelogenin reveal the amino acid sequence for enamel-specific protein," Biochemical and Biophysical Research Communications, vol. 129, No. 3, pp. 812-818, 1985.
Steiner, et al., "Fluoride as an essential element in the prevention of disease," Medical Hypotheses, vol. 62, No. 5, pp. 710-717, 2004.
Sullivan, et al., "Development of an enhanced anticaries efficacy dualcomponent dentifrice containing sodium fluoride and dicalcium phosphate dehydrate," American Journal of Dentistry, vol. 14, No. 5, pp. Spec No. 3A-11A, 2001.
ten Cate, "Review on fluoride, with special emphasis on calcium fluoride mechanisms in caries prevention," European Journal of Oral Science, vol. 105, No. 5, Pt 2, pp. 461-465, 1997.
ten Cate, et al, "Remineralization of artificial enamel lesions in vitro: III. A study of the deposition mechanism," Caries Research, vol. 14, No. 6, pp. 351-358, 1980.
ten Cate, et al., "Mechanistic Aspects of the Interactions Between Fluoride and Dental Enamel," Critical Reviews in Oral Biology and Medicine, vol. 2, No. 3, pp. 283-296, 1991.
ten Cate, et al., "Remineralization of artificial enamel lesions in vitro. IV. Influence of fluorides and diphosphonates on short- and long-term reimineralization," Caries Research, vol. 15, No. 1, pp. 60-69, 1981.

* cited by examiner

REAGENTS AND METHODS FOR TREATING DENTAL DISEASE

CROSS REFERENCE

This application is a divisional of U.S. application Ser. No. 14/117,595 filed Mar. 21, 2014, which is a U.S. National filing of PCT/US2012/039650 filed May 25, 2012, which claims priority to U.S. Provisional Application Ser. Nos. 61/490,757 filed May 27, 2011; and 61/509,986 filed Jul. 20, 2011, each of which is incorporated herein by reference in its entirety.

STATEMENT OF GOVERNMENT SUPPORT

This invention was made with government support under National Science Foundation-MRSEC grant number DMR# 0520567, and under National Institute of Dental and Craniofacial Research grant numbers DE13045 and DE15109. The government has certain rights in the invention

BACKGROUND

Demineralization (loss of mineral content on the surface of tooth) is a major cause of most dental diseases. Loss of mineral can be caused by acidic diet, dry mouth, tooth whitening, abrasion and bacterial plaque formation. If left untreated, demineralization may lead to various problems from pain and sensitivity to systemic infections (e.g. heart disease) and loss of tooth. Depending on the extent of the mineral loss, several treatment options exist to arrest and/or reverse the process and to restore the teeth to proper function with aesthetic materials. In the conventional restorative treatments, the carious part is physically removed and the lost hard tissue is replaced with metal or resin based materials using inorganic adhesives. These materials, however, are usually short lived and may cause toxic products or secondary infections.

Remineralization of the early lesions is an alternative to currently employed restorative therapies. Fluoride ions have been shown to promote the remineralization of previously demineralized enamel in vitro and in situ if adequate levels of calcium and phosphate ions are available where the fluoride is applied. It has been shown; however, that prolonged exposure to fluoridated water may cause severe dental fluorosis, skeletal fluorosis, and weakened bones, and that improper implementation of fluoride can also cause acute fluoride poisoning.

SUMMARY OF THE INVENTION

In a first aspect, the present invention provides isolated amelogenin-derived polypeptides (ADPs) comprising or consisting of (a) (WP(A/S)TDKTKREEVD)$_{1-10}$ (SEQ ID NO: 1)(ADP3);

(b) (PGYIN(L/F)SY(E/A)(K/N/A)SHSQAIN(T/V)(D/A)(R/A)TA)$_{1-10}$ (SEQ ID NO: 2) (ADP5);

(c) (LPPLFSMPLSPILPELPLEAWPAT)$_{1-10}$ (SEQ ID NO: 3) (ADP6); and (d) 12-43 contiguous amino acids of (HPP(S/T)HTLQPHHH(L/I)PVVPAQ QPV(A/I)PQQPMMPVPG(H/Q)HSMTP(T/I)QH)$_{1-10}$ (SEQ ID NO: 4) (ADP7);

or functional equivalents thereof.

The inventors have discovered that amelogenin-derived polypeptides of this aspect of the invention can be used, for example, to direct dental mineralization and to treat dental disease, as discussed herein.

In a second aspect, the present invention provides recombinant fusion polypeptide, comprising (a) the ADP of any embodiment or combination of embodiments of the first aspect of the invention; and (b) a heterologous polypeptide.

In a third aspect, the present invention provides compositions, comprising (a) the ADP of any embodiment or combination of embodiments of the first aspect of the invention; and (b) a non-peptide moiety linked to the amelogenin-derived polypeptide.

In a fourth aspect, the present invention provides pharmaceutical compositions, comprising one or more polypeptides, recombinant fusion proteins, or compositions of the invention and a pharmaceutically acceptable carrier.

In a fifth aspect, the present invention provides oral care products, comprising any embodiment or combination of embodiments of the polypeptides, recombinant fusion proteins, and/or compositions of the invention.

In a sixth aspect, the present invention provides isolated nucleic acids encoding an ADP or fusion polypeptide of the present invention. In a seventh aspect, the present invention provides recombinant expression vectors comprising the isolated nucleic acid of any aspect of the invention operatively linked to a suitable control sequence. In an eighth aspect, the present invention provides host cells that have been transfected with the recombinant expression vectors disclosed herein, wherein the host cells can be either prokaryotic or eukaryotic.

In a ninth aspect, the present invention provides methods for treating dental disease, comprising administering to a subject in need thereof an amount effective to treat the dental disease of the polypeptide, recombinant fusion protein, composition, pharmaceutical composition or oral care product of any embodiment or combination of embodiments of the invention.

DETAILED DESCRIPTION OF THE INVENTION

Figure 1:
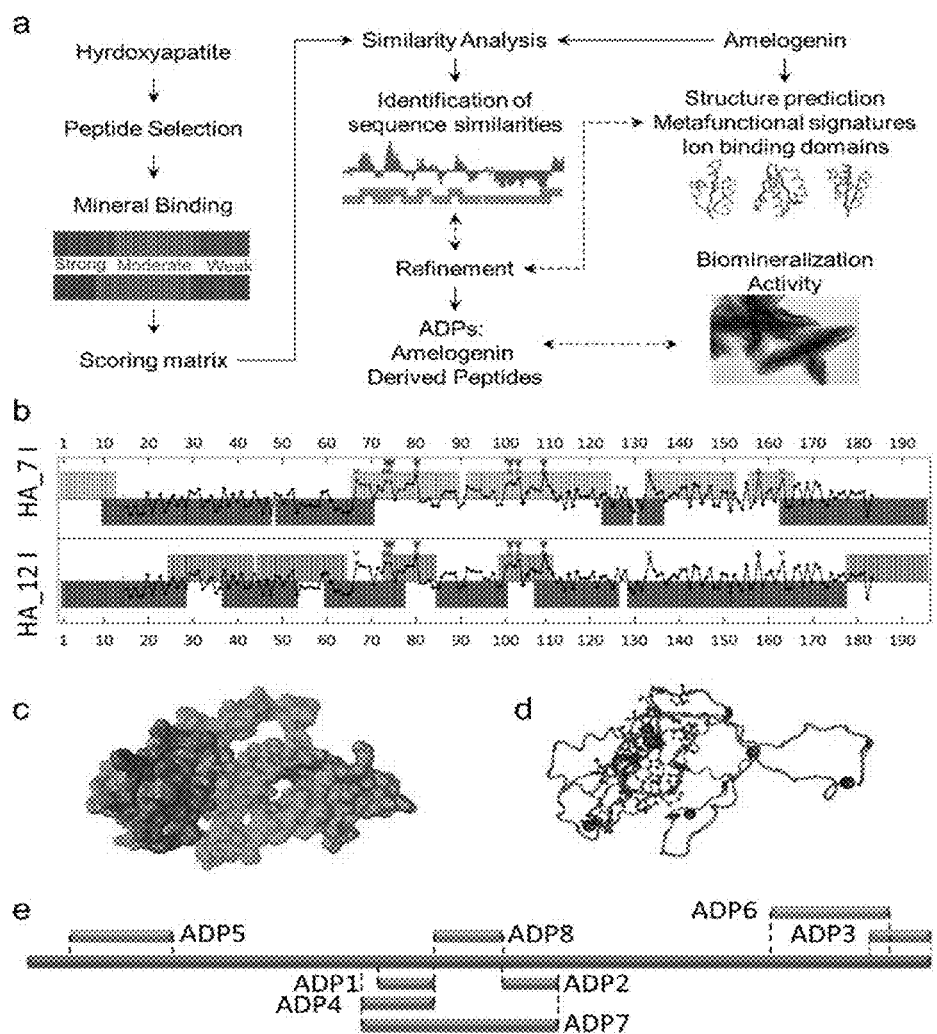
FIG. 1. Identification of amelogenin derived peptides (ADPs). Panel a, Flowchart showing the design steps for identifying the ADPs. Panel b, High and low similarity amino acid regions among the rM180 and two experimentally selected HABP sets. Each bar represents one amino acid and the amino acid domains above the baseline represent the high similarity while those below represent low similarity regions. The overlapped plot shows the potential calcium ion binding domains. Note that the majority of the highest potential domains coincide with the high similarity regions (arrow heads). Panel c, Computationally determined molecular structure for rM180 amelogenin showing position of (folded) ADP7 within rM180. Panel d, Positions of the ion-binding domains on rM180. Panel e, The locations of the ADPs along rM180.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides isolated amelogenin-derived polypeptides (ADPs) comprising or consisting of (a) (WP(A/S)TDKTKREEVD)$_{1-10}$ (SEQ ID NO: 1) (ADP3);

(b) (PGYIN(L/F)SY(E/A)(K/N/A)SHSQAIN(T/V)(D/A)(R/A)TA)$_{1-10}$ (SEQ ID NO: 2) (ADP5);

(c) (LPPLFSMPLSPILPELPLEAWPAT)$_{1-10}$ (SEQ ID NO: 3) (ADP6); and (d) 12-43 contiguous amino acids of (HPP(S/T)HTLQPHHH(L/I)PVVPAQ QPV(A/I)PQQPMMPVPG(H/Q)HSMTP(T/I)QH)$_{1-10}$ (SEQ ID NO: 4) (ADP7);

or functional equivalents thereof.

The inventors have discovered that amelogenin-derived polypeptides of this aspect of the invention can be used, for example, to direct dental mineralization and to treat dental disease, as discussed herein.

As used herein, a "functional equivalent" of a polypeptide is one that retains the biological activity of the polypeptide in treating dental disease, and included one or more amino acid substitutions, deletions, additions, or insertions. In various embodiments, the functional equivalent is at least 50%, 55%, 60%, 65%, 70%, 75%, 80%, 85%, 90%, 91%, 92%, 93%, 94%, 95%, or more identical to the recited polypeptide.

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, or glycosylation. Such linkage can be covalent or non-covalent as is understood by those of skill in the art.

In various embodiments, the recited polypeptides may be present in 1, 2, 3, 4, 5, 6, 7, 8, 9, or 10 copies, preferably in one copy. When present in multiple copies, the copies are contiguous to each other. For example, 2 copies of ADP5 would be: PGYIN(L/F)SYE(K/N)SHSQAIN(T/V)DRTAP-GYIN(L/F)SYE(K/N)SHSQAIN(T/V)DRTA (SEQ ID NO: 5). Further examples will be readily apparent to those of skill in the art based on the teachings herein.

In one embodiment, the isolated ADPs comprise or consist of the amino acid sequence (PGYIN(L/F)SY(E/A)(K/N/A)SHSQAIN(T/V)(D/A)(R/A)TA)$_{1-10}$ (SEQ ID NO: 2) (ADP5), or a functional equivalent thereof. In a further embodiment, the ADP comprises or consists of (PGYIN(L/F)SYE(K/N)SHSQAIN(T/V)DRTA)$_{1-10}$ (SEQ ID NO: 24) (ADP5), or a functional equivalent thereof. In preferred embodiments, ADP5 comprises or consists of (PGYINFSYENSHSQAINVDRTA)$_{1-10}$ (SEQ ID NO: 6) (ADP5H), (PGYINLSYEKSHSQAINTDRTA)$_{1-10}$ (SEQ ID NO: 7)(ADP5M), or a functional equivalent thereof, wherein "ADP5H" refers to ADP5 derived from human amelogenin and "ADP5M" refers to ADP5 derived from mouse amelogenin. In further embodiments, the polypeptide comprises or consists of an ADP5 mutant, selected from the group consisting of ADP5(V1):(PGYIN(L/F)SYA(K/N)SHSQAIN(T/V)ARTA)$_{1-10}$ (SEQ ID NO: 25);
ADP5(V2):(PGYIN(L/F)SYE(A/N)SHSQAIN(T/V)DATA)$_{1-10}$ (SEQ ID NO: 26);
ADP5(V3):(PGYIN(L/F)SYA(A/N)SHSQAIN(T/V)AATA)$_{1-10}$ (SEQ ID NO: 27);

or functional equivalents thereof, where "V" represents "variant." In further embodiments, the polypeptide comprises or consists of:

(PGYINLSYA(K/N)SHSQAINTARTA)$_{1-10}$; (SEQ ID NO: 32)

(PGYINLSYE(A/N)SHSQAINTDATA)$_{1-10}$; (SEQ ID NO: 33)

(PGYINLSYA(A/N)SHSQAINTAATA)$_{1-10}$; (SEQ ID NO: 34)

(PGYINFSYA(K/N)SHSQAINVARTA)$_{1-10}$; (SEQ ID NO: 35)

(PGYINFSYE(A/N)SHSQAINVDATA)$_{1-10}$; (SEQ ID NO: 36)

(PGYINFSYA(A/N)SHSQAINVAATA)$_{1-10}$; (SEQ ID NO: 37)

(PGYINLSYAKSHSQAINTARTA)$_{1-10}$; (SEQ ID NO: 38)

(PGYINLSYEASHSQAINTDATA)$_{1-10}$; (SEQ ID NO: 39)

(PGYINLSYAASHSQAINTAATA)$_{1-10}$; (SEQ ID NO: 40)

(PGYINFSYANSHSQAINVARTA)$_{1-10}$; (SEQ ID NO: 41)

(PGYINFSYEASHSQAINVDATA)$_{1-10}$; and (SEQ ID NO: 42)

(PGYINFSYAASHSQAINVAATA)$_{1-10}$. (SEQ ID NO: 43)

In various embodiments, ADP5, ADP5M, ADP5H, or any of the variations thereof is present in 1, 2, 3, 4, 5, 6, 7, 8, 9, or 10 copies. In a preferred embodiment, ADP5, ADP5M, ADP5H, or any of the variations there is present in 1 copy. ADP5 is shown in the examples that follow to mimic the mineralization promotion effect of the wild type amelogenin protein on a given solid surface, including dentin on human tooth, rapidly, and thus can be used in any of the methods disclosed herein. In a most preferred embodiment, the ADP5 comprises or consists of ADP5H, or any of the variations thereof, preferably in one copy.

In another embodiment, the isolated ADPs comprise or consist of the amino acid sequence (HPP(S/T)HTLQPHHH(L/I)PVVPAQQPV(A/I)PQ QPMMPVPG(H/Q)HSMTP(T/I)QH)$_{1-10}$ (SEQ ID NO: 4)(ADP7), or a functional equivalent thereof. In a preferred embodiment, ADP7 comprises or consists of
(HPPSHTLQPHHHLPV-VPAQQPVAPQQPMMPVPGHHSMTPTQH)$_{1-10}$ (SEQ ID NO: 8)(ADP7M);
(HPPTHTLQPHHHIPV-VPAQQPVIPQQPMMPVPGQHSMTPIQH)$_{1-10}$ (SEQ ID NO: 9)(ADP7H), or a functional equivalent thereof, wherein "ADP7H" refers to ADP7 derived from human amelogenin and "ADP7M" refers to ADP7 derived from mouse amelogenin. In various embodiments, ADP 7, ADP7M, or ADP7H is present in 1, 2, 3, 4, 5, 6, 7, 8, 9, or 10 copies. In a preferred embodiment, ADP7, ADP7M, or ADPH7 is present in 1 copy. ADP7 is shown in the examples that follow to control hydroxyapatite (HA) crystallography, and morphology, in a solution phase, and thus can be used in any of the methods disclosed herein. ADP7 can also be used, for example, to target and immobilize bioactive molecules of interest (therapeutics, labeling molecules, other polypeptides of interest, etc.) to HA surfaces on the tooth. In a most preferred embodiment, the ADP7 comprises or consists of ADP7H, preferably in one copy.

In one embodiment, the isolated ADPs comprise or consist of the amino acid sequence WP(A/S)TDKTKREEVD)$_{1-10}$ (SEQ ID NO: 1)(ADP3), or a functional equivalent thereof. In a preferred embodiment, ADP5 comprises or consists of ((WPATDKTKREEVD)$_{1-10}$ (SEQ ID NO: 10) (ADP3M) or (WPSTDKTKREEVD)$_{1-10}$ (SEQ ID NO: 11) (ADP3H), or a functional equivalent thereof, wherein "ADP3H" refers to ADP3 derived from human amelogenin and "ADP3M" refers to ADP3 derived from mouse amelogenin. In various embodiments, ADP3, ADP3M, or ADP3H is present in 1, 2, 3, 4, 5, 6, 7, 8, 9, or 10 copies. In a preferred embodiment, ADP3, ADP3M, or ADP3H is present in 1 copy. ADP3 is a low similarity HA binder, and thus may be used in any of the methods of the invention. ADP3 can also be used, for example, to target and immobilize bioactive molecules of interest (therapeutics, labeling molecules, other polypeptides of interest, etc.) to HA surfaces on the tooth. In a most preferred embodiment, the ADP3 comprises or consists of ADP3H, preferably in one copy.

In various other preferred embodiments, the isolated polypeptide comprises or consists of a polypeptide selected from the group consisting of:

(i) (HTLQPHHH(L/I)PVV)$_{1-10}$ (SEQ ID NO: 12) (ADP1);
(ii) (VPG(H/Q)HSMTP(T/I)QH)$_{1-10}$ (SEQ ID NO: 13) (ADP2)
(iii) (HPP(S/T)HTLQPHHH(L/I)PVV)$_{1-10}$ (SEQ ID NO: 14) (ADP4);
(iv) (PAQQPV(A-I)PQQPMMP)$_{1-10}$ (SEQ ID NO: 15) (ADP8);
(v) (HTLQPHHHLPVV)$_{1-10}$ (SEQ ID NO: 16) (ADP1M);
(vi) (HTLQPHHHIPVV)$_{1-10}$ (SEQ ID NO: 17) (ADP1H);
(vii) (VPGHHSMTPTQH)$_{1-10}$ (SEQ ID NO: 18) (ADP2M)
(vii) (VPGQHSMTPIQH)$_{1-10}$ (SEQ ID NO: 19) (ADP2H)
(ix) (HPPSHTLQPHHHLPVV)$_{1-10}$ (SEQ ID NO: 20) (ADP4M);
(x) (HPPTHTLQPHHHIPVV)$_{1-10}$ (SEQ ID NO: 21) (ADP4H);
(xi) (PAQQPVAPQQPMMP)$_{1-10}$ (SEQ ID NO: 22) (ADP8M); and
(xii) (PAQQPVIPQQPMMP)$_{1-10}$ (SEQ ID NO: 23) (ADP8H);
or functional equivalents thereof.

In various embodiments, the recited polypeptides may be present in 1, 2, 3, 4, 5, 6, 7, 8, 9, or 10 copies, preferably in one copy. Each of these polypeptides bind to HA, and thus, even apart from their mineralization effects, they can be used to target and immobilize bioactive molecules of interest (therapeutics, labeling molecules, other polypeptides of interest, etc.) to HA surfaces on the tooth. Furthermore, ADP7 is a combination of ADP4+ADP8+ADP2, while ADP1 is completely contained within ADP4. Thus, each of these polypeptides can also be used, for example, in synthetically preparing ADP7.

All of these embodiments can be combined with any other embodiment, unless the context clearly dictates otherwise.

In a second aspect, the present invention provides recombinant fusion polypeptide, comprising (a) the ADP of any embodiment or combination of embodiments of the first aspect of the invention; and (b) a heterologous polypeptide.

As used herein, a "heterologous polypeptide" is any polypeptide that either (a) is not derived from amelogenin; or (b) is a different ADP than the ADP recited in component (a) of the recombinant fusion polypeptide. The recombinant fusion polypeptide does not include wild type amelogenin. Thus, for example, the recombinant fusion polypeptide may comprise or consist of a fusion of ADP5 and ADP7, so long as the fusion polypeptide is not amelogenin.

The recombinant fusion polypeptides of the invention can be used, for example, to treat dental disease. Thus, providing the ADPs as fusion polypeptides is a useful strategy for providing increased functionality when carrying out such treatments, or for any other suitable use.

In one embodiment, the heterologous polypeptide is a detectable polypeptide, to allow for detection of the recombinant fusion, for example, during administration to treat dental disease. In another embodiment, the heterologous polypeptide is an affinity tag of any type (including but not limited to FLAG tags, hexa-histidine tags, and myc tags) that, for example, can be used to assist in isolation of the polypeptide.

In various other embodiments, the heterologous polypeptide provides added functionality, for example, when the fusion polypeptides are used to treat dental disease. Exemplary such heterologous polypeptide include, but are not limited to anti-microbial polypeptides (inhibiting bacterial infection), biomineralization-promoting polypeptides (i.e.: any polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides. As will be understood by those of skill in the art, the recited heterologous polypeptide may comprise or consist of the full length protein, or functional polypeptides derived therefrom. Such heterologous polypeptides are known to those of skill in the art. In various non-limiting embodiments, such heterologous polypeptides include, but are not limited to dentin or polypeptides derived therefrom; cementum, or polypeptides derived therefrom; or other amelogenin-derived peptides including but not limited to:

```
                                          (SEQ ID NO: 28)
MPLPPHPGSPGYINLSYEVLTPLKWYQSMIRQPPLSPILPELPLEA
WPATDKTKREEVD
```

```
                                          (SEQ ID NO: 29)
MPLPPHPGSPGYINLSYEVLTPLKWYQSMIRQPYPSYGYEPMGGW;

(SEQ ID NO: 30)
LPPHPGSPGYINLSYEVLTPLKWYQSMIRQPYPSYGYE; and (SEQ ID NO: 31)
SPILPELPLEAWPATDK.
```

In a third aspect, the present invention provides compositions, comprising (a) the ADP of any embodiment or combination of embodiments of the first aspect of the invention; and (b) a non-peptide moiety linked to the amelogenin-derived polypeptide.

As used herein, a "non-peptide moiety" is any non-peptide moiety, whether naturally occurring or synthetic, that provides added functionality to the ADPs of the invention. For example, the non-peptide moiety may be any organic or inorganic nanostructure, or hybrids thereof. The compositions can be used, for example, to treat dental disease. Thus, providing the ADPs as the recited compositions is a useful strategy for providing increased functionality when carrying out such treatments, or for any other suitable use.

In one embodiment, the non-peptide moiety may be a non-peptide detectable moiety, including but not limited to radioactive isotopes, non-peptide affinity tags, isotope-coded affinity tags, and fluorophores, to allow for detection of the composition, for example, during administration to treat dental disease.

In other embodiments, the non-peptide moiety may comprise organic nanostructures (ex: micelles, liposomes, and dendrimers) or inorganic nanostructures (ex: metallic, semi-conducting and dielectric), including but not limited to nanotubes, nanowires, nanoparticles, atomic clusters, quantum dots, single layer or multilayer atomic materials, inorganic ions or ion clusters, and organic-inorganic hybrid nanostructures, and non-peptide polymers. These embodiments can be used, for example, to provide structural features of interest for a given application of the compositions.

In other embodiments, the non-peptide moiety may comprise non-peptide entities that provide for additional therapeutic benefit to a subject being treated, including but not limited to fish flour, amino acids (including but not limited to glycine), and non-peptide polymers.

In each of the second and third embodiments, the heterologous polypeptide or non-peptide moiety can be linked to the ADP through covalent bonding, including, but not limited to, disulfide bonding, hydrogen bonding, electrostatic bonding, recombinant fusion and conformational bonding. Alternatively, the heterologous polypeptide or non-peptide moiety can be linked to the ADP by means of one or more linking compounds. Techniques for conjugating moieties to polypeptides are well known to the skilled artisan.

Any suitable detectable polypeptide or detectable non-peptide moiety can be linked to the ADP in the second and third aspects of the invention, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection techniques and/or methods used. Enzymes typically conjugated to polypeptides to permit their visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The ADPs can be labeled using colloidal gold or they can be labeled with radioisotopes, such as $^{33}$P, $^{32}$P, $^{35}$S, $^{3}$H, and $^{125}$I. ADPs of the invention can be attached to radionuclides directly or indirectly via a chelating agent by methods well known in the art.

In a fourth aspect, the present invention provides pharmaceutical compositions, comprising one or more polypeptides, recombinant fusion proteins, or compositions of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a iris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid; and various mixtures thereof. In other embodiments, the pharmaceutical composition includes a bulking agent, like, glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides of the invention may be the sole active agent in the pharmaceutical composition, or the composition may further comprise one or more other active agents suitable for an intended use, including but not limited to anti-microbial polypeptides (inhibiting bacterial infection), biomineralization-promoting polypeptides (i.e.: any polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by any suitable route. In a preferred embodiment, the pharmaceutical compositions and formulations are designed for topical administration, and may include ointments, lotions, creams, pastes, gels, drops, sprays, liquids and powders. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

In a preferred embodiment the pharmaceutical compositions are in the form of a dental care product, including but not limited to toothpaste, toothpowders, mouthwash, dental floss, liquid dentifrices, dental tablets, topical gels, troches, chewing gums, dental pastes, gingival massage creams, gargle tablets, lozenges, and food products. Thus, in a fifth aspect, the present invention provides oral care products, comprising any embodiment or combination of embodiments of the polypeptides, recombinant fusion proteins, and/or compositions of the invention. Such oral care products can be used, for example, in treating dental disease.

In a sixth aspect, the present invention provides isolated nucleic acids encoding an ADP or fusion polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a seventh aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In an eighth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a ninth aspect, the present invention provides methods for treating dental disease, comprising administering to a subject in need thereof an amount effective to treat the dental disease of the polypeptide, recombinant fusion protein, composition, pharmaceutical composition or oral care product of any embodiment or combination of embodiments of the invention.

As shown herein, the inventors have discovered that the polypeptides of the invention can be used to treat a variety of dental diseases. While not being bound by a specific mechanism of action, the inventors believe that the polypeptides of the invention direct mineralization of dental lesions to form a "dento-mimetic" mineral layer, which also serves to reduce dental hypersensitivity and bacterial infiltration. It is further believed that some of the polypeptides exert their activity via binding to hydroxyapatite (HA) surfaces on the tooth to kinetically promote remineralization, occluding of dentin tubules to prevent/limit stimulants from reaching the tubules, and/or rebuilding lost mineral to create a physical barrier against bacteria. Thus, the methods of the invention provide a great improvement over prior art methods for treating dental disease.

The subject may be any subject that can contract dental disease, including but not limited to mammals. In various embodiments, the mammal is a human, dog, cat, horse, cow, sheep, goat, pig, or other pet or food/dairy animal. In a preferred embodiment, the subject is a human.

As used herein, dental disease is any disease or condition affecting the teeth, gums, or other tissues of the mouth that involves (directly or indirectly) demineralization (i.e.: loss of mineral content on the surface of the tooth. In a healthy person, tooth is in a cycle of demineralization and remineralization through the exchange of ions between the surface of the tooth and the surrounding saliva. When the rate of demineralization exceeds the rate of remineralization, it leads to dental disease. Demineralization is a major cause of most dental diseases. Loss of mineral can be caused by any means, including but not limited to acidic diet, dry mouth, tooth whitening, abrasion and bacterial plaque formation.

Such dental diseases may include, but are not limited to, periodontitis, tooth erosion, hypersensitivity, dental caries (also known as tooth decay/cavities), dental fluorosis, tooth resorption, craniomaxillofacial bone disease, and gingival recession.

As used herein, "periodontitis" is a set of inflammatory diseases affecting the periodontium, i.e., the tissues that surround and support the teeth. Periodontitis involves progressive loss of the alveolar bone around the teeth, and if left untreated, can lead to the loosening and subsequent loss of teeth. Periodontitis is caused by microorganisms that adhere to and grow on the tooth's surfaces, along with an overly aggressive immune response against these microorganisms.

As used herein, "tooth demineralization" or "tooth erosion" is erosion of tooth enamel. This erosion may be caused by any number of factors, including bacterial infection, teeth grinding, abrasion, erosion, and abfraction As used herein, "hypersensitivity" is an increased exposure to the environment of nerves inside the dentin of teeth, causing an increased nerve response, which can be mild to severe. The sensitivity may be caused by any factor, including but not limited to wear, tooth decay or exposed tooth roots.

As used herein, "dental caries" is an infectious disease usually bacterial in origin that causes demineralization of the hard tissues (enamel, dentin and cementum) and destruction of the organic matter of the tooth. The bacteria most commonly responsible for dental cavities are *Streptococcus mutans* and *Lactobacillus*. If left untreated, dental caries can lead to pain, tooth loss and systemic infection.

As used herein, "dental fluorosis" is a developmental disturbance of dental enamel caused by excessive exposure to high concentrations of fluoride during tooth development. The risk of fluoride overexposure is greatest between the ages of 3 months and 8 years. In its mild forms, fluorosis often appears as unnoticeable, tiny white streaks or specks in the enamel of the tooth. In its most severe form, tooth appearance is marred by discoloration or brown markings.

The enamel may be pitted, rough and hard to clean. The spots and stains left by fluorosis are permanent and may darken over time.

As used herein, "tooth resorption" is a process by which all or part of a tooth structure is lost. In "external resorption" the root surface is lost; this can be caused, for example, by chronic inflammation, cysts, tumors, trauma, reimplantation of a tooth, or by unknown causes. "Internal resorption" involved resorption of dentin and pulpal walls centrally within the root canal; the cause can sometimes be attributed to tooth trauma, but often there is no known cause.

As used herein, "gingival recession" is root (cementum) that is exposed to the environment as a result of retraction of the gumline from the crown of the teeth. Cementum is a calcified tissue that supports attachment of the tooth to mandibular or maxillar bone through periodontal ligaments. Exposed cementum can result in resorption of cementum and exposure of the underlying dentin, therefore, hypersensitivity and pain.

In one embodiment, "craniomaxillofacial bone disease" refers to disease of dental bone structures.

As used herein, "treating dental disease" means accomplishing one or more of the following: (a) reducing the severity of the dental disease; (b) limiting or preventing development of symptoms characteristic of the dental disease(s) being treated; (c) inhibiting worsening of symptoms characteristic of the dental disease(s) being treated; (d) limiting or preventing recurrence of the dental disease(s) in patients that have previously had the disorder(s); (e) limiting or preventing recurrence of symptoms in patients that were previously symptomatic for the dental disease(s); and (f) limiting development of the dental disease in a subject at risk of developing the dental disease, or not yet showing the clinical effects of the dental disease.

As used herein, an "amount effective" refers to an amount of the polypeptide that is effective for treating and/or limiting dental disease. The polypeptides are typically formulated as a pharmaceutical composition, such as those disclosed above, and can be administered via any suitable route, including orally, parentally, by inhalation spray, or topically in dosage unit formulations containing conventional pharmaceutically acceptable carriers, adjuvants, and vehicles. In a preferred embodiment, the pharmaceutical compositions and formulations are topically administration, such as in the form of ointments, lotions, creams, pastes, gels, drops, sprays, liquids and powders. Conventional pharmaceutical carriers, aqueous, powder or oily bases, thickeners and the like may be necessary or desirable.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In each of these embodiments, or combinations of embodiments, the polypeptide may be any embodiment or combination of embodiments of the first, second, or third aspects of the invention. Thus, in one embodiment, ADPs comprise or consist of (a) (WP(A/S)TDKTKREEVD)$_{1-10}$ (SEQ ID NO: 1) (ADP3);

(b) (PGYIN(L/F)SY(E/A)(K/N/A)SHSQAIN(T/V)(D/A)(R/A)TA)$_{1-10}$ (SEQ ID NO: 2) (ADP5);

(c) (LPPLFSMPLSPILPELPLEAWPAT)$_{1-10}$ (SEQ ID NO: 3) (ADP6); and (d) 12-43 contiguous amino acids of (HPP(S/T)HTLQPHHH(L/I)PVVPAQ QPV(A/I)PQQPMMPVPG(H/Q)HSMTP(T/I)QH)$_{1-10}$ (SEQ ID NO: 4) (ADP7);

or functional equivalents thereof. In various embodiments, the recited polypeptides may be present in 1, 2, 3, 4, 5, 6, 7, 8, 9, or 10 copies, preferably in one copy.

In one preferred embodiment, the methods comprise administering a polypeptide comprising or consisting of the amino acid sequence (PGYIN(L/F)SY(E/A)(K/N/A)SHSQAIN(T/V)(D/A)(R/A)TA)$_{1-10}$ (SEQ ID NO: 2) (ADP5), or a functional equivalent thereof. In a further embodiment, the ADP administered comprises or consists of (PGYIN(L/F)SYE(K/N)SHSQAIN(T/V)DRTA)$_{1-10}$ (SEQ ID NO: 24) (ADP5), or a functional equivalent thereof. In preferred embodiments, the administered ADP5 comprises or consists of (PGYINFSYENSHSQAINVDRTA)$_{1-10}$ (SEQ ID NO: 6)(ADP5H), (PGYINLSYEKSHSQAINTDRTA)$_{1-10}$ (SEQ ID NO: 7) (ADP5M), or a functional equivalent thereof. In further embodiments, the polypeptide comprises or consists of an ADP5 mutant, selected from the group consisting of

ADP5(V1):(PGYIN(L/F)SYA(K/N)SHSQAIN(T/V)ARTA)$_{1-10}$ (SEQ ID NO: 25);

ADP5(V2):(PGYIN(L/F)SYE(A/N)SHSQAIN(T/V)DATA)$_{1-10}$ (SEQ ID NO: 26);

ADP5(V3):(PGYIN(L/F)SYA(A/N)SHSQAIN(T/V)AATA)$_{1-10}$ (SEQ ID NO: 27);

or functional equivalents thereof, where "V" represents "variant." In further embodiments, the polypeptide comprises or consists of (PGYINLSYA(K/N)SHSQAINTARTA)$_{1-10}$ (SEQ ID NO: 32);

(PGYINLSYE(A/N)SHSQAINTDATA)$_{1-10}$ (SEQ ID NO: 33);

(PGYINLSYA(A/N)SHSQAINTAATA)$_{1-10}$ (SEQ ID NO: 34);

(PGYINFSYA(K/N)SHSQAINVARTA)$_{1-10}$ (SEQ ID NO: 35);

(PGYINFSYE(A/N)SHSQAINVDATA)$_{1-10}$ (SEQ ID NO: 36);

(PGYINFSYA(A/N)SHSQAINVAATA)$_{1-10}$ (SEQ ID NO: 37);

(PGYINLSYAKSHSQAINTARTA)$_{1-10}$ (SEQ ID NO: 38);

(PGYINLSYEASHSQAINTDATA)$_{1-10}$ (SEQ ID NO: 39);

(PGYINLSYAASHSQAINTAATA)$_{1-10}$ (SEQ ID NO: 40);

(PGYINFSYANSHSQAINVARTA)$_{1-10}$ (SEQ ID NO: 41);

(PGYINFSYEASHSQAINVDATA)$_{1-10}$ (SEQ ID NO: 42); and (PGYINFSYAASHSQAINVAATA)$_{1-10}$ (SEQ ID NO: 43).

In various embodiments, ADP5, ADP5M, ADP5H, or any of the variations thereof is present in 1, 2, 3, 4, 5, 6, 7, 8, 9, or 10 copies. In a preferred embodiment, ADP5, ADP5M, ADP5H, or any of the variations there is present in 1 copy. ADP5 is shown in the examples that follow to mimic the mineralization promotion effect of the wild type amelogenin protein on a given solid surface, including dentin on human tooth, rapidly, and thus can be used in any of the methods disclosed herein. In a most preferred embodiment, the ADP5 comprises or consists of ADP5H, or any of the variations thereof, preferably in one copy.

In another preferred embodiment, the methods comprise administering a polypeptide comprising or consisting of the amino acid sequence (HPP(S/T)HTLQPHHH(L/I)PV-VPAQQPV(A/I)PQ QPMMPVPG(H/Q)HSMTP(T/I)QH)$_{1-10}$ (SEQ ID NO: 4) (ADP7), or a functional equivalent thereof. In a preferred embodiment, the ADP7 comprises or consists of
(HPPSHTLQPHHHLPV-VPAQQPVAPQQPMMPVPGHHSMTPTQH)$_{1-10}$ (SEQ ID NO: 8) (ADP7M);
(HPPTHTLQPHHHIPV-VPAQQPVIPQQPMMPVPGQHSMTPIQH)$_{1-10}$ (SEQ ID NO: 9) (ADP7H), or a functional equivalent thereof. In various embodiments, ADP 7, ADP7M, or ADP7H is present in 1, 2, 3, 4, 5, 6, 7, 8, 9, or 10 copies. In a preferred embodiment, ADP7, ADP7M, or ADPH7 is present in 1 copy. In a most preferred embodiment, the ADP7 comprises or consists of ADP7H, preferably in one copy.

In a further embodiment, the polypeptide for use in the methods comprises or consists of the amino acid sequence WP(A/S)TDKTKREEVD)$_{1-10}$ (SEQ ID NO: 1) (ADP3), or a functional equivalent thereof. In a preferred embodiment, ADP3 comprises or consists of ((WPATDKTKREEVD)$_{1-10}$ (SEQ ID NO: 10) (ADP3M) or (WPSTDKTKREEVD)$_{1-10}$ (SEQ ID NO: 11) (ADP3H), or a functional equivalent thereof. In various embodiments, ADP3, ADP3M, or ADP3H is present in 1, 2, 3, 4, 5, 6, 7, 8, 9, or 10 copies. In a preferred embodiment, ADP3, ADP3M, or ADP3H is present in 1 copy. In a most preferred embodiment, the ADP3 comprises or consists of ADP3H, preferably in one copy.

In various further embodiments, the polypeptide for use in the methods comprises or consists of a polypeptide selected from the group consisting of selected from the group consisting of
  (i) (HTLQPHHH(L/I)PVV)$_{1-10}$ (SEQ ID NO: 12) (ADP1);
  (ii) (VPG(H/Q)HSMTP(T/I)QH)$_{1-10}$ (SEQ ID NO: 13) (ADP2)
  (iii) (HPP(S/T)HTLQPHHH(L/I)PVV)$_{1-10}$ (SEQ ID NO: 14) (ADP4);
  (iv) (PAQQPV(A-I)PQQPMMP)$_{1-10}$ (SEQ ID NO: 15) (ADP8);
  (v) (HTLQPHHHLPVV)$_{1-10}$ (SEQ ID NO: 16) (ADP1M);
  (vi) (HTLQPHHHIPVV)$_{1-10}$ (SEQ ID NO: 17) (ADP1H);
  (vii) (VPGHHSMTPTQH)$_{1-10}$ (SEQ ID NO: 18) (ADP2M)
  (vii) (VPGQHSMTPIQH)$_{1-10}$ (SEQ ID NO: 19) (ADP2H)
  (ix) (HPPSHTLQPHHHLPVV)$_{1-10}$ (SEQ ID NO: 20) (ADP4M);
  (x) (HPPTHTLQPHHHIPVV)$_{1-10}$ (SEQ ID NO: 21) (ADP4H);
  (xi) (PAQQPVAPQQPMMP)$_{1-10}$ (SEQ ID NO: 22) (ADP8M); and
  (xii) (PAQQPVIPQQPMMP)$_{1-10}$ (SEQ ID NO: 23) (ADP8H);
or functional equivalents thereof.

In various embodiments, the recited polypeptides may be present in 1, 2, 3, 4, 5, 6, 7, 8, 9, or 10 copies, preferably 1 copy.

All of these aspects/embodiments disclosed herein can be combined with any other aspect/embodiment, unless the context clearly dictates otherwise.

EXAMPLE 1

Abstract

Cementum is the outer-, mineralized-tissue on the tooth root. It is part of the system of periodontal tissue that anchors the tooth to the bone. Periodontal disease results from the destructive behavior of the host elicited by an infectious biofilm adhering to the tooth root and left untreated, may lead to tooth loss. Tissue specific extracellular-matrix proteins for repairing damaged mineralized tissues of the teeth have been limited to date in therapeutic applications. Here, we describe a novel protocol for identifying peptide sequences from native proteins associated with controlling hydroxyapatite biomineralization. Using amelogenin as a case study and a bioinformatics scoring matrix, we identified similarity regions, for amelogenin with a set of hydroxyapatite-binding peptides, previously selected by phage display. Among these regions, referred to as amelogenin derived peptides, a 22-amino acids long peptide (ADP5) was shown to facilitate cell-free formation of a cementum-like hydroxyapatite mineral layer on demineralized human root dentin that, in turn, supported attachment of periodontal ligament cells in vitro. Our findings have several implications in peptide-assisted mineral formation that mimics biomineralization events. By further elaborating the mechanism for protein control over the biominerals formed in these systems we afford new insights into the evolution of protein-mineral interactions. By exploiting small peptide domains of native proteins, our understanding of structure-function relationships of biomineralizing proteins can be extended and these peptides can be utilized to engineer the mineral formation. Finally, the ADPs have clinical application to treat dental disease, such as through repair of diseased root surfaces caused by caries and periodontal disease, so as to promote the regeneration of periodontal tissues and thereby reduce the morbidity associated with tooth loss.

Introduction

The distinguishing characteristics of dental bioceramic hard tissues, e.g., enamel, cementum, and dentin, are achieved due to the amount of the hydroxyapatite (HAp) crystallites formed, their dimensional structural characteristics and their overall architecture. These characteristics originate from the tissue-specific extracellular matrix (ECM) proteins found within each tissue during its development (1-5) and which act as regulators of nucleation and growth of biological apatite (1, 2, 6). Periodontal disease is caused by the host's inflammatory reaction to the bacterial biofilms that adhere to the tooth surface (7) and results in periodontal tissue destruction. It is one of the most prevalent infections of mankind, and left unchecked, will result in the loss of the teeth and surrounding tissue, including bone (7, 8). The use of dental ECM proteins as therapeutic agents to repair damage caused by such diseases has been limited so far due to technical and financial limitations in the identification, extraction and purification of these proteins. We previously used the enamel protein, amelogenin, to identify similarity regions, i.e., similar amino acid sequences, with a set of HAp-binding peptides (HABP) that we previously experimentally selected (23). Amelogenin is expressed during tooth enamel formation and contributes to the hardest and most highly mineralized tissue in the human body by exerting control over the dimension and directionality of HAp crystals formed within the assembled protein matrix (17-19). Although certain regions of amelogenin amino acid sequence are proposed to interact with calcium phosphate minerals, an extensive mapping of putative crystal-interaction or mineral nucleation domains is still lacking (20, 21). Here, we show that functional peptides can be derived from amelogenin using phage display-selected peptides as a knowledge base and identifying next generations of peptides by bioinformatics. We then show that these peptides can function to direct the cell-free re-mineralization of the tooth root resulting in a cementomimetic (e.g., cementum-like) material and thus can contribute to cell-based regeneration of periodontal tissue.

Materials and Methods

Combinatorial Selection of Peptides

Selection of the peptides by phage display and the HAp binding and mineralization characterization were carried out as previously described (22) (see Supplemental Information).

Similarity Analysis

The amino acid sequences obtained from the combinatorially selected peptides have been used as the data source for our knowledge-based design. Using the methods previously described by Oren and colleagues (23), two scoring matrices, HAp12I and HApC7CI, were derived for the peptides selected from the 12- and c7c-phage libraries (New England BioLabs Inc., USA), respectively. The Point Accepted Mutation 250 (PAM 250) was chosen as the seed matrix to optimize the new matrices specific to the selected peptides. The PAM matrix gives substitution probabilities for sequences that experience a certain number of point mutations in every hundred amino acids. Therefore, PAM 250 reflects the probabilities for 250 point mutations for every 100 amino acids. PAM 250 was modified to compensate for the relative abundance of amino acids within the libraries used to select the HAp-binding peptides (HABP) and for the codon usage of the host organism (*E. coli* K12 ER2738) used to amplify the phages. To identify the sequence similarities between the selected peptides with the recombinant mouse 180 amino acid long amelogenin (rM180), we divided the rM180 amino acid sequence into segments with the same length as those from the phage libraries (i.e.; 7- or 12-amino acids). Each iteration generated a segment starting from the next amino acid, therefore, creating all possible 7 or 12 amino acid segment lengths for the whole M180 sequence. Then, each segment was compared with each HABP and was given a similarity score. Once every combination of the HABPs and amelogenin segments were compared, regions that demonstrated high similarity scores against both libraries were overlapped. These coinciding high similarity regions were picked as the putative strong binding regions (see Supporting Information). In the same way, coinciding low similarity regions were picked as the putative weak binding regions. These regions were then refined by protein structure prediction, $Ca^{+2}$ ion binding domain predictions and meta-functional signature analyses (see Supporting Information). A schematic description of the design process is shown in FIG. 1a.

Peptide Synthesis rM180 amelogenin was created as described previously by Moradian-Oldak and colleagues (24). The ADPs were synthesized by standard solid phase peptide synthesis technique on Wang resin using F-moc chemistry and HBTU activation. CSBio 336s (CSBio, USA) automated peptide synthesizer was used for the synthesis. The resulting resin-bound peptides were cleaved and side-chain-deprotected using Reagent K (trifluoroacetic acid /thioanisole/$H_2O$/phenol/ethanedithiol (87.5:5:5:2.5)) and, precipitated by cold ether. The crude peptides obtained were purified by reverse phase high performance liquid chromatography up to a >98% purity (Gemini 10µ C18 110A column). The masses of the purified peptides were checked by mass spectroscopy using a MALDI-TOF mass spectrometer (Bruker Daltonics, USA).

Binding Analysis via QCM

Calcium phosphate coated QCM electrodes were purchased commercially. (Q-Sense, Sweden) The diameter of the crystals and electrodes were 8.8 mm and 5.0 mm, respectively. The oscillation electronic circuit was a typical Collpits oscillator, which had a buffer amplifier. A 12 V DC current was applied to the oscillator circuit to drive the crystal, and the frequency was measured with a Hewlett-Packard 53131A frequency counter sampling at 225 Hz (Universal Counter, Agilent Technologies). After the crystal was mounted in the cell, they were cleaned and dried with high-purity nitrogen gas and used immediately. To establish a stable baseline, a sufficient amount of buffer solution was introduced into the cell before adding the peptide. The frequency change of the crystal in pure buffer solution was recorded for 30 to 60 minutes. After this, the desired amount of ADPs was introduced into the cell and the frequency change was recorded continuously.

In vitro Solution Biomineralization

An alkaline phosphatase (AP) based mineralization model was used as described before to investigate the mineralization behaviors of the peptides (22) (see Supporting Information for details).

Ex vivo Re-mineralization of Tooth Root

The cementum-root stock blocks were prepared from single rooted, extracted adult teeth collected at the University of Washington Dental School clinics. No individual identifiers were used and the use of such material complied with the Institutional Review Board guidelines. The teeth were kept in 70% ethanol solution at 4° C. until the specimens were prepared. Cylindrical blocks of 4 mm diameter were cut from the acellular cementum, close to the cementoenamel junction using a trephine bur. The teeth were kept immersed in 70% ethanol-phosphate buffered saline (PBS) during the cutting to prevent heat damage due to friction. The cut cylindrical blocks were cleaned of contaminating material using PBS and demineralized with 35% phosphoric acid gel for 10 seconds. The specimens were stored in 70% ethanol-PBS solution at 4° C. until used. Prior to coating the specimens with the peptide, the previously cut cylindrical blocks were rehydrated and equilibrated for 2 hours in 24 mM Tris-HCl buffer, pH 7.4. The lyophilized ADP was dissolved in 24 mM Tris-HCl buffer, pH 7.4 to a final concentration of 0.4 mM. A 50 µl drop of the ADP solution was dropped on top of the specimens and left on the specimen for 10 minutes at room temperature in a water saturated chamber to prevent evaporation. Control specimens were identically prepared only by dropping 50 µl of buffer alone. At the end of 10 minutes, the samples were rinsed twice with deionized water. Fluorescent microscopy analysis was performed with fluorescein isothiocyanate-labeled ADP (fADP).

Figure 3:
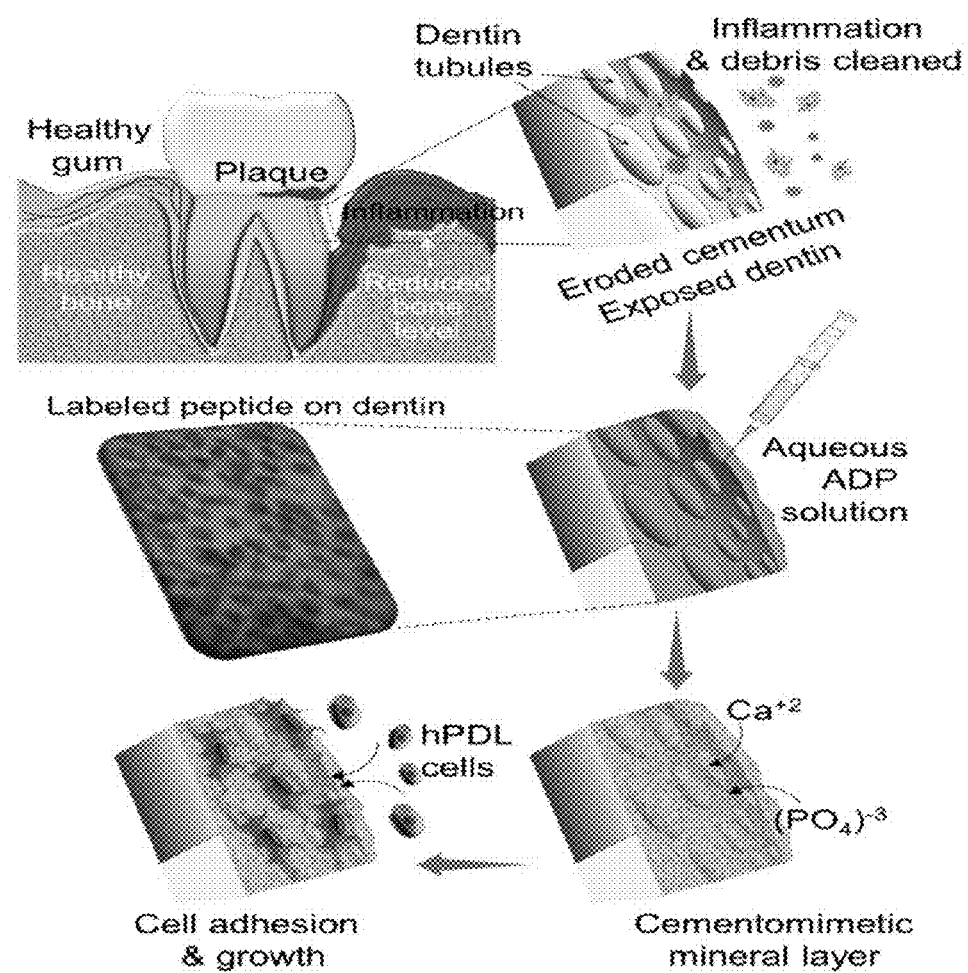
FIG. 3. Procedure for in vitro-, cell-free synthesis of cementomimetic layer by ADP5 on human root surfaces. Extracted human teeth are cleaned of any contaminating material and cylindrical pieces are cut right below the cementoenamel junction. An aqueous solution of ADP5, the mineralization directing peptide, is applied on the demineralized root surface. The specimen is immersed into a mineralization solution containing calcium and phosphate. Cell adhesion and proliferation is investigated on the re-mineralized root surfaces.

Solutions of 9.6 mM $CaCl_2$ and 5.6 mM $(PO_4)^{-3}$, a mixture of $NaH_2PO_4$—$H_2O$ and $Na_2HPO_4$-$7H_2O$, were prepared in 24 mM Tris-HCl buffer, pH 7.4. The peptide coated and non-coated control specimens were placed in 300 µl of $Ca^{+2}$ solution and an equal volume of $(PO_4)^{-3}$ solution was added to achieve a final concentration of 4.8 mM of $Ca^{+2}$ and 2.8 mM of $(PO_4)^{-3}$. The specimens were incubated in the mineralization solution for 2 hours at 37° C. in a water saturated atmosphere, removed from the mineralization solution and rinsed with 24 mM Tris-HCl buffer, pH 7.4. The specimens were kept in 70% ethanol solution at 4° C. until the time of characterization. A schematic explanation of the ex vivo re-mineralization is shown in FIG. 3.

Mechanical Properties of the Cementomimetic Layer

Figure 8:
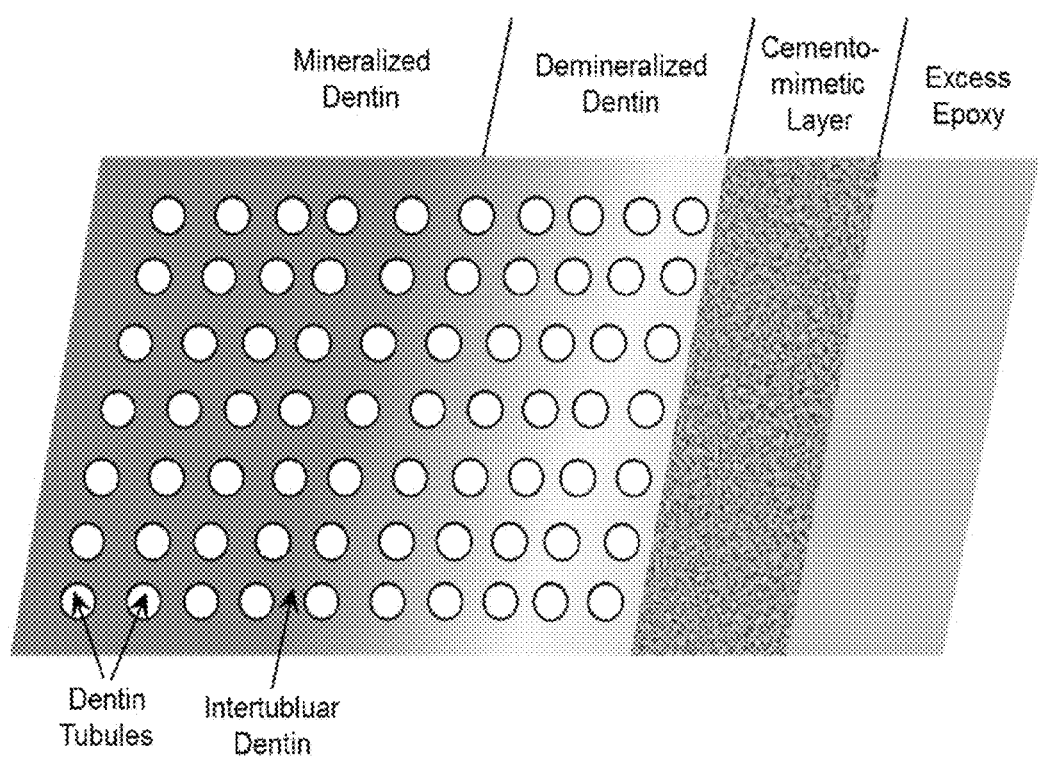
FIG. 8. Schematic of the sample which nanoindentation characterization was performed. 20 indentations were made on each region: mineralized dentin, demineralized dentin (~20 um), and cementomimetic layer (~10 um). Indentations in dentin were made strictly on intertubular dentin.

Mechanical properties of the cementomimetic layer were assessed by nanoindentation and qualitative mechanical abrasion tests. The samples were prepared by first infiltrating from the top of the cementomimetic layer with room-temperature-cure epoxy (Allied High Tech, Inc., U.S.A.) to provide a continuous volume for indentation characterization. After the epoxy was cured, the sample was ground to expose the interior in the cross-section of the specimen, then ultra-microtomed to achieve a smooth surface for nanoindentation. Twenty indentations each were taken on mineralized dentin region (indentations were made on intertubular dentin), demineralized dentin regions (adjacent to the cementomimetic layer) and the cementomimetic layer (see Supporting Information, FIG. 8).

Qualitative mechanical analysis was done by ultrasonication and mechanical abrasion. For ultrasonication, specimens were mounted on scanning electron microscopy (SEM) sample mounts and placed in 70% ethanol in a glass vial. The probe was set to 3 cm above the specimens and ultrasound energy was applied for 15 seconds yielding a total of 10 J. Mechanical abrasion was applied to the same specimens using an electric toothbrush intended for home use (Oral B, series 4000). The specimens and the toothbrush were fixed in position allowing the bristles to be brought into contact with the specimens for 1 minute, after which the samples were rinsed with 70% ethanol and analyzed with SEM.

Cell Adhesion and Growth Assays

Cell adhesion experiments were done using cultured human periodontal ligament (hPDL) fibroblasts. The cells were maintained in Dulbecco's Modified Eagle Medium (DMEM) (Gibco, USA) containing 10% fetal bovine serum (FBS) supplemented with 100 units/ml penicillin, 100 μm/ml streptomycin and 2 mM glutamine (PSG). The cells were used between the seventh and ninth passage. Before starting the cell adhesion assays, the mineralized specimens were taken out of the 70% ethanol solution and equilibrated in serum-free DMEM for 2 hours. The confluent hPDL cells were suspended with 0.05% Trypsin-EDTA and counted using a hemocytometer. The equilibrated tooth specimens were placed in 24-well plates, with 4 specimens per well performed in triplicates. The suspended hPDL cells were prepared in serum-free DMEM and $3\times10^4$ cells per well were seeded on top of the specimens. The specimens were incubated with the cells for 2 hours at 37° C. and 5% $CO_2$ atmosphere. After two hours the specimens were rinsed with the media and cells remaining on the surface were recovered from the surface of the specimen with 0.05% trypsin-EDTA. The cells so obtained were counted using CyQUANT cell proliferation assay kit (Invitrogen, USA).

After fixing with 2% glutaraldehyde in PBS for 10 minutes the cells were permeabilized with 0.1% Triton X in PBS for 2 minutes and blocked with 1% bovine serum albumin (BSA) for 30 minutes and stained with Phalloidin-Alexa fluor 488 (Invitrogen, USA) for fluorescence microscopy observations. The cells were observed and recorded using a TE 300 L microscope at an appropriate wavelength and gated filters (Nikon, Japan).

For proliferation assays, hPDL cells were prepared the same way as described above for the cell adhesion assays. The specimens were equilibrated in media and placed in 24 well plates, 4 specimens per well and performed in triplicate wells. The suspended hPDL cells were prepared in serum-free DMEM and $3\times10^4$ cells per well were seeded on top of the specimens. After 24 hours, the specimens were rinsed and transferred into new plates to prevent possible contamination of the cells that grow on the bottom of the plate. The cells were maintained in a water-jacketed incubator at 37° C. in 5% CO2 saturated to $H_2O$ and the media was exchanged every 48 hrs 2 with DMEM supplemented with 2% FBS. Triplicate samples were terminated after 2-, 6-, 10- and 15-days duration. At the end of each time point, the specimens were taken out of the wells, rinsed with serum-free DMEM, then with PBS. The cells were recovered from the specimen surface with 0.05% trypsin-EDTA and counted using CyQUANT cell proliferation assay kit (Invitrogen, U.S.A.).

Results

One component in the newly developed cementomimetic mineral construction is HAp-forming peptides that operate as mineral synthesizers and control deposition of a confluent nanostructured HAp layer. The procedure for designing these peptides is schematically described in FIG. 1. Using a phage display approach, we combinatorially selected more than 100 HABP from a 7-amino acid and a 12-amino acid phage peptide library and characterized their binding affinity to the HAp mineral under near-physiological conditions (22). Since not all of the peptides selected have the same affinity to HAp, we next categorized them into three classes as strong-, moderate-, and weak-binding peptides. Using bioinformatics classification protocols (23), we derived similarity-scoring matrices for both sets of selected septa- and dodeca-peptides. These matrices were used to systematically compare and identify similarity regions, i.e., domains of similar amino acid sequences between the experimentally selected HABPs and rM180. The comparisons yielded high and low similarity regions along the amelogenin (FIG. 1b). By overlapping the high similarity regions from both libraries, putative crystal binding sequences were identified, referred to as amelogenin-derived peptides, ADPs (FIG. 1b,e). The similarity analysis were refined and supported by other computational tools, i.e.; structure prediction, meta-functional signature and ion binding domains analyses (FIG. 1c,d) (see Supplemental Information). Many short amino acid sequences can be generated by this procedure and each has the potential to be used for specific applications requiring control over HAp formation and growth. The putative HAp interacting regions of amelogenin having the highest similarity, i.e., ADP1, ADP2, and ADP4, were synthesized chemically (see Supplemental Information). For comparison, we also synthesized amelogenin-derived peptides (ADP3, ADP6) corresponding to the previously proposed putative mineral-binding regions near the C-terminus (25-28), non-mineral interactive (e.g., low similarity score) regions (ADP5, ADP8) and finally ADP7, a peptide that included ADP1, ADP2 and ADP8 (FIG. 1e and Table 1). The HAp-binding affinities of these peptides were examined via quartz crystal microbalance (QCM) and their propensity to control formation of calcium phosphates was carried out via in vitro solution mineralization assays and ex vivo tooth remineralization experiments.

TABLE 1

Amino acid sequences, physico-chemical properties and the dissociation constant ($K_d$) of the ADPs used in this study.

| | M.W. | pI | Charge | G.R.A.V.Y. | $K_D$ (μM) |
|---|---|---|---|---|---|
| ADP1 | 1414.60 | 7.10 | 0 | −0.350 | 1.395 |
| ADP2 | 1328.40 | 7.00 | 0 | −1.067 | 1.611 |
| ADP3 | 1574.70 | 4.94 | (−4, +3) −1 | −1.862 | 6.397 |
| ADP4 | 1833.00 | 7.16 | 0 | −0.713 | 1.431 |
| ADP5 | 2465.60 | 7.16 | (−2, +2) 0 | −0.959 | 50 |
| ADP6 | 2630.10 | 3.79 | +2 | 0.592 | 6.247 |

TABLE 1-continued

Amino acid sequences, physico-chemical properties and the dissociation constant ($K_d$) of the ADPs used in this study.

|  | M.W. | pI | Charge | G.R.A.V.Y. | $K_D$ (µM) |
|---|---|---|---|---|---|
| ADP7 | 4645.30 | 7.28 | 0 | −0.824 | 1.148 |
| ADP8 | 1519.80 | 5.96 | 0 | −0.743 | 3.14 |

Binding Analysis via QCM

The dissociation constants ($K_D$) of the peptides were determined. The $K_D$ is an equilibrium constant that represents the concentration necessary to achieve 50% surface coverage. Experimental binding assays demonstrated that ADP1, ADP2, ADP4 and ADP7 exhibit strong affinity to HAp with $K_D$ values on the order of 1 µM, as was predicted by the similarity analysis (FIG. 2a, Table 1). Likewise, the binding affinities of the ADP3, ADP6, ADP5 and ADP8 were lower as predicted, with ADP5 having a significantly lower $K_D$ (50 mM). (FIG. 2a, Table 1)

In vitro Solution Biomineralization

We noted that there were three distinct trends of mineralization among the tested ADPs. The majority of the peptides (ADP1, ADP2, ADP3, ADP4, ADP6 and ADP8) exhibited similar kinetics to the negative control, where no peptide was present. The phage display selected HABP1 and the ADP7 identified in this study exhibited a slow mineralization trend (FIG. 2b). Interestingly, full-length rM180 and the ADP5 exhibited a fast mineralization trend, where more than half of the available free $Ca^{2+}$ was consumed at the end of the 90 minutes (FIG. 2b) (See Supplementary Information FIG. 6 for the mineralization trends of all ADPs). The microstructural and crystallographic analysis of the synthesized minerals via SEM, transmission electron microscopy (TEM) and x-ray diffraction (XRD) revealed another interesting consequence regarding the relationship between the mineral binding and mineralization activity. Similar to the mineralization kinetics, three distinct trends of mineral morphologies were observed. The majority of the peptides (ADP1, ADP2, ADP3, ADP4, ADP6, ADP8 and HABP1) produced spherulitic particles consistent with the formation of spherical amorphous calcium phosphate (ACP) and transformation into crystalline phases (29-31). The amount of radiating crystalline blade-like particles emanating from the spherulites was slightly higher for ADP1, ADP2, ADP4 and HABP1 (strong binders) compared to ADP3, ADP6, ADP8 (weak binders) and to the no peptide control, an order indicating that the amorphous to crystalline transformation rates were slightly different (FIG. 2c). In the case of rM180 and ADP7, however, a completely different morphology was observed. Needle like nano-crystals were organized into bundle-like assemblies were observed for rM180 and ADP7 (FIG. 2d). The bundle-like assemblies appeared to be better organized in the case of rM180, which is consistent with the self-assembly properties of amelogenin and the in vitro mineralization behavior of recombinant amelogenin (24, 32-34).

The particles formed in the presence of ADP5 were much smaller spherulites with a less electron-dense core and smaller radiating crystals. (FIG. 2c) The smaller particles sizes in the presence of ADP5 may be due to its nucleation dominate regime, as suggested from the data describing the mineralization kinetics.

The crystallographic analysis via XRD spectroscopy also confirmed that the observed morphological differences were due to different crystal structures. In all cases except rM180 and ADP7, the minerals yielded a broad peak around 2θ 25-30° indicating a poorly crystalline phase (FIG. 2e). In the presence of rM180 and ADP7, however, the XRD patterns consisted of numerous sharp peaks indicative of crystalline HAp. The major peaks were observed at 2θ=31.8° (d=2.81 Å) and 32.1° (d=2.78 Å) corresponding to (211) and (300) planes of HAp, respectively.

Ex vivo Remineralization of the Tooth Roots

Figure 7:
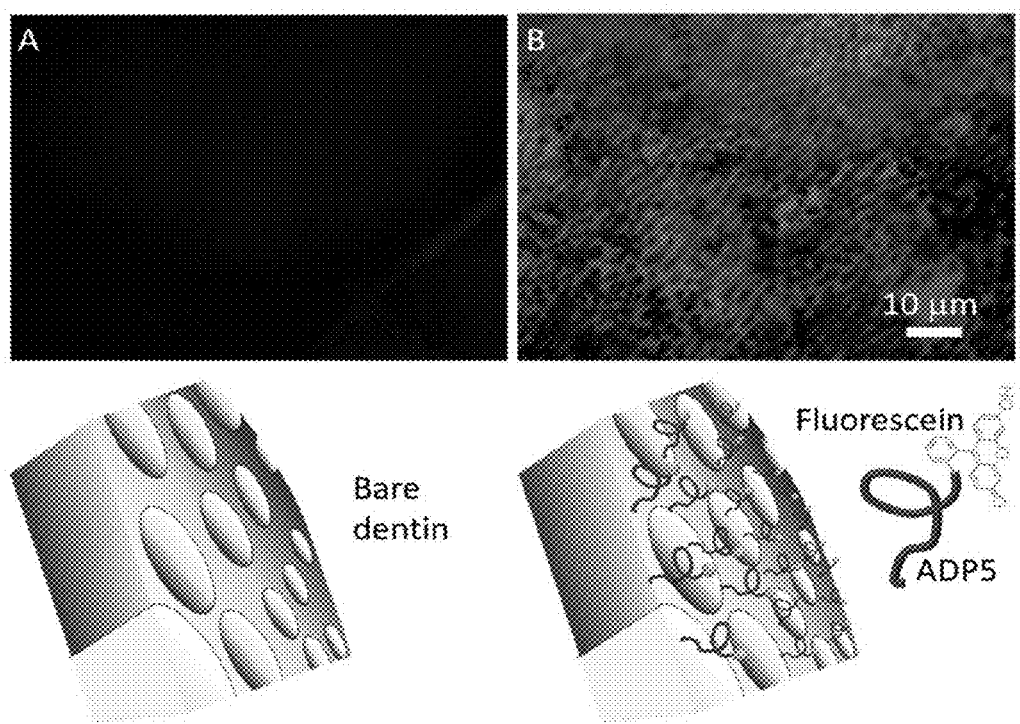
FIG. 7. Fluorescence microscopy images of the root surfaces coated with no peptide (a) and f-ADP5 (b)

Human cementum discs were prepared as described in "Materials and Methods" and as illustrated in FIG. 3. Fluorescent microscopy analysis with fluorescein-labeled ADP5 (fADP5) showed that the ADP5 readily adsorbs on the demineralized surface of human root stock cementum and remains on the surface after extensive washing. Since the microscope was calibrated to the emission of the control samples, the background emission was eliminated in both samples. The human samples after cleaning and etching reveal the expected dentinal tubules characteristic of the dentinoenamel junction, with diameters about 1 µm are clearly visible on the f-ADP5 coated samples (See Supporting Information, FIG. 7)

Figure 4:
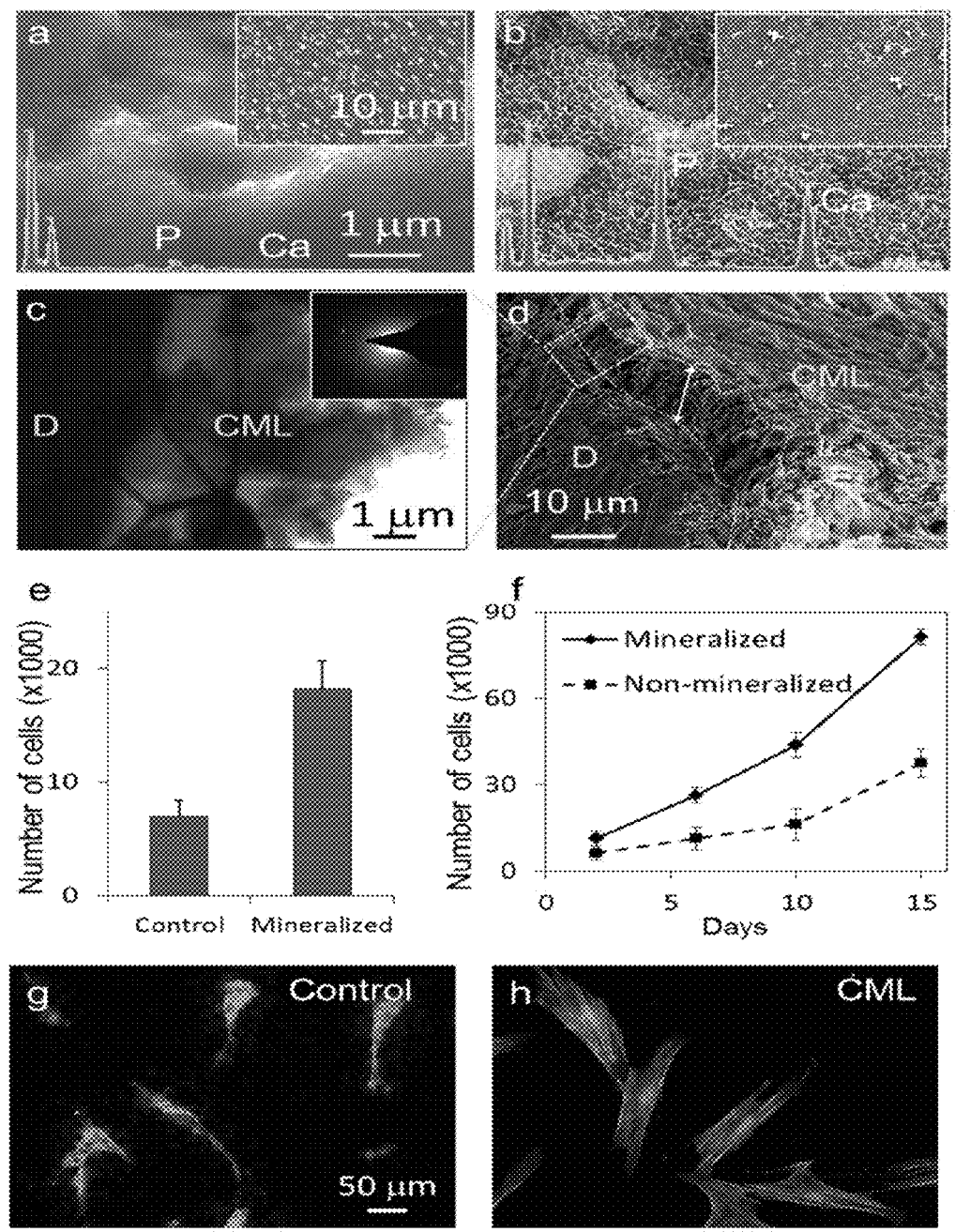
FIG. 4. Structural and functional characteristics of the cementomimetic layer formed on the root of human tooth by ADP5. Panels a and b, SEM images of the demineralized (a) and (b) ADP5 formed cementomimetic layer revealing uniform nanocrystals with a Ca/P ratio of 1.67 obtained from EDX (Energy dispersive X-ray) spectra (insets). Panel c, TEM images and the electron diffraction pattern of the newly formed cementomimetic mineral layer in cross-section showing HAp crystallites. Panel d, SEM image of mechanically separated cementomimetic mineral layer displaying uniform thickness of HAp crystallites; Panel e, Attachment of hPDL cells on control and cementomimetic mineral layer. Panel f, Proliferation of the hPDL cells on control, uncoated, root stock compared to ADP induced cementomimetic mineral layer. Panels g and h, Fluorescent microscopy image showing F-actin. Cell attachment without formation of organized actin network on control surface (g) is compared to those on ADP-induced cementomimetic mineral layer that reveals a well-organized actin cytoskeleton and lamellapodia (h).
Figure 5:
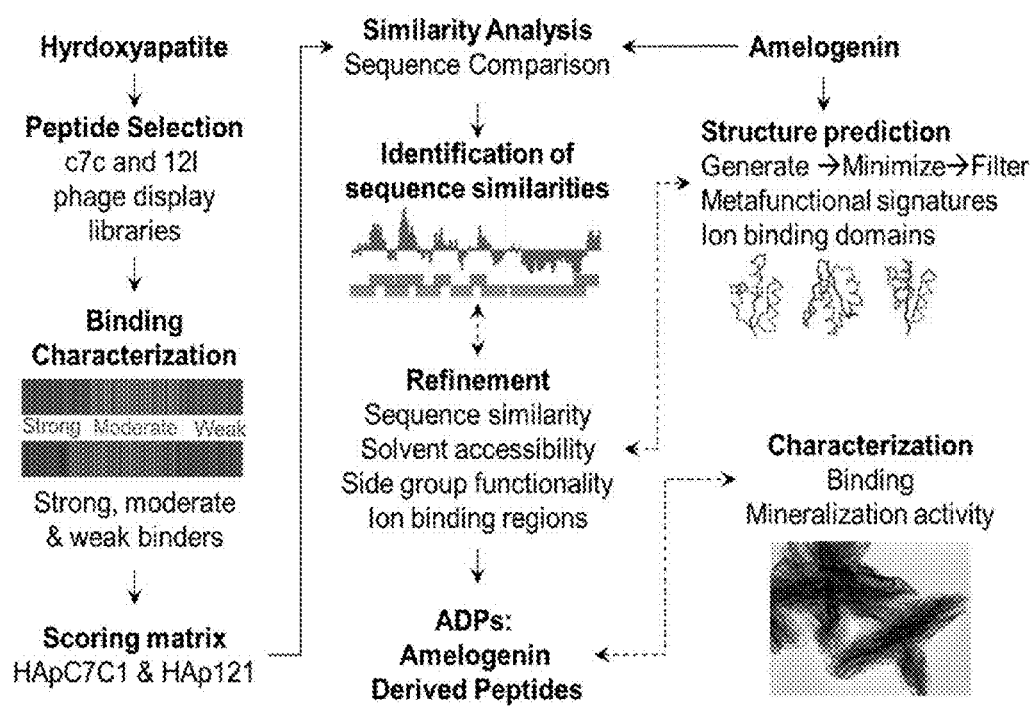
FIG. 5. Procedure for designing amelogenin derived peptides

ADP5 resulted in a substantial difference in the re-mineralization profiles of the human root stock cementum surface as observed via SEM and energy-dispersive x-ray spectroscopy (EDXS) analysis. At the end of 2 hours, no substantial re-mineralization occurred on the control samples consisting of no peptide coating (FIG. 4a). On the other hand, a continuous layer of mineral covering the whole surface of the specimen was observed on the ADP5 coated specimens (FIG. 4b). The morphology of the newly formed mineral was plate-like crystals growing out of the surface of the underlying dentine. Elemental composition analysis by EDS showed no observable Ca or P peaks from the control sample containing no peptide, where, in contrast, substantial Ca and P peaks were observed from the ADP5 coated samples (FIG. 4a,b inserts, respectively). Both SEM and TEM cross-sectional analysis showed that ADP5 yielded a 10-15 µm thick mineral layer that appears to be well integrated with the underlying dentin (FIG. 4c,d). Moreover, the thickness of the cell-free biomimetic cementum layer compares well to the thickness of native human acellular cementum.

Mechanical Properties of the Cementomimetic Layer

As shown in Table 2, the cementomimetic mineral layer exhibited comparable elastic modulus and hardness to the native human cementum (35). The large standard deviation observed for the cemenotomimetic layer was noted and was likely due to the less homogeneous distribution of mineral than that observed for native mineralized dentin or cementum.

TABLE 2

Mechanical properties of cementomimetic layer as measured by nanoindentation, n = 20 indentations.

|  | $E_r$ (GPa) | H (GPa) |
|---|---|---|
| Cementomimetic Layer | 19 ± 7 | 0.7 ± 0.5 |
| Native Cementum | 15 ± 4 | 0.8 ± 0.3 |
| Mineralized Dentin | 26 ± 3 | 1.0 ± 0.2 |
| Demineralized Dentin | 5 ± 3 | 0.2 ± 0.2 |

Figure 9:
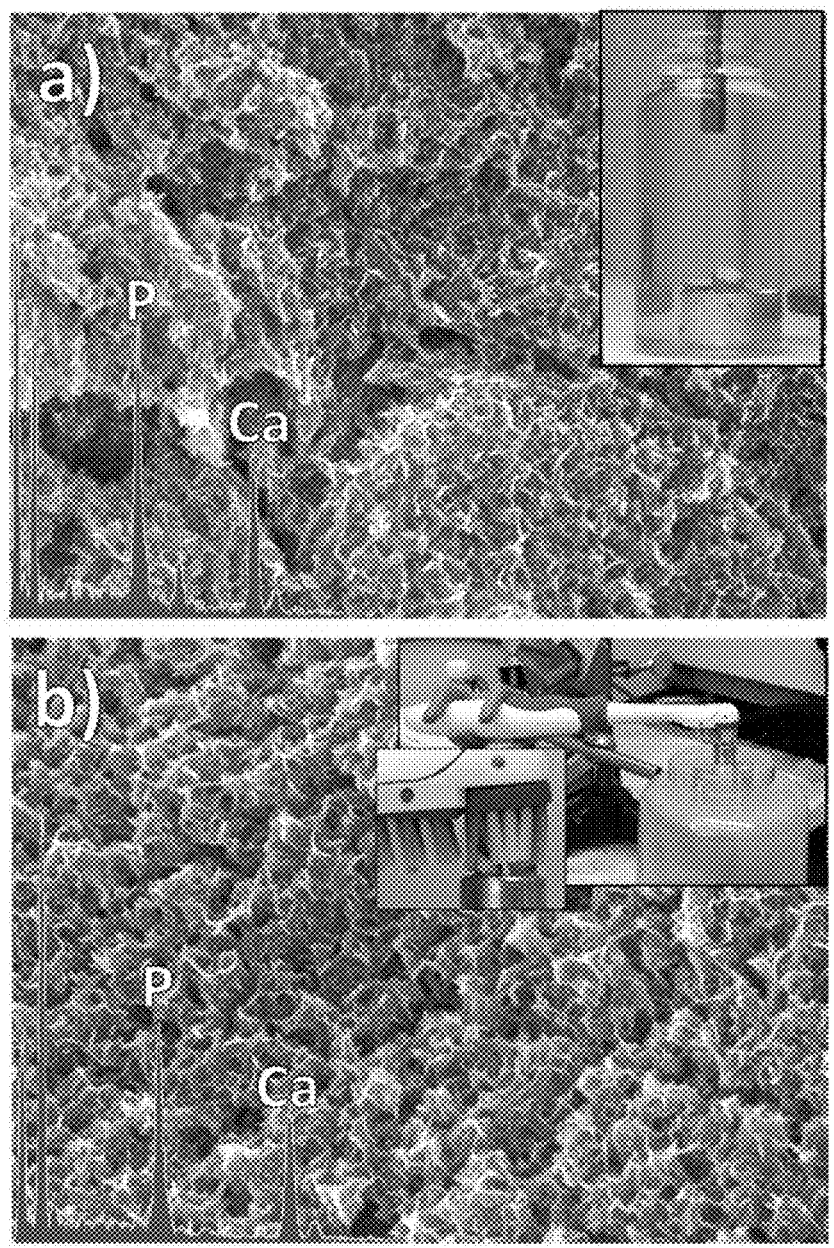
FIG. 9. SEM micrographs and the corresponding EDXS spectra of the cementomimetic layer after qualitative mechanical analysis. a) Ultrasonication and b) brushing. (insets: experimental setups)

We also tested whether the newly formed mineral layer can survive mechanical stresses produced by ultrasonication and mechanical abrasion (brushing). SEM observations showed that the plate-like morphology of the minerals was somewhat distorted after ultrasonication and brushing. However, as confirmed with EDXS, the mineral was still attached to the underlying dentin. (See supplementary information, FIG. 9)

Cell Adhesion and Growth Assays

Cell attachment assays showed that the hPDL cells attach to the mineralized surfaces more effectively compared to their non-mineralized control surfaces. Quantification of cells recovered after 2 hours adhesion period showed that 23.2% of the cells were adherent on the non-mineralized control surface whereas 60.6% of the cells adhered to the biomimetic mineralized surface after 2 hours of incubation. (FIG. 4e)

Proliferation assays showed that the hPDL cells grow more efficiently on the biomimetic mineralized surfaces compared to non-mineralized control surfaces. At the end of 15 days, hPDL cells have reached more than twice the number cells on the biomimetic mineralized surfaces compared to the control surface (FIG. 4f). This data suggests that the cementomimetic mineral layer provides both a favorable environment for the hPDL cells to attach and to proliferate. Fluorescence imaging showed that, after initial adhesion, the cells organize their cytoskeleton on the mineral layer better (FIG. 4h) than the same cells growing on control surfaces (FIG. 4g).

Discussion

The quantitative diffraction and microscopy analyses of the minerals produced by the ADPs revealed that, among the designed peptides, only ADP7, the longest of the similarity regions, and native rM180 produced needle-like-, crystalline-HAp particles, while the others formed crystalline spherulite particles (FIG. 2c-e). Interestingly, although the N-terminal ADP5, which revealed no binding affinity to HAp, exerted a kinetic control over calcium phosphate nucleation at a level similar to full length rM180 amelogenin protein (FIG. 2b). The fact that the ADP5 did not demonstrate a high affinity to HAp indicates that control over nucleation is governed by interactions with precursor ions.

Taken together, these data indicate that the strong binding affinity by a peptide to its mineral substrate, does not necessarily always translate into mineralization directing activity. The fact that the ADP5 showed no significant binding affinity towards HAp but resulted in faster kinetics implies that the ADP5 might be interacting with the soluble precursor ions rather than the mineral surface. The two adjacent pairs of oppositely charged residues at positions 9-10 and 19-20 within ADP5 may be responsible for attracting soluble $Ca^{2+}$ and $PO_4^{-3}$ and creating an increased local super-saturation and thereby, decreasing the nucleation barrier. In contrast, the strong interaction between ADP7 with the mineral surface indicates that a change in the mineral-solution interfacial energy is responsible for the observed mineralization behavior. It has been reported that biomolecules, such as citrate, can alter the interfacial energy of kinetically favorable meta-stable calcium phosphate phases and trigger the phase transformation towards thermodynamically favorable HAp (41, 42). A similar effect may be responsible, due to the relatively high affinity of ADP7 to the mineral surface. Binding of a peptide on a crystal surface is determined by both the conformation (side chain availability) of the peptide and the atomic configuration of the crystal at the binding interface (43-45). We speculate that the formation of HAp instead of other metastable CaP phases, such as ACP, OCP or TCP, in the presence of ADP7 is due to a specific conformation of the peptide and the arrangement of Ca and P sites on the crystal surface that maximizes the binding energy and, in turn, reduces the interfacial energy barrier required to overcome phase transformation.

In summary, the binding and biomineralization behaviors of ADP5, ADP7 and the rM180 imply an interesting mechanism for amelogenin mediated biomineralization during the formation of enamel. The fact that two different amelogenin derived peptides emulate different aspects of the mother protein brings up the question whether these peptides might be different functional regions within amelogenin. Namely, ADP5 may be the region responsible for increased mineralization kinetics through increasing local super-saturation and ADP7 may be the region responsible for favoring the phase transformation towards HAp through altering the interfacial energy. However, the answers to these questions are the focus of another ongoing study.

The range of characteristics exhibited by these individual ADPs represents potential molecular agents to consider for engineering and biomedical applications involving hard tissue repair and replacement where specific control features for the mineral phase are desired. Peptide-assisted re-mineralization of dental tissue defects offers a significant potential for clinical use. Toward this end, we asked whether or not the biomimetic cementum-like mineral layer has a favorable effect on cell behavior, in vitro. Cultured human periodontal ligament cells (hPDL) were selected for investigation since these are the predominant cell types that root surfaces are exposed to in vivo, and further, these cells, when appropriately triggered, can carry on important functions in the repair and regeneration of periodontal tissues (46-50). Cell adhesion and cell proliferation assays, performed on the surface of ADP5 mediated cementum-like tooth material in the absence of serum-derived factors, showed that the nanostructured mineral layer favors both the adhesion and proliferation of cells derived from the periodontium (FIG. 4e, f).

In conclusion, the work described here has several significant implications in peptide-assisted biomineralization. First, we describe a new protocol for identifying peptide sequences from among native proteins associated with HAp containing tissues that are critical to their control over biomineralization. A similar analysis of extracellular matrix proteins associated with biominerals formed by unicellular organisms (e.g., magnetotactic bacteria), invertebrate (sponges, mollusks) and vertebrate animals can reveal other unique amino acid domains that regulate the mineral formation and growth for each of their variety inorganic compounds (magnetite, silica and calcium carbonate) (51). Biomineralization is fundamental to many living organisms and the range of precipitated minerals reflects the elements of the periodic table. Elaborating the mechanism for protein control over the biominerals formed in these systems will afford new insights into the evolution of protein to mineral interactions (52). In the case of enamel, amelogenin is a member of the class of intrinsically disorganized proteins (53). By restricting a structural analysis to but a small domain of a larger protein, such as that defined by ADP5, it is possible to expand our understanding of structure-function relationships, portending the capacity to decipher a relationship between a peptide and a chemical precipitate, and then to use such information for their practical utility to engineer material formation technologies (e.g., bio-manufacturing). Secondly, as demonstrated in this study, strong binding affinity of a peptide to an inorganic solid is not necessarily an indication of its mineral formation capability. Thirdly, the cementomimetic layer formed by ADP5 has a clinical application potential to repair diseased root surfaces, both those caused by caries and periodontal disease, and to promote regeneration of periodontal tissue, reducing the morbidity associated with tooth loss.

REFERENCES FOR EXAMPLE 1

1. Lowenstam H A, Weiner S. *On Biomineralization*. Oxford University Press: New York, 1989.
2. Mann S. *Biomineralization: Principles and Concepts in Bioinorganic Materials Chemistry*. Oxford University Press: New York, 2001.
3. Boskey A, Spevak L, Tan M, Doty S B, Butler W T. Dentin sialoprotein (DSP) has limited effects on in vitro apatite formation and growth. *Calcified Tissue Int* 2000 December; 67(6): 472-478.
4. He G, Dahl T, Veis A, George A. Dentin matrix protein 1 initiates hydroxyapatite formation in vitro. *Connective Tissue Research* 2003; 44: 240-245.
5. Gajjeraman S, Narayanan K, Hao J J, Qin C L, George A. Matrix macromolecules in hard tissues control the nucleation and hierarchical assembly of hydroxyapatite. *Journal of Biological Chemistry* 2007 January; 282(2): 1193-1204.
6. Lowenstam H A. Minerals Formed by Organisms. *Science* 1981; 211(4487): 1126-1131.
7. Taubman M A, Valverde P, Han X Z, Kawai T. Immune response: The key to bone resorption in periodontal disease. *Journal of Periodontology* 2005 November; 76(11): 2033-2041
8. Goldberg H A, Warner K J, Li M C, Hunter G K. Binding of bone sialoprotein, osteopontin and synthetic polypeptides to hydroxyapatite. *Connective Tissue Research* 2001; 42(1): 25-37.
9. Gu L S, Kim Y K, Liu Y, Takahashi K, Arun S, Wimmer C E, et al. Immobilization of a phosphonated analog of matrix phosphoproteins within cross-linked collagen as a templating mechanism for biomimetic mineralization. *Acta Biomater* 2011 January; 7(1): 268-277.
10. Kim J, Arola D D, Gu L S, Kim Y K, Mai S, Liu Y, et al. Functional biomimetic analogs help remineralize apatite-depleted demineralized resin-infiltrated dentin via a bottom-up approach. *Acta Biomater* 2010 July; 6(7): 2740-2750.
11. Capriotti L A, Beebe T P, Schneider J P. Hydroxyapatite surface-induced peptide folding. *J Am Chem Soc* 2007 April; 129(16): 5281-5287.
12. Taller A, Grohe B, Rogers K A, Goldberg H A, Hunter G K. Specific adsorption of osteopontin and synthetic polypeptides to calcium oxalate monohydrate crystals. *Biophys J* 2007 September; 93(5): 1768-1777.
13. Wazen R M, Tye C E, Goldberg H A, Hunter G K, Smith C E, Nanci A. In vivo functional analysis of polyglutamic acid domains in recombinant bone sialoprotein. *Journal of Histochemistry & Cytochemistry* 2007 January; 55(1): 35-42.
14. Zhang S F, Gangal G, Uludag H. 'Magic bullets' for bone diseases: progress in rational design of bone-seeking medicinal agents. *Chemical Society Reviews* 2007; 36(3): 507-531.
15. Tye C E, Rattray K R, Warner K J, Gordon J A R, Sodek J, Hunter G K, et al. Delineation of the hydroxyapatite-nucleating domains of bone sialoprotein. *Journal of Biological Chemistry* 2003 March; 278(10): 7949-7955.
16. Pampena D A, Robertson K A, Litvinova O, Lajoie G, Goldberg H A, Hunter G K. Inhibition of hydroxyapatite formation by osteopontin phosphopeptides. *Biochem J* 2004 March; 378: 1083-1087.
17. Snead M L, Zhu D H, Lei Y P, White S N, Snead C M, Luo W, et al. Protein self-assembly creates a nanoscale device for biomineralization. *Materials Science & Engineering C-Biomimetic and Supramolecular Systems* 2006 September; 26(8): 1296-1300.
18. Du C, Falini G, Fermani S, Abbott C, Moradian-Oldak J. Supramolecular assembly of amelogenin nanospheres into birefringent microribbons. *Science* 2005 Mar. 4; 307(5714): 1450-1454.
19. Bartlett J D, Ganss B, Goldberg M, Moradian-Oldak J, Paine M L, Snead M L, et al. 3. Protein-protein interactions of the developing enamel matrix. *Curr Top Dev Biol* 2006; 74: 57-115.
20. Iijima M, Moradian-Oldak J. Interactions of Amelogenins with Octacalcium Phosphate Crystal Faces Are Dose Dependent. *Calcif Tissue Int* 2004 Jan. 23.
21. Fan D, Iijima M, Bromley K M, Yang X, Mathew S, Moradian-Oldak J. The cooperation of enamelin and amelogenin in controlling octacalcium phosphate crystal morphology. *Cells Tissues Organs* 2011; 194(2-4): 194-198.
22. Gungormus M, Fong H, Kim I W, Evans J S, Tamerler C, Sarikaya M. Regulation of in vitro calcium phosphate mineralization by combinatorially selected hydroxyapatite-binding peptides. *Biomacromolecules* 2008 March; 9(3): 966-973.
23. Oren E E, Tamerler C, Sahin D, Hnilova M, Seker U O S, Sarikaya M, et al. A novel knowledge-based approach to design inorganic-binding peptides. *Bioinformatics* 2007 November; 23(21): 2816-2822.
24. Moradian-Oldak J, Paine M L, Lei Y P, Fincham A G, Snead M L. Self-assembly properties of recombinant engineered amelogenin proteins analyzed by dynamic light scattering and atomic force microscopy. *J Struct Biol* 2000 July; 131(1): 27-37.
25. Pugach M K, Li Y, Suggs C, Wright J T, Aragon M A, Yuan Z A, et al. The Amelogenin C-Terminus Is Required for Enamel Development. *Journal of Dental Research* 2010 February; 89(2): 165-169.
26. Friddle R W, Battle K, Trubetskoy V, Tao J H, Salter E A, Moradian-Oldak J, et al. Single-Molecule Determination of the Face-Specific Adsorption of Amelogenin's C-Terminus on Hydroxyapatite. *Angewandte Chemie-International Edition* 2011; 50(33): 7541-7545.
27. Shaw W J, Campbell A A, Paine M L, Snead M L. The COOH terminus of the amelogenin, LRAP, is oriented next to the hydroxyapatite surface. *Journal of Biological Chemistry* 2004 September; 279(39): 40263-40266.
28. Aoba T, Moreno E C, Kresak M, Tanabe T. Possible roles of partial sequences at N- and C-termini of amelogenin in protein-enamel mineral interaction. *Journal of Dental Research* 1989 September; 68(9): 1331-1336.
29. Arys A, Jedwab J, Pireaux J J, Philippart C, Dourov N. Brushite in the Pulp of Primary Molars. *Journal of Oral Pathology & Medicine* 1989 August; 18(7): 371-376.
30. Kodaka T, Hirayama A, Mori R, Sano T. Spherulitic brushite stones in the dental pulp of a cow. *Journal of Electron Microscopy* 1998; 47(1): 57-65.
31. Achilles W, Jockel U, Schaper A, Burk M, Riedmiller H. In-vitro Formation of Urinary Stones—Generation of Spherulites of Calcium-Phosphate in Gel and Overgrowth with Calcium-Oxalate Using a New Flow Model of Crystallization. *Scanning Microscopy* 1995 June; 9(2): 577-586.
32. Margolis H C, Beniash E, Fowler C E. Role of macromolecular assembly of enamel matrix proteins in enamel formation. *Journal of Dental Research* 2006 September; 85(9): 775-793.
33. Beniash E, Simmer J P, Margolis H C. The effect of recombinant mouse amelogenins on the formation and 34. Fan Y, Sun Z, Moradian-Oldak J. Controlled remineralization of enamel in the presence of amelogenin and fluoride. *Biomaterials* 2009 February; 30(4): 478-483.
35. Ho S P, Yu B, Yun W, Marshall G W, Ryder M I, Marshall S J. Structure, chemical composition and mechanical properties of human and rat cementum and its interface with root dentin. *Acta Biomater* 2009 February; 5(2): 707-718.
36. Moradian-Oldak J, Paine M L, Lei Y P, Fincham A G, Snead M L. Carboxy- and amino-terminal domains of amelogenin are involved in the supramolecular self-assembly. *Journal of Dental Research* 2000; 79: 513-513.
37. Paine M L, Luo W, Zhu D H, Bringas P, Snead M L. Functional domains for amelogenin revealed by compound genetic defects. *Journal of Bone and Mineral Research* 2003 March; 18(3): 466-472.
38. Snead M L. Amelogenin protein exhibits a modular design: Implications for form and function. *Connective Tissue Research* 2003; 44: 47-51.
39. Dunglas C, Septier D, Paine M L, Snead M L, Goldberg M. Ultrastructure of forming enamel in mouse bearing a transgene that disrupt amelogenin assembly domains. *Journal of Dental Research* 2001 April; 80(4): 1278-1278.
40. Le Norcy E, Kwak S Y, Wiedemann-Bidlack F B, Beniash E, Yamakoshi Y, Simmer J P, et al. Potential Role of the Amelogenin N-Terminus in the Regulation of Calcium Phosphate Formation in vitro. *Cells Tissues Organs* 2011; 194(2-4): 188-193.
41. Qiu S R, Wierzbicki A, Orme C A, Cody A M, Hoyer J R, Nancollas G H, et al. Molecular modulation of calcium oxalate crystallization by osteopontin and citrate. *Proc Natl Acad Sci USA* 2004 February; 101(7): 1811-1815.
42. Jiang W G, Chu X B, Wang B, Pan H H, Xu X R, Tang R K. Biomimetically Triggered Inorganic Crystal Transformation by Biomolecules: A New Understanding of Biomineralization. *Journal of Physical Chemistry B* 2009 August; 113(31): 10838-10844.
43. Elangovan S, Margolis H C, Oppenheim F G, Beniash E. Conformational changes in salivary proline-rich protein 1 upon adsorption to calcium phosphate crystalsle. *Langmuir* 2007 October; 23(22): 11200-11205.
44. Masica D L, Gray J J. Solution- and Adsorbed-State Structural Ensembles Predicted for the Statherin-Hydroxyapatite System. *Biophys J* 2009 April; 96(8): 3082-3091.
45. So C R, Tamerler C, Sarikaya M. Adsorption, Diffusion, and Self-Assembly of an Engineered Gold-Binding Peptide on Au(111) Investigated by Atomic Force Microscopy. *Angewandte Chemie-International Edition* 2009; 48(28): 5174-5177.
46. Nagatomo K, Komaki M, Sekiya I, Sakaguchi Y, Noguchi K, Oda S, et al. Stem cell properties of human periodontal ligament cells. *Journal of Periodontal Research* 2006 August; 41(4): 303-310.
47. Seo B M, Miura M, Gronthos S, Bartold P M, Batouli S, Brahim J, et al. Investigation of multipotent postnatal stem cells from human periodontal ligament. *Lancet* 2004 July; 364(9429): 149-155.
48. Seo B M, Miura M, Sonoyama W, Coppe C, Stanyon R, Shi S. Recovery of stem cells from cryopreserved periodontal ligament. *Journal of Dental Research* 2005 October; 84(10): 907-912.
49. Gay I C, Chen S, MacDougall M. Isolation and characterization of multipotent human periodontal ligament stem cells. *Orthodontics & Craniofacial Research* 2007 August; 10(3): 149-160.
50. Ivanovski S, Gronthos S, Shi S, Bartold P M. Stem cells in the periodontal ligament. *Oral Diseases* 2006 July; 12(4): 358-363.
51. Lowenstam H A, Weiner S. *On biomineralization.* Oxford University Press: New York, 1989, ix, 324 p.pp.
52. Sarikaya M, Aksay I A. *Biomimetics: design and processing of materials.* AIP Press: Woodbury, N. Y., 1995, xi, 285, [284] of platespp.
53. Laksminarayanan R, Bromley K M, Lei Y P, Snead M L, Moradian-Oldak J. Perturbed amelogenin secondary structure leads to uncontrolled aggregation in amelogenesis imperfecta mutant proteins. *J Biol Chem* October 7.

Supporting Material for Example 1
Combinatorial Selection of Peptides

Commercially available Ph.D. Phage Display Peptide Library Kits (c7c and 12) were used as the biocombinatorial library (New England BioLabs Inc., USA) and synthetic HA powder was used as the target substrate (a generous gift from Ivan Transevica Institute, Department of Materials Science, Ukraine). Prior to exposing to the peptide-phage library, the HA powder was cleaned by ultrasonication in a 1/1 methanol/acetone mixture followed by ultrasonication in isopropanol. Cleaned HA powder was incubated with the phage-peptide library overnight in a potassium phosphate/sodium carbonate (PC) buffer (pH 7.4), containing 0.1% detergent (Tween 20 and Tween 80, Merck, USA) at room temperature with constant rotation. The detergent prevents non-specific interactions between phage particles and enables individual phage particle to powder surface interaction to occur. After incubating the HAp powder substrate with the phage library, the powder was washed several times with PC buffer containing 0.1% detergent to remove any non-specifically or weakly bound phage particles from the HA surface. The phages remaining on the HA surface were then eluted by 0.2 M Glycine HCl (pH 2.2) solution, followed by ultrasonication. Eluted phage were transferred to an early-log phase *E. coli* ER2738 culture and amplified for 4 hours. The amplified phage are isolated by polyethylene glycol (PEG) precipitation. After the third round of panning, the phage obtained from each round of selection are plated on LB-Agar media containing 5-bromo-4-chloro-3-indolyl-β-D-galactopyranoside (Xgal) and isopropyl-β-D-thiogalactopyranosid (IPTG) in serial dilutions to obtain single phage plaques. Since ER2738 strain lacks the lacZα gene, only the cells infected by M13mp 19 bacteriophage, carrying the lacZα gene can produce β□□galactosidase and provide a chromogenic change in color when exposed to Xgal. Therefore, infected cells can hydrolyze X-Gal and form blue phage plaques. After growing the phages on LB-Agar plates, single blue plaques containing clonal expanded phage particles were picked, amplified and the amino acid sequence of the corresponding polypeptide segment was identified by DNA sequencing.

Semi-quantitative Analysis of HA Binding

The binding affinity of each clone was assessed by immunofluorescence fluorescence microscopy and enzyme-linked immunosorbent assay (ELISA). For the fluorescence microscopy, cleaned HAp powder was incubated overnight with selected monoclonal phages at $10^{11}$ PFU/mL concentration in PC buffer containing 0.1% detergent at room temperature and with constant rotation. Wild type M13mp19 bacteriophage with no random peptides displayed on the pIII protein was used as negative control. After incubation, the powder was washed three times with the same buffer. After the washing, the phage remaining bound to the surface are labeled with mouse anti-M13 IgG (Amersham Biosciences, USA) and Alexa Fluor 488-anti-mouse IgG2a conjugate (Invitrogen Corporation, USA). After labeling, the powder suspension was transferred to a microscope slide and observed using a TE 300L microscope (Nikon, Japan). The approximate surface coverage of the phage particles was calculated using MetaMorph Imaging System Ver. 6.2 (Photometrics UK Ltd., UK, formerly Universal Imaging Co., USA) by comparing the approximate surface area of the powder in the bright field image to the approximate phage coverage in the fluorescence image.

For ELISA analysis, cleaned HAp powder was incubated overnight with selected monoclonal phages at $10^{11}$ PFU/ml concentration in PBS buffer containing 2% BSA at room temperature with constant rotation. Wild type M13mp 19 bacteriophage, displaying no peptides on the p(III) protein, was used as negative control. The powder was washed 3 times with PBS buffer containing 0.05% detergent. After the washing, the bound phages on the surface were labeled with horseradish peroxidase (HRP)-anti-M13 IgG conjugates (Amersham Biosciences, USA) in PBS buffer containing 2% BSA for 30 minutes with constant rotation and washed 4 times with PBS buffer. The reaction ready HRP substrate 3,3',5,5' tetramethylbenzidine (TMB)-ELISA (Pierce, USA) was added into the solution. The oxidation of the TMB by HRP yields a diimine form of TMB. The reaction was stopped after 2 minutes by adding 1 M $H_2SO_4$, which results in a yellow color with maximum absorbance at 450 nm. The optical density (OD) of the reaction solution was measured at 450 nm wave length using a microplate reader (Tecan Trading AG, Switzerland).

TABLE 3

Number of the characterized peptides from the 7 amino acids cyclic (c7c) and 12 amino acids linear phage-peptide libraries.

| | Strong | Moderate | Weak | Total |
|---|---|---|---|---|
| PhD c7c | 12 | 27 | 18 | 57 |
| PhD 12 | 16 | 20 | 13 | 49 |

Protein Structure Prediction

Contemporary protein structure prediction methods use known structures as variable length templates for construction assembly. We have developed an initial set of incomplete structure alignments in the form of meta-predictions using 3D-Jury (web site /bioinfo.pl/meta) (1). and incorporated these as templates for the development of many full length models using the Protinfo protein structure prediction protocol (web site protinfo.compbio.washington.edu/protinfo_abcmfr) (2) (RAMP: A suite of programs to aid in the modeling of protein structure and function (web site compbio.-washington.edu/ramp/) (3). In addition we have retrieved the full-length models from the I-TASSER server (web site zhang.bioinformatics.ku.edu/I-TASSER) (4). Next, we have used an all-atom conditional probability discriminatory function, RAPDF (5), to select the best models. These models were iteratively refined using template-, geometry- and physics-based methods included within the RAMP suite (3).

We used RAPDF to select the best five models among all of the decoys created for the full-length M180 amelogenin. We then have picked the best combination of regions from the top 5 models, using a graph-theoretic clique finding approach, in the creation of an optimized conformation model (6).

$Ca^{2+}$ Ion Binding Domain Predictions

We have performed an exhaustive grid-based search placing ions into all solvent exposed sites in the 3D structure. The sites were scored with a grid based exhaustive sampling algorithm, clustered using a variant of an unsupervised hierarchy clustering algorithm, and refined with Monte Carlo minimization. The scoring function was developed from geometrical parameters observed for inorganic single atom ions coordinating small molecule organics found in many crystallography structures publicly available through the PDB (7). This scoring function was verified by accurately ranking the binding affinities between proteins and ions, predicting the naturally occurring ion binding sites of proteins and recovering the native conformation of protein-substrate binding (web site protinfo.compbio.washington.edu/soak) (8)

Metafunctional Signatures

The Meta-Functional Signature (MFS) method comprises five sub-scores. The compilation of these scores was trained on two databases of functionally important residues (9) using a simple logit model (web site protinfo.compbio.washington.edu/mfs). (10-12) The MFS method can also be applied without structural analysis, using only scores based on sequence information, hidden Markov model (HMM), State-to-Step Ratio (SSR), and amino acid type (AA_type), to produce highly accurate identification of amino acids known to be important to function. (10)

SSR—The evolutionary context for a region is modeled by creating a phylogenetic tree for the sequence surrounding each amino acid in a protein, using multiple sequence alignments of PSI-BLAST results (13). The root of the tree represents the theoretical ancestral sequence, while each leaf of the tree represents a PSI-BLAST result sequence. We quantify the evolutionary divergence of each amino acid from its evolutionary context through the phylogenetic tree. SSR describes the ratio of the number of different amino acids presenting at a position across the multiple sequence alignments, to the total number of changes between the input protein and the base sequence within the phylogenetic tree. (10) HMM—We have compiled a HMM from the multiple sequence alignments described above, using the HMMER package (14). We then have compared emission frequency estimates from the HMM model with the amino acid background frequency given by karlin.c of the BLAST program package (13), to produce the HMM relative entropy score for each amino acid position (15). AA_type—We have assigned a simple score to each amino acid type, developed from the frequency of each amino acid type appearing within active sites in two large databases. Structural Stability scores—virtual mutations—We have evaluated the importance of each residue to the structural stability of the protein by performing a series of virtual mutations to the 19 alternate amino acids, modeling induced changes in tertiary structure, and comparing simulated energy function scores (RAPDF; (5)) for the mutation set for each residue. RAPDF_spread, the variation of RAPDF scores across all possible mutants for the residue, indicates the structural volatility of the position, and therefore the contribution of the position to stability. The RAPDF_dif structural stability score represents the sum of the simple differences between the RAPDF score for the input structure and all 19 alternatives, which indicates the effect of the naturally occurring amino acid identity on stabilization of the structure (11). The structural stability score was implemented both within MFS and used separately for identifying fold bearing regions not likely to contribute to function but may create specific conformations important to function for the regions they span.

In vitro Solution Biomineralization

To investigate the effect of peptides on in vitro calcium phosphate nucleation, an alkaline phosphatase (AP) based mineralization model was used. (16) This model mimics the biological matrix vesicle mediated mineralization, where inorganic phosphate is cleaved from an organic phosphate compound by AP and reacts with calcium inside the matrix vesicle. Prior to the mineralization experiments the activity of AP was measured in the presence of the peptides, to assess the effects of either peptide on the enzyme activity. β-Glycerophosphate (β-GP) solutions at 14.4 mM containing no peptide and 0.4 mM peptides were prepared in 25 mM Tris-HCl buffer (pH 7.4). The reaction was started by adding $1.4 \times 10^{-6}$ g/mL bacterial AP (Invitrogen, U.S.A.) to the solution. The reaction was carried at 37° C., and samples were collected at times 0.25-, 1-, 3-, 16- and 24-hr. The phosphate released in each solution was measured using PiPer Phosphate Assay Kit (Invitrogen Co., U.S.A.) and plotted against time.

For the mineralization experiments, mineralization solutions containing 24 mM $Ca^{2+}$ and 14.4 mM β-GP and 0.4 mM peptide was prepared in 25 mM Tris-HCl buffer (pH 7.4). A mineralization solution containing no peptide was prepared as the negative control. Mineralization reactions were commenced by adding bacterial AP to the solution at a final concentration of $1.4 \times 10^{-6}$ g/mL. Subsequent mineral formation kinetics was monitored by continuous measuring of absorbance at 820 nm wave length using a Tecan Safire microplate reader (Tecan Trading AG, Switzerland) as well as by periodic assays of calcium ions throughout the reaction. For periodic assays of calcium and phosphate, 10 μL of the reaction solution was collected at 0.25-, 0.5-, 1- and 1.5-hr. The calcium concentration in the solutions was determined using QuantiChrome Calcium Assay Kit (Bioassays, U.S.A.). All mineralization reactions were carried out at 37° C. Samples for electron microscopy analysis were prepared by placing a 10 μL aliquot from the reaction solution onto a carbon coated TEM grid. After 1 min, liquid on the TEM grid was carefully wicked away and the grids were vacuum-dried for 5 min. The dried grids were stored in a desiccated container until analyzed. SEM imaging was performed at 10 kV using a JSM 7000F (JEOL, Japan) SEM in secondary electron imaging mode. TEM imaging and electron diffraction analysis were performed using an EMS 420T TEM (FEI, Inc., USA; formerly Philips, The Netherlands) operated at 120 kV.

Figure 2:
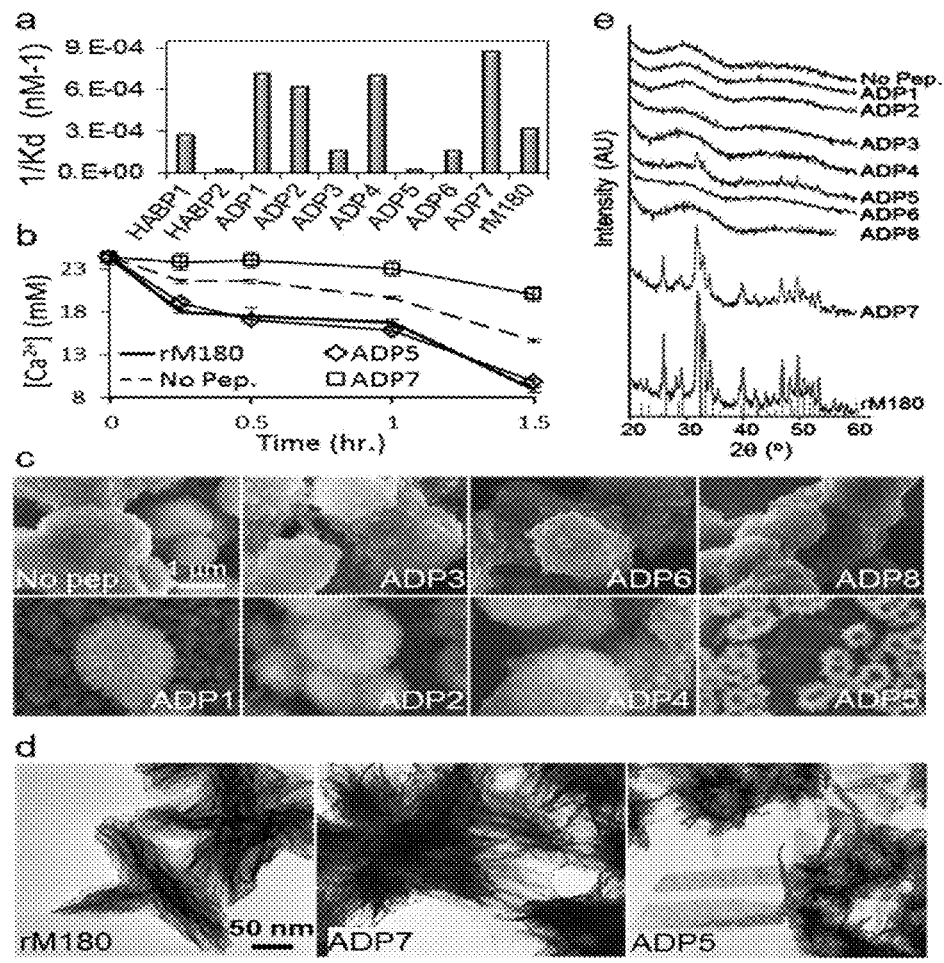
FIG. 2. Binding, mineralization, and structural characterization of mineral products of the ADPs. Panel a, Binding constants, K$_D$, of the ADPs determined by QCM. Panel b, Calcium consumption rates of mineralization in the presence of ADP5,7 and rM180. Panel c, Calcium phosphate minerals formed in solution in the presence of ADPs. Panel d, The mineral product of ADP7 resembles those formed in the presence of rM180 and these acicular crystallites are consistent with HAp morphology. Panel e, X-ray diffraction (XRD) spectra of the minerals formed by ADPs. Material formed by ADP7 and amelogenin display the characteristic peaks belonging to the HAp crystal structure, while all minerals formed by other ADPs display weak diffraction peaks, consistent with amorphous, or only loosely crystalline outcomes shown in panel c.
Figure 6:
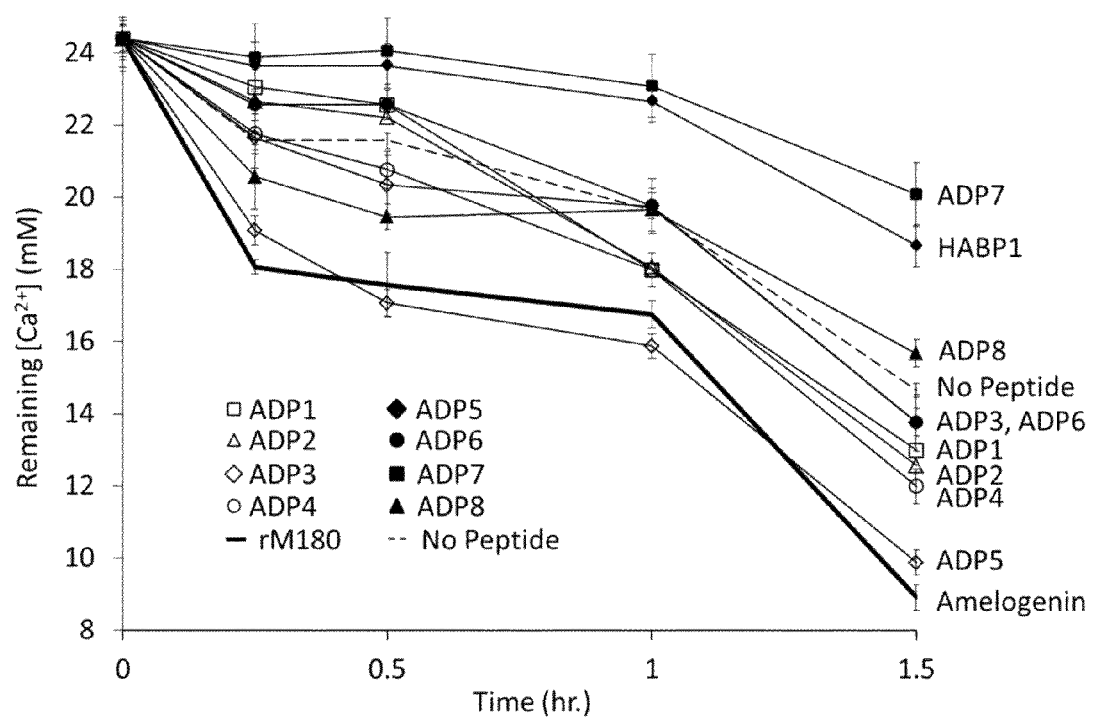
FIG. 6. $Ca^{+2}$ consumption rates of the ADPs for the initial 90 minutes

We noted that there were three distinct trends of mineralization among the tested ADPs. (FIG. 2) The majority of the peptides (ADP1, ADP2, ADP3, ADP4, ADP6 and ADP8) exhibited similar kinetics to the negative control, where no peptide was present. The phage display selected HABP1 and the ADP7 exhibited a slow mineralization trend. Interestingly, full-length rM180 and the ADP5 exhibited a fast mineralization trend where more than half of the available free $Ca^{2+}$ was consumed at the end of the 90 minutes (FIG. 6). The microstructural and crystallographic analysis of the synthesized minerals via SEM, TEM and XRD revealed another interesting consequence regarding the relationship between the mineral binding and mineralization activity. Similar to the mineralization kinetics, three distinct trends of mineral morphologies were observed. The majority of the peptides (ADP1, ADP2, ADP3, ADP4, ADP6, ADP8 and HABP1) produced spherulitic particles consistent with the formation of spherical amorphous calcium phosphate (ACP) and transformation into crystalline phases. (17-19) The amount of the radiating crystalline blade like particles from the spherulites were slightly higher for ADP1, ADP2, ADP4 and HABP1 (strong binders) compared to ADP3, ADP6, ADP8 (weak binders) and no peptide, an order indicating that the amorphous to crystalline transformation rates were slightly different. In the case of rM180 and ADP7, however, a completely different morphology was observed. Needle like nano-crystals were organized into bundle-like assemblies observed for rM180 and ADP7. The bundle-like assemblies appeared to be better organized in the case of rM180, which is consistent with the self-assembly properties of amelogenin and the in vitro mineralization behavior of recombinant amelogenin (20-22). The particles formed in the presence of ADP5 were much smaller spherulites with a less electron-dense core and smaller radiating crystals. The smaller particles sizes in the presence of ADP5 may be due to its nucleation dominated regime, as observed from in data describing the mineralization kinetics. The crystallographic analysis via XRD spectroscopy also confirmed the morphological differences were due to different crystal structure. In all cases except for rM180 and ADP7, the minerals yielded a broad peak around 2θ 25-30° indicating a poorly crystalline phase. In the presence of rM180 and ADP7, however, the XRD patterns were consisted of numerous sharp peaks indicative of crystalline HAp. The major peaks were observed at 2θ=31.8° (d=2.81 Å) and 32.1° (d=2.78 Å) corresponding to (211) and (300) planes of HAp, respectively. (FIG. 2d)

REFERENCES FOR EXAMPLE 1 SUPPORTING MATERIAL

1. Ginalski K, Elofsson A, Fischer D, Rychlewski L. 3D-Jury: a simple approach to improve protein structure predictions. *Bioinformatics* 2003 May; 19(8): 1015-1018.
2. Hung L H, Ngan S C, Liu T, Samudrala R. PROTINFO: new algorithms for enhanced protein structure predictions. *Nucleic Acids Res* 2005 July; 33: W77-W80.
3. Samudrala R, Xia Y, Huang E, Levitt M. Ab initio protein structure prediction using a combined hierarchical approach. *Proteins-Structure Function and Genetics* 1999: 194-198.
4. Zhang Y. Template-based modeling and free modeling by I-TASSER in CASP7. *Proteins-Structure Function and Bioinformatics* 2007; 69: 108-117.
5. Samudrala R, Moult J. An all-atom distance-dependent conditional probability discriminatory function for protein structure prediction. *Journal of Molecular Biology* 1998 February; 275(5): 895-916.
6. Liu T, Guerquin M, Samudrala R. Improving the accuracy of template-based predictions by mixing and matching between initial models. *Bmc Structural Biology* 2008 May; 8.
7. Berman G P, James D F V, Hughes R J, Gulley M S, Holzscheiter M H, Lopez G V. Dynamical stability and quantum chaos of ions in a linear trap. *Physical Review A* 2000 February; 61(2).
8. Cheng G, Samudrala R. An all-atom geometrical knowledge-based scoringfunction to predict protein metal ion binding sites, affinities and specificities. in preparation.
9. Chelliah V, Chen L, Blundell T L, Lovell S C. Distinguishing structural and functional restraints in evolution in order to identify interaction sites. *Journal of Molecular Biology* 2004 October; 342(5): 1487-1504.
10. Wang K, Horst J A, Cheng G, Nickle D C, Samudrala R. Protein Meta-Functional Signatures from Combining Sequence, Structure, Evolution, and Amino Acid Property Information. *Plos Computational Biology* 2008 September; 4(9).
11. Cheng G, Qian B, Samudrala R, Baker D. Improvement in protein functional site prediction by distinguishing structural and functional constraints on protein family evolution using computational design. *Nucleic Acids Res* 2005; 33(18): 5861-5867.
12. Wang K, Samudrala R. FSSA: a novel method for identifying functional signatures from structural alignments. *Bioinformatics* 2005 July; 21(13): 2969-2977.
13. Altschul S F, Madden T L, Schaffer A A, Zhang J H, Zhang Z, Miller W, et al. Gapped BLAST and PSI-BLAST: a new generation of protein database search programs. *Nucleic Acids Res* 1997 September; 25(17): 3389-3402.
14. Eddy S R. Hidden Markov models and genome sequence analysis. *Faseb Journal* 1998 April; 12(8): 103.
15. Wang K, Samudrala R. Incorporating background frequency improves entropy-based residue conservation measures. *Bmc Bioinformatics* 2006 August; 7.
16. Gungormus M, Fong H, Kim I W, Evans J S, Tamerler C, Sarikaya M. Regulation of in vitro calcium phosphate mineralization by combinatorially selected hydroxyapatite-binding peptides. *Biomacromolecules* 2008 March; 9(3): 966-973.
17. Arys A, Jedwab J, Pireaux J J, Philippart C, Dourov N. Brushite in the Pulp of Primary Molars. *Journal of Oral Pathology & Medicine* 1989 August; 18(7): 371-376.
18. Kodaka T, Hirayama A, Mori R, Sano T. Spherulitic brushite stones in the dental pulp of a cow. *Journal of Electron Microscopy* 1998; 47(1): 57-65.
19. Achilles W, Jockel U, Schaper A, Burk M, Riedmiller H. In-vitro Formation of Urinary Stones—Generation of Spherulites of Calcium-Phosphate in Gel and Overgrowth with Calcium-Oxalate Using a New Flow Model of Crystallization. *Scanning Microscopy* 1995 June; 9(2): 577-586.
20. Beniash E, Simmer J P, Margolis H C. The effect of recombinant mouse amelogenins on the formation and organization of hydroxyapatite crystals in vitro. *J Struct Biol* 2005 February; 149(2): 182-190.
21. Fan Y, Sun Z, Moradian-Oldak J. Controlled remineralization of enamel in the presence of amelogenin and fluoride. *Biomaterials* 2009 February; 30(4): 478-483.
22. Moradian-Oldak J, Paine M L, Lei Y P, Fincham A G, Snead M L. Self-assembly properties of recombinant engineered amelogenin proteins analyzed by dynamic light scattering and atomic force microscopy. *J Struct Biol* 2000 July; 131(1): 27-37.

EXAMPLE 2

Inherent antibacterial properties of the calcium phosphate mineral (Tin-Oo et al., Archives of Orofacial Sciences, 2007. 2: p. 41-44; Ingram, et al., Plastic and Reconstructive Surgery, 1996. 98(6): p. 1119-1119; Owadally, Endodontics & Dental Traumatology, 1994. 10(5): p. 228-232) may also create a less viable environment for bacterial colonization and result in a decrease in bacterial colonization. To test this, preliminary experiments were carried out on the peptide-formed mineral layer with *S. epidermidis*, a potent biofilm forming bacteria. Bacterial viability assays clearly show that the mineral layer exhibits a bactericidal effect (data not shown). In the live/dead assay performed, the live bacteria were stained green, while the dead bacteria were stained red since the red dye can only penetrate compromised cell walls. The percent of the dead bacteria on the mineral layer was much higher than that of on exposed dentin. The total bacterial coverage on the bare dentin and the peptide-formed mineral was 41% and 58% respectively. Although the total bacterial coverage was higher on the mineral layer, 40% of the bacteria were dead, while on bare dentin, only ~6% of the bacteria were dead. The observed effect has significant implications in preventing further infiltration of exposed dentin tubules and arresting tooth resorption. Despite the antibacterial effect, the peptide-formed mineral layer exhibits an opposite effect on eukaryotic cells such as PDL fibroblasts and cementoblasts, as shown above Methods for Example 2

Bacterial Viability Assays

*S. epidermidis* culture was adjusted to an optical density of 1.0 (approximately $1 \times 10^8$ cells/ml) and the cell suspension was placed in all wells with the previously prepared mineralized specimens and non-mineralized control specimens. The bacteria were incubated for 2.5 h at 37° C. Loosely adherent bacteria were removed by gently rinsing the wells three times with PBS. Adherent bacteria were stained using Live/Dead BacLight™ Bacterial Viability stain kit (Invitrogen, USA) according to the manufacturer's protocol. Excess liquid was aspirated from surfaces and cells viewed with an epifluorescent microscope (Zeiss Axioskop 2, Jena, Germany) equipped with an Optronics MagnaFire™ Digital Camera System (Optronics, Goleta, Calif.), a 100× oil immersion objective, and appropriate filters. Five random fields were selected per well and imaged using the Magna-Fire™ software program. Bacteria coverage was quantified with the aid of ImageJ™ software.

EXAMPLE 3

ADP5 Mutations

The two adjacent pairs of oppositely charged residues (E9-K10 and D19-R20) in ADP5 may be responsible for attracting soluble $Ca^{+2}$ and $PO_4^{-3}$ and creating an increased local super-saturation in the proximity of the polypeptide. To further test this assumption and assess the functionality of the polypeptides, we have tested the effect of eliminating the charged residues on mineralization using three mutations where only positively charged, only negatively charged and all charged residues were replaced with alanine (A). The amino acid sequences of the mutant peptides generated are listed in Table 4.

TABLE 4

Amino acid sequences and the calculated physicochemical properties of the ADP5 mutants

| Amino Acid sequence | | M.W. | pI | G.R.A.V.Y. | |
|---|---|---|---|---|---|
| ADP5 | PGYINLSYEKSHSQAINTDRTA | 2465.60 | 7.16 | -0.959 | (SEQ ID NO: 7) |
| ADP5 (+A) | PGYINLSYAKSHSQAINTARTA | 2363.60 | 9.72 | -0.477 | (SEQ ID NO: 38) |

TABLE 4-continued

Amino acid sequences and the calculated physicochemical properties of the ADP5 mutants

| Amino Acid sequence | | M.W. | pI | G.R.A.V.Y. | |
|---|---|---|---|---|---|
| ADP5 (-A) | PGYINLSYEASHSQAINTDATA | 2323.40 | 4.35 | -0.414 | (SEQ ID NO: 39) |
| ADP5 (+,-A) | PGYINLSYAASHSQAINTAATA | 2221.40 | 7.16 | 0.068 | (SEQ ID NO: 40) |

Figure 10:
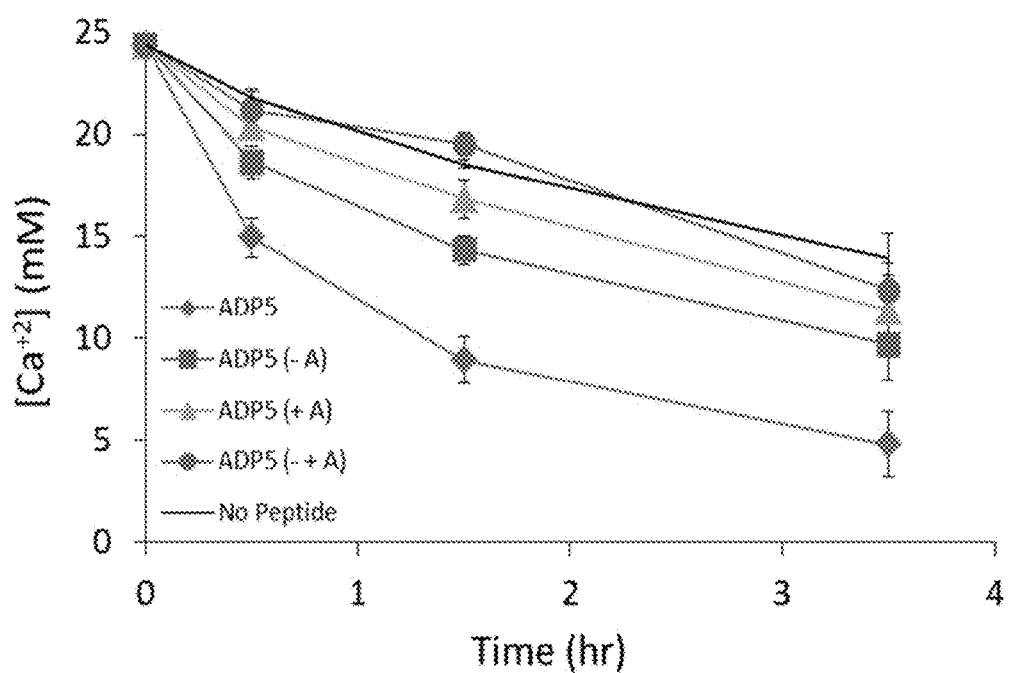
FIG. 10. $Ca^{+2}$ consumption rates of the ADP5 mutants for the initial 3.5 hours.

Adapting the standardized mineralization assays described herein using the mutant ADP5 peptides showed that the oppositely charged adjacent residues indeed play a role in the promotion of nucleation during the biomineralization process. The deletion of both the positively and the negatively charged residues resulted in complete loss of function as observed via calcium depletion assays. Deletion of only positively or negatively charged residues, on the other hand, resulted in a partial loss of function. The promotion of the nucleation was inhibited to a lesser extent when the positively charged residues were deleted and the negatively charged residues were retained (FIG. 10).

As a result of these interactions, we have been able to control the biomineralization process, in particular the rate of reactions. Here we find that ADP5 stands out as a clinically potential peptide where promotion of nucleation may be necessary to provide a rapid mineralization. Furthermore, each mutant now has a different affect for rate of biomineralization. This may be useful if one wants to control this rate, for example, for shape formation of a biomineralized entity.

Fragments of ADP7:

In the case of ADP7, the strong interaction between the polypeptide and the mineral indicate that a change in the mineral-solution interfacial energy is significant in the formation of HA in preference to OCP. The formation of HA is a rather complicated process and can occur via different routes. At pH 9 and above, ACP directly transforms into HA. [1] It is thought that the ACP formed at elevated pH is structurally less defined but more similar to HA compared to those form at lower pH, thus, energetically it is more favorable to transform into HA. [1,2] Below pH 9, however, the transformation is more complicated, where an ACP to OCP transformation precedes an OCP to HA transformation. The ACP particles forming below pH 9 have more defined structures with randomly positioned ordered clusters resembling hydrated OCP-like structures. [1] Therefore, ACP to OCP transformation is more favorable below pH 9. Later, an OCP to HA transformation may occur under the right conditions, mainly by the hydrolysis of the OCP. [3]

As stated above, the strong interaction between the polypeptide and the mineral indicate that a change in the mineral-solution interfacial energy is involved in the mineralization behavior observed with ADP7. However, the fact that the HA precipitation was only observed in ADP7 and none of the other strong binders, i.e.: ADP 1, ADP2 and ADP4, indicates that binding alone is not responsible for the observed effect. One possible explanation of the observed effect is that the ADP7 may act as a heterogeneous nucleation site for the HA, thus, promoting the precipitation of HA in preference to other phases, possibly through molecular recognition. ADP7 comprises of the strong binders ADP1 and ADP2 and the weak binding region, with ADP8 in between. Mineralization experiments done to compare the effect of the whole ADP7 vs. the ADP1, ADP2 and ADP8 separately show that HA formation occurs only when the ADP7 is present as a single polypeptide in the solution (FIG. 2 a, b). This suggests that structural features, which may be induced upon surface binding, are essential for the observed function. One interesting feature of the ADP7 is the abundance of basic histidine (H) residues in the mineral binding regions (ADP1 and ADP2) and the absence in the non-binding middle region (ADP8). Histidine is an amino acid commonly found in the calcium-binding proteins [4, 5, and 6] and may be playing a role in ADP7 function as well. Moreover, the molecular structure predictions done using RAMP software show that ADP7 tends to form a loop-like structure both on the full protein and as a single polypeptide. This conformation brings the histidine residues in close proximity, which further implies the importance of the histidine residues.

Although we know that ADP7 promotes the precipitation of HA in preference to OCP, the binding and biomineralization behaviors of ADP5 and ADP7, however, imply an interesting mechanism for amelogenin mediated mineralization during the formation of enamel. The fact that two different amelogenin derived polypeptides emulate different aspects of the parent protein brings up the point that these polypeptides are different functional regions within the original amelogenin sequence. Namely, ADP5 may be the region responsible for increased mineralization kinetics through increasing local supersaturation and ADP7 may be the region responsible for favoring the phase transformation towards HA through altering the interfacial energy.

REFERENCES FOR EXAMPLE 3

1. Meyer, J. L. and C. C. Weatherall, Amorphous to crystalline calcium phosphate phase transformation at elevated pH. *Journal of Colloid and Interface Science*, 1982. 89(1): pp. 257-267.
2. Eanes, E. D. and J. L. Meyer, Maturation of Cratalline Calcium Phosphates in Aqueous Suspensions at Physiologic pH. *Calcified Tissue Research*, 1977. 23(3): pp. 259-269.
3. Brown, W. E., et al., Crystallographic and Chemical Relations between Octacalcium Phosphate and Hydroxyapatite. *Nature*, 1962. 196(4859): pp. 1050-1052.
4. Fan, G. C., et al., Regulation of myocardial function by histidine-rich, calcium-binding protein. *American Journal of Physiology-Heart and Circulatory Physiology*, 2004. 287(4): pp. H1705-H1711.
5. 38 Gregory, K. N., et al., Histidine-rich Ca binding protein: a regulator of sarcoplasmic reticulum calcium sequestration and cardiac function. *Journal of Molecular and Cellular Cardiology*, 2006. 40(5): pp. 653-665.
6. Pathak, R. K., R. G. W. Anderson, and S. L. Hofmann, Histidine-rich calcium binding protein, a sarcoplasmic reticulum protein of striated muscle, is also abundant in arteriolar smooth muscle cells. *Journal of Muscle Research and Cell Motility,* 1992. 13(3): pp. 366-376.

We claim:

1. An isolated polypeptide consisting of 1 to 10 copies of a polypeptide consisting of 12-42 contiguous amino acids of the amino acid sequence of SEQ ID NO:4, (HPP(S/T)HTLQPHHH(L/I)PVVPAQQPV(A/I)PQQPMMPVPG(H/Q)HSMTP(T/I)QH) (ADP7).

2. The isolated polypeptide of claim 1, wherein the polypeptide is selected from the group consisting of
   (i) (HTLQPHHH(L/I)PVV)$_{1-10}$ (SEQ ID NO: 12) (ADP1);
   (ii) (VPG(H/Q)HSMTP(T/I)QH)$_{1-10}$ (SEQ ID NO: 13) (ADP2)
   (iii) (HPP(S/T)HTLQPHHH(L/I)PVV)$_{1-10}$ (SEQ ID NO: 14) (ADP4);
   (iv) (PAQQPV(A-I)PQQPMMP)$_{1-10}$ (SEQ ID NO: 15) (ADP8);
   (v) (HPP(S/T)HTLQPHHH(L/I)PVVPAQQPV(A/I)PQQPMMPVPG (H/Q)HSMTP(T/I)QH)$_{1-10}$ (SEQ ID NO: 4) (ADP7);
   (vi) (HTLQPHHHLPVV)$_{1-10}$ (SEQ ID NO: 16) (ADP1M);
   (vii) (HTLQPHHHIPVV)$_{1-10}$ (SEQ ID NO: 17) (ADP1H);
   (viii) (VPGHHSMTPTQH)$_{1-10}$ (SEQ ID NO: 18) (ADP2M)
   (ix) (VPGQHSMTPIQH)$_{1-10}$ (SEQ ID NO: 19) (ADP2H)
   (x) (HPPSHTLQPHHHLPVV)$_{1-10}$ (SEQ ID NO: 20) (ADP4M);
   (xi) (HPPTHTLQPHHHIPVV)$_{1-10}$ (SEQ ID NO: 21) (ADP4H);
   (xii) (HPPSHTLQPHHHLPVVPAQQPVAPQQPMMPVPGHHSMTPTQH)$_{1-10}$ (SEQ ID NO: 8) (ADP7M);
   (xiii) (HPPTHTLQPHHHIPVVPAQQPVIPQQPMMPVPGQHSMTPIQH)$_{1-10}$ (SEQ ID NO: 9) (ADP7H);
   (xiv) (PAQQPVAPQQPMMP)$_{1-10}$ (SEQ ID NO: 22) (ADP8M); and
   (xv) (PAQQPVIPQQPMMP)$_{1-10}$ (SEQ ID NO: 23) (ADP8H).

3. The isolated polypeptide of claim 1 wherein the polypeptide comprises the amino acid sequence of (HPPSHTLQPHHHLPVVPAQQPVAPQQPMMPVPGHHSMTPTQH)$_{1-10}$ (SEQ ID NO: 8) (ADP7M), or (HPPTHTLQPHHHIPVVPAQQPVIPQQPMMPVPGQHSMTPIQH)$_{1-10}$ (SEQ ID NO: 9) (ADP7H).

4. The isolated polypeptide of claim 1 consisting of 2-10 copies of the polypeptide.

5. The isolated polypeptide of claim 2 consisting of 2-10 copies of the polypeptide selected from the group.

6. A recombinant fusion polypeptide, comprising:
   (a) the polypeptide of claim 1; and
   (b) a heterologous polypeptide.

7. A recombinant fusion polypeptide, comprising:
   (a) the polypeptide of claim 4; and
   (b) a heterologous polypeptide.

8. The recombinant fusion protein of claim 6, wherein the heterologous polypeptide is selected from the group consisting of detectable polypeptides, polypeptide affinity tags, peptide markers, a fusion tag, anti-microbial polypeptides, biomineralization-promoting polypeptides, inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

9. The recombinant fusion protein of claim 7, wherein the heterologous polypeptide is selected from the group consisting of detectable polypeptides, polypeptide affinity tags, peptide markers, a fusion tag, anti-microbial polypeptides, biomineralization-promoting polypeptides, inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

10. A composition, comprising:
    (a) the polypeptide of claim 1; and
    (b) a non-peptide moiety linked to the polypeptide.

11. A composition, comprising:
    (a) the polypeptide of claim 4; and
    (b) a non-peptide moiety linked to the polypeptide.

12. The composition of claim 10, wherein the non-peptide moiety is selected from the group consisting of radioactive isotopes, non-peptide affinity tags, isotope-coded affinity tags, fluorophores, nanotubes, nanowires, nanoparticles, atomic clusters, quantum dots, single layer or multilayer atomic materials, inorganic ions or ion clusters, organic-inorganic hybrid nanostructures, fish flour, amino acids, and non-peptide polymers.

13. The composition of claim 11, wherein the non-peptide moiety is selected from the group consisting of radioactive isotopes, non-peptide affinity tags, isotope-coded affinity tags, fluorophores, nanotubes, nanowires, nanoparticles, atomic clusters, quantum dots, single layer or multilayer atomic materials, inorganic ions or ion clusters, organic-inorganic hybrid nanostructures, fish flour, amino acids, and non-peptide polymers.

14. A pharmaceutical composition, comprising
    (a) the polypeptide of claim 1; and
    (b) a pharmaceutically acceptable carrier.

15. A pharmaceutical composition, comprising
    (a) the polypeptide of claim 4; and
    (b) a pharmaceutically acceptable carrier.

16. An oral care product, comprising the polypeptide of claim 1.

17. An oral care product, comprising the polypeptide of claim 4.

18. The oral care product of claim 16, wherein the dental care product is selected from the group consisting of toothpaste, toothpowders, mouthwash, dental floss, liquid dentifrices, dental tablets, topical gels, troches, chewing gums, dental pastes, gingival massage creams, gargle tablets, lozenges, and food products.

19. The oral care product of claim 17, wherein the dental care product is selected from the group consisting of toothpaste, toothpowders, mouthwash, dental floss, liquid dentifrices, dental tablets, topical gels, troches, chewing gums, dental pastes, gingival massage creams, gargle tablets, lozenges, and food products.

20. A method for treating dental disease, comprising administering to a subject in need thereof an amount effective to treat the dental disease of the polypeptide of claim 1.

21. The method of claim 20, wherein the dental disorder is selected from the group consisting of periodontitis, tooth erosion, hypersensitivity, bacterial plaque, dental fluorosis, tooth decay, carries, tooth resorption, and gingival recession.

* * * * *

UNITED STATES PATENT AND TRADEMARK OFFICE
CERTIFICATE OF CORRECTION

PATENT NO. : 9,809,633 B2  
APPLICATION NO. : 15/015360  
DATED : November 7, 2017  
INVENTOR(S) : Mehmet Sarikaya et al.

Page 1 of 1

It is certified that error appears in the above-identified patent and that said Letters Patent is hereby corrected as shown below:

Column 1, Lines 14-19 replace with the following:
STATEMENT OF GOVERNMENT SUPPORT
This invention was made with government support under Grant No. DMR0520567 awarded by the National Science Foundation, and Grant Nos. R01 DE015109 and R01 DE013045 awarded by the National Institutes of Health. The government has certain rights in the invention.

Signed and Sealed this
Thirtieth Day of April, 2019

Andrei Iancu
*Director of the United States Patent and Trademark Office*

```
                          SEQUENCE LISTING

<160> NUMBER OF SEQ ID NOS: 43

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is A or S

<400> SEQUENCE: 1

Trp Pro Xaa Thr Asp Lys Thr Lys Arg Glu Glu Val Asp
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (9)..(9)
<223> OTHER INFORMATION: X is E or A
<220> FEATURE:
<221> NAME/KEY: MISC_FEATURE
<222> LOCATION: (10)..(10)
<223> OTHER INFORMATION: X is K,N, or A
<220> FEATURE:
<221> NAME/KEY: MISC_FEATURE
<222> LOCATION: (18)..(18)
<223> OTHER INFORMATION: X is T or V
<220> FEATURE:
<221> NAME/KEY: MISC_FEATURE
<222> LOCATION: (19)..(19)
<223> OTHER INFORMATION: X is D or A
<220> FEATURE:
<221> NAME/KEY: MISC_FEATURE
<222> LOCATION: (20)..(20)
<223> OTHER INFORMATION: X is R or A

<400> SEQUENCE: 2

Pro Gly Tyr Ile Asn Xaa Ser Tyr Xaa Xaa Ser His Ser Gln Ala Ile
1               5                   10                  15

Asn Xaa Xaa Xaa Thr Ala
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic

<400> SEQUENCE: 3

Leu Pro Pro Leu Phe Ser Met Pro Leu Ser Pro Ile Leu Pro Glu Leu
1               5                   10                  15

Pro Leu Glu Ala Trp Pro Ala Thr
            20
```

```
<210> SEQ ID NO 4
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is S or T
<220> FEATURE:
<221> NAME/KEY: MISC_FEATURE
<222> LOCATION: (13)..(13)
<223> OTHER INFORMATION: X is L or I
<220> FEATURE:
<221> NAME/KEY: MISC_FEATURE
<222> LOCATION: (23)..(23)
<223> OTHER INFORMATION: X is A or I
<220> FEATURE:
<221> NAME/KEY: MISC_FEATURE
<222> LOCATION: (34)..(34)
<223> OTHER INFORMATION: X is H or Q
<220> FEATURE:
<221> NAME/KEY: MISC_FEATURE
<222> LOCATION: (40)..(40)
<223> OTHER INFORMATION: X is T or I

<400> SEQUENCE: 4

His Pro Pro Xaa His Thr Leu Gln Pro His His Xaa Pro Val Val
1               5                   10                  15

Pro Ala Gln Gln Pro Val Xaa Pro Gln Gln Pro Met Met Pro Val Pro
            20                  25                  30

Gly Xaa His Ser Met Thr Pro Xaa Gln His
        35                  40

<210> SEQ ID NO 5
<211> LENGTH: 44
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (10)..(10)
<223> OTHER INFORMATION: X is K or N
<220> FEATURE:
<221> NAME/KEY: MISC_FEATURE
<222> LOCATION: (18)..(18)
<223> OTHER INFORMATION: X is T or V
<220> FEATURE:
<221> NAME/KEY: MISC_FEATURE
<222> LOCATION: (28)..(28)
<223> OTHER INFORMATION: X is L or F
<220> FEATURE:
<221> NAME/KEY: MISC_FEATURE
<222> LOCATION: (32)..(32)
<223> OTHER INFORMATION: X is K or N
<220> FEATURE:
<221> NAME/KEY: MISC_FEATURE
<222> LOCATION: (40)..(40)
<223> OTHER INFORMATION: X is T or V

<400> SEQUENCE: 5

Pro Gly Tyr Ile Asn Xaa Ser Tyr Glu Xaa Ser His Ser Gln Ala Ile
1               5                   10                  15

Asn Xaa Asp Arg Thr Ala Pro Gly Tyr Ile Asn Xaa Ser Tyr Glu Xaa
            20                  25                  30

Ser His Ser Gln Ala Ile Asn Xaa Asp Arg Thr Ala
        35                  40
```

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

Pro Gly Tyr Ile Asn Phe Ser Tyr Glu Asn Ser His Ser Gln Ala Ile
1               5                   10                  15

Asn Val Asp Arg Thr Ala
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic

<400> SEQUENCE: 7

Pro Gly Tyr Ile Asn Leu Ser Tyr Glu Lys Ser His Ser Gln Ala Ile
1               5                   10                  15

Asn Thr Asp Arg Thr Ala
            20

<210> SEQ ID NO 8
<211> LENGTH: 42
<212> TYPE: PRT
<213> ORGANISM: Artificial Sequence
<220> FEATURE:
<223> OTHER INFORMATION: Synthetic

<400> SEQUENCE: 8

His Pro Pro Ser His Thr Leu Gln Pro His His His Leu Pro Val Val
1               5                   10                  15

Pro Ala Gln Gln Pro Val Ala Pro Gln Gln Pro Met Met Pro Val Pro
            20                  25                  30

Gly His His Ser Met Thr Pro Thr Gln His
        35                  40

<210> SEQ ID NO 9
<211> LENGTH: 42
<212> TYPE: PRT
<213> ORGANISM: Artificial Sequence
<220> FEATURE:
<223> OTHER INFORMATION: Synthetic

<400> SEQUENCE: 9

His Pro Pro Thr His Thr Leu Gln Pro His His His Ile Pro Val Val
1               5                   10                  15

Pro Ala Gln Gln Pro Val Ile Pro Gln Gln Pro Met Met Pro Val Pro
            20                  25                  30

Gly Gln His Ser Met Thr Pro Ile Gln His
        35                  40

<210> SEQ ID NO 10
<211> LENGTH: 13
<212> TYPE: PRT
<213> ORGANISM: Artificial Sequence
<220> FEATURE:
<223> OTHER INFORMATION: Synthetic

```
<400> SEQUENCE: 10

Trp Pro Ala Thr Asp Lys Thr Lys Arg Glu Glu Val Asp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Trp Pro Ser Thr Asp Lys Thr Lys Arg Glu Glu Val Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: X is L or I

<400> SEQUENCE: 12

His Thr Leu Gln Pro His His His Xaa Leu Ile Pro Val Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is H or Q
<220> FEATURE:
<221> NAME/KEY: MISC_FEATURE
<222> LOCATION: (10)..(10)
<223> OTHER INFORMATION: X is T or I

<400> SEQUENCE: 13

Val Pro Gly Xaa His Ser Met Thr Pro Xaa Gln His
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is S or T
<220> FEATURE:
<221> NAME/KEY: MISC_FEATURE
<222> LOCATION: (13)..(13)
<223> OTHER INFORMATION: X is L or I

<400> SEQUENCE: 14

His Pro Pro Xaa His Thr Leu Gln Pro His His His Xaa Pro Val Val
1               5                   10                  15
```

<210> SEQ ID NO 15
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: X is A or I

<400> SEQUENCE: 15

Pro Ala Gln Gln Pro Val Xaa Pro Gln Gln Pro Met Met Pro
1               5                  10

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

His Thr Leu Gln Pro His His His Leu Pro Val Val
1               5                  10

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

His Thr Leu Gln Pro His His His Ile Pro Val Val
1               5                  10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Val Pro Gly His His Ser Met Thr Pro Thr Gln His
1               5                  10

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Val Pro Gly Gln His Ser Met Thr Pro Ile Gln His
1               5                  10

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

His Pro Pro Ser His Thr Leu Gln Pro His His His Leu Pro Val Val

```
<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

His Pro Pro Thr His Thr Leu Gln Pro His His His Ile Pro Val Val
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Pro Ala Gln Gln Pro Val Ala Pro Gln Gln Pro Met Met Pro
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic

<400> SEQUENCE: 23

Pro Ala Gln Gln Pro Val Ile Pro Gln Gln Pro Met Met Pro
1               5                   10

<210> SEQ ID NO 24
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (10)..(10)
<223> OTHER INFORMATION: X is K or N
<220> FEATURE:
<221> NAME/KEY: MISC_FEATURE
<222> LOCATION: (18)..(18)
<223> OTHER INFORMATION: X is T or V

<400> SEQUENCE: 24

Pro Gly Tyr Ile Asn Xaa Ser Tyr Glu Xaa Ser His Ser Gln Ala Ile
1               5                   10                  15

Asn Xaa Asp Arg Thr Ala
            20

<210> SEQ ID NO 25
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
```

<223> OTHER INFORMATION: X is L or F
<220> FEATURE:
<221> NAME/KEY: MISC_FEATURE
<222> LOCATION: (10)..(10)
<223> OTHER INFORMATION: X is K or N
<220> FEATURE:
<221> NAME/KEY: MISC_FEATURE
<222> LOCATION: (18)..(18)
<223> OTHER INFORMATION: X is T or V

<400> SEQUENCE: 25

Pro Gly Tyr Ile Asn Xaa Ser Tyr Ala Xaa Lys Asn Ser His Ser Gln
1               5                   10                  15

Ala Ile Asn Thr Val Ala Arg Thr Ala
            20                  25

<210> SEQ ID NO 26
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (10)..(10)
<223> OTHER INFORMATION: X is A or N
<220> FEATURE:
<221> NAME/KEY: MISC_FEATURE
<222> LOCATION: (18)..(18)
<223> OTHER INFORMATION: X is T or V

<400> SEQUENCE: 26

Pro Gly Tyr Ile Asn Xaa Ser Tyr Glu Xaa Ser His Ser Gln Ala Ile
1               5                   10                  15

Asn Xaa Asp Ala Thr Ala
            20

<210> SEQ ID NO 27
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is L or F
<220> FEATURE:
<221> NAME/KEY: MISC_FEATURE
<222> LOCATION: (10)..(10)
<223> OTHER INFORMATION: X is A or N
<220> FEATURE:
<221> NAME/KEY: MISC_FEATURE
<222> LOCATION: (18)..(18)
<223> OTHER INFORMATION: X is T or V

<400> SEQUENCE: 27

Pro Gly Tyr Ile Asn Xaa Ser Tyr Ala Xaa Ser His Ser Gln Ala Ile
1               5                   10                  15

Asn Xaa Ala Ala Thr Ala
            20

<210> SEQ ID NO 28
<211> LENGTH: 59
<212> TYPE: PRT
<213> ORGANISM: Artificial Sequence
<220> FEATURE:
<223> OTHER INFORMATION: Synthetic

<400> SEQUENCE: 28

Met Pro Leu Pro Pro His Pro Gly Ser Pro Gly Tyr Ile Asn Leu Ser
1               5                   10                  15

Tyr Glu Val Leu Thr Pro Leu Lys Trp Tyr Gln Ser Met Ile Arg Gln
            20                  25                  30

Pro Pro Leu Ser Pro Ile Leu Pro Glu Leu Pro Leu Glu Ala Trp Pro
        35                  40                  45

Ala Thr Asp Lys Thr Lys Arg Glu Glu Val Asp
    50                  55

<210> SEQ ID NO 29
<211> LENGTH: 45
<212> TYPE: PRT
<213> ORGANISM: Artificial Sequence
<220> FEATURE:
<223> OTHER INFORMATION: Synthetic

<400> SEQUENCE: 29

Met Pro Leu Pro Pro His Pro Gly Ser Pro Gly Tyr Ile Asn Leu Ser
1               5                   10                  15

Tyr Glu Val Leu Thr Pro Leu Lys Trp Tyr Gln Ser Met Ile Arg Gln
            20                  25                  30

Pro Tyr Pro Ser Tyr Gly Tyr Glu Pro Met Gly Gly Trp
        35                  40                  45

<210> SEQ ID NO 30
<211> LENGTH: 38
<212> TYPE: PRT
<213> ORGANISM: Artificial Sequence
<220> FEATURE:
<223> OTHER INFORMATION: Synthetic

<400> SEQUENCE: 30

Leu Pro Pro His Pro Gly Ser Pro Gly Tyr Ile Asn Leu Ser Tyr Glu
1               5                   10                  15

Val Leu Thr Pro Leu Lys Trp Tyr Gln Ser Met Ile Arg Gln Pro Tyr
            20                  25                  30

Pro Ser Tyr Gly Tyr Glu
        35

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Ser Pro Ile Leu Pro Glu Leu Pro Leu Glu Ala Trp Pro Ala Thr Asp
1               5                   10                  15

Lys

<210> SEQ ID NO 32
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE

```
<222> LOCATION: (10)..(10)
<223> OTHER INFORMATION: X is K or N

<400> SEQUENCE: 32

Pro Gly Tyr Ile Asn Leu Ser Tyr Ala Xaa Ser His Ser Gln Ala Ile
1               5                   10                  15

Asn Thr Ala Arg Thr Ala
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X is A or N

<400> SEQUENCE: 33

Pro Gly Tyr Ile Asn Leu Ser Tyr Glu Xaa Ser His Ser Gln Ala Ile
1               5                   10                  15

Asn Thr Asp Ala Thr Ala
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X is A or N

<400> SEQUENCE: 34

Pro Gly Tyr Ile Asn Leu Ser Tyr Ala Xaa Ser His Ser Gln Ala Ile
1               5                   10                  15

Asn Thr Ala Ala Thr Ala
            20

<210> SEQ ID NO 35
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X is K or N

<400> SEQUENCE: 35

Pro Gly Tyr Ile Asn Phe Ser Tyr Ala Xaa Ser His Ser Gln Ala Ile
1               5                   10                  15

Asn Val Ala Arg Thr Ala
            20

<210> SEQ ID NO 36
<211> LENGTH: 22
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (10)..(10)
<223> OTHER INFORMATION: X is A or N

<400> SEQUENCE: 36

Pro Gly Tyr Ile Asn Phe Ser Tyr Glu Xaa Ser His Ser Gln Ala Ile
1               5                   10                  15

Asn Val Asp Ala Thr Ala
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: X ia A or N

<400> SEQUENCE: 37

Pro Gly Tyr Ile Asn Phe Ser Tyr Ala Xaa Ser His Ser Gln Ala Ile
1               5                   10                  15

Asn Val Ala Ala Thr Ala
            20

<210> SEQ ID NO 38
<211> LENGTH: 22
<212> TYPE: PRT
<213> ORGANISM: Artificial Sequence
<220> FEATURE:
<223> OTHER INFORMATION: Synthetic

<400> SEQUENCE: 38

Pro Gly Tyr Ile Asn Leu Ser Tyr Ala Lys Ser His Ser Gln Ala Ile
1               5                   10                  15

Asn Thr Ala Arg Thr Ala
            20

<210> SEQ ID NO 39
<211> LENGTH: 22
<212> TYPE: PRT
<213> ORGANISM: Artificial Sequence
<220> FEATURE:
<223> OTHER INFORMATION: Synthetic

<400> SEQUENCE: 39

Pro Gly Tyr Ile Asn Leu Ser Tyr Glu Ala Ser His Ser Gln Ala Ile
1               5                   10                  15

Asn Thr Asp Ala Thr Ala
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic

<400> SEQUENCE: 40

Pro Gly Tyr Ile Asn Leu Ser Tyr Ala Ala Ser His Ser Gln Ala Ile
1               5                   10                  15

Asn Thr Ala Ala Thr Ala
            20
```

```
<210> SEQ ID NO 41
<211> LENGTH: 22
<212> TYPE: PRT
<213> ORGANISM: Artificial Sequence
<220> FEATURE:
<223> OTHER INFORMATION: Synthetic

<400> SEQUENCE: 41

Pro Gly Tyr Ile Asn Phe Ser Tyr Ala Asn Ser His Ser Gln Ala Ile
1               5                   10                  15

Asn Val Ala Arg Thr Ala
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic

<400> SEQUENCE: 42

Pro Gly Tyr Ile Asn Phe Ser Tyr Glu Ala Ser His Ser Gln Ala Ile
1               5                   10                  15

Asn Val Asp Ala Thr Ala
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic

<400> SEQUENCE: 43

Pro Gly Tyr Ile Asn Phe Ser Tyr Ala Ala Ser His Ser Gln Ala Ile
1               5                   10                  15

Asn Val Ala Ala Thr Ala
            20
```